United States Patent
Takada et al.

(10) Patent No.: US 10,923,663 B2
(45) Date of Patent: Feb. 16, 2021

(54) MONOAMINE COMPOUND AND ORGANIC ELECTROLUMINESCENCE DEVICE INCLUDING THE SAME

(71) Applicant: SAMSUNG DISPLAY CO., LTD., Yongin-si (KR)

(72) Inventors: Ichinori Takada, Yokohama (JP); Akinori Yamatani, Yokohama (JP); Ichiro Imada, Yokohama (JP); Hiroaki Itoi, Yokohama (JP)

(73) Assignee: Samsung Display Co., Ltd., Yongin-si (KR)

( * ) Notice: Subject to any disclaimer, the term of this patent is extended or adjusted under 35 U.S.C. 154(b) by 325 days.

(21) Appl. No.: 15/789,274

(22) Filed: Oct. 20, 2017

(65) Prior Publication Data

US 2018/0114907 A1    Apr. 26, 2018

(30) Foreign Application Priority Data

Oct. 21, 2016  (KR) .................. 10-2016-0137914
May 26, 2017  (KR) .................. 10-2017-0065359
Sep. 8, 2017  (KR) .................. 10-2017-0114951

(51) Int. Cl.
  *H01L 51/50*   (2006.01)
  *H01L 51/00*   (2006.01)
  (Continued)

(52) U.S. Cl.
  CPC .......... *H01L 51/006* (2013.01); *C07C 211/54* (2013.01); *C07C 211/56* (2013.01);
  (Continued)

(58) Field of Classification Search
  None
  See application file for complete search history.

(56) References Cited

U.S. PATENT DOCUMENTS

| | | |
|---|---|---|
| 6,723,455 B2 | 4/2004 | Ueda et al. |
| 10,424,741 B2 | 9/2019 | Lee et al. |
| 2016/0043316 A1 | 2/2016 | Takada et al. |

FOREIGN PATENT DOCUMENTS

| | | | |
|---|---|---|---|
| CN | 105418485 A | * 3/2016 | ........... C07D 209/86 |
| CN | 105418485 A | 3/2016 | |

(Continued)

OTHER PUBLICATIONS

He, et al., "Facile synthesis of 9, 10-Diarylphenanthrenes and poly(9,10-diarylphenanthrene)s", Organic Letters., vol. 10, No. 5, 2008, pp. 773-776, USACS, Washington, DC. ISSN:1523-7000.

*Primary Examiner* — Gregory D Clark
(74) *Attorney, Agent, or Firm* — Lewis Roca Rothgerber Christie LLP

(57) ABSTRACT

Provided are a monoamine compound and an organic electroluminescence device including the same. The monoamine compound according to an example embodiment is represented by the following Formula 1

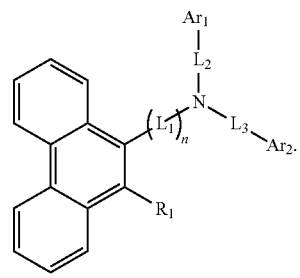

[Formula 1]

28 Claims, 2 Drawing Sheets

(51) Int. Cl.
  *C07F 7/08* (2006.01)
  *H01L 51/52* (2006.01)
  *C07C 211/54* (2006.01)
  *C07C 211/56* (2006.01)
  *C07C 211/58* (2006.01)
  *C07C 211/61* (2006.01)
  *C07C 255/58* (2006.01)
  *C07D 213/38* (2006.01)
  *C07D 307/91* (2006.01)
  *C07D 333/50* (2006.01)
  *C07D 333/76* (2006.01)

(52) U.S. Cl.
  CPC .......... *C07C 211/58* (2013.01); *C07C 211/61* (2013.01); *C07C 255/58* (2013.01); *C07D 213/38* (2013.01); *C07D 307/91* (2013.01); *C07D 333/50* (2013.01); *C07D 333/76* (2013.01); *C07F 7/081* (2013.01); *H01L 51/0061* (2013.01); *H01L 51/0094* (2013.01); *H01L 51/5296* (2013.01); *H01L 51/001* (2013.01); *H01L 51/0052* (2013.01); *H01L 51/0058* (2013.01); *H01L 51/0067* (2013.01); *H01L 51/0073* (2013.01); *H01L 51/0074* (2013.01); *H01L 51/5012* (2013.01); *H01L 51/5064* (2013.01); *H01L 51/5072* (2013.01); *H01L 51/5088* (2013.01); *H01L 51/5092* (2013.01); *H01L 51/5206* (2013.01); *H01L 51/5228* (2013.01)

(56) References Cited

FOREIGN PATENT DOCUMENTS

| | | | | |
|---|---|---|---|---|
| JP | 3915256 | B2 | 2/2007 | |
| JP | 2010-222261 | * | 10/2010 | ........... C07D 209/86 |
| JP | 2010222261 A | * | 10/2010 | ........... C07D 209/86 |
| JP | 4951829 | B2 | 3/2012 | |
| JP | 5606001 | B2 | 10/2014 | |
| KR | 2011047803 | * | 5/2011 | ............ C09K 11/06 |
| KR | 10-1233379 | B1 | 2/2013 | |
| KR | 10-2015-0145033 | A | 12/2015 | |
| KR | 10-2016-0019839 | A | 2/2016 | |
| KR | 10-1737212 | B1 | 5/2017 | |

* cited by examiner

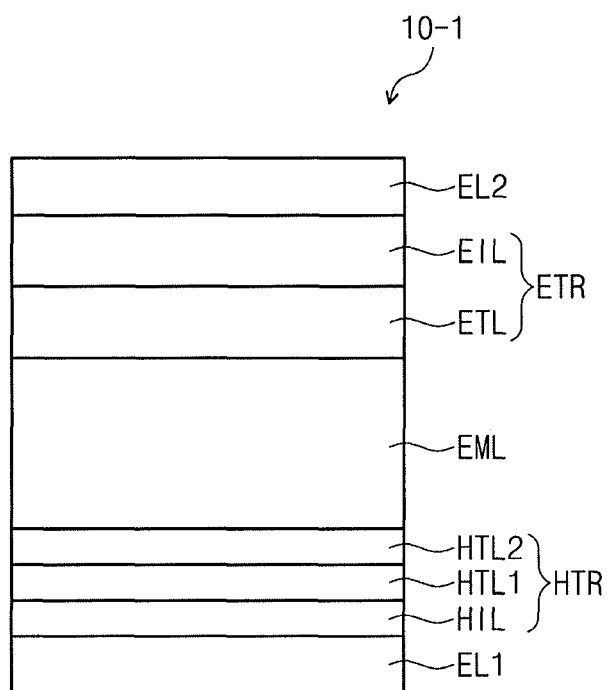

MONOAMINE COMPOUND AND ORGANIC ELECTROLUMINESCENCE DEVICE INCLUDING THE SAME

CROSS-REFERENCE TO RELATED APPLICATIONS

Korean Patent Application Nos. 10-2016-0137914, filed on Oct. 21, 2016, 10-2017-0065359, filed on May 26, 2017, and 10-2017-0114951, filed on Sep. 8, 2017, and entitled: "Monoamine Compound and Organic Electroluminescence Device Including the Same," are each incorporated by reference herein in its entirety.

BACKGROUND

1. Field

Embodiments relate to a compound and an organic electroluminescence device including the same.

2. Description of the Related Art

An organic electroluminescence display is a so called self-luminescent display. In the organic electroluminescence display, recombination of holes and electrons injected from a first electrode and a second electrode in an emission layer may create emitted light. A luminescent material, for example, an organic compound, may be in the emission layer.

SUMMARY

Embodiments are directed to a monoamine compound represented by the following Formula 1:

[Formula 1]

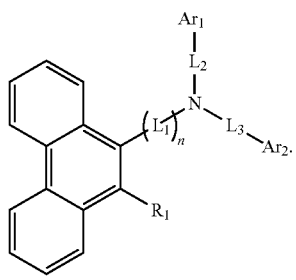

In Formula 1, $L_1$ may be a substituted or unsubstituted arylene group having 6 to 30 carbon atoms for forming a ring, or a substituted or unsubstituted heteroarylene group having 2 to 30 carbon atoms for forming a ring, n may be 1 or 2, $L_2$ and $L_3$ may each independently be a direct linkage, a substituted or unsubstituted arylene group having 6 to 30 carbon atoms for forming a ring, or a substituted or unsubstituted heteroarylene group having 2 to 30 carbon atoms for forming a ring, $R_1$ may be a substituted or unsubstituted alkyl group having 1 to 10 carbon atoms, a substituted or unsubstituted aryl group having 6 to 30 carbon atoms for forming a ring, a substituted or unsubstituted heteroaryl group having 2 to 30 carbon atoms for forming a ring, or a substituted or unsubstituted aryl silyl group, and $Ar_1$ and $Ar_2$ may each independently be a substituted or unsubstituted aryl group having 6 to 30 carbon atoms for forming a ring, or a substituted or unsubstituted heteroaryl group having 2 to 30 carbon atoms for forming a ring.

In an embodiment, the monoamine compound represented by Formula 1 may be represented by the following Formula 2-1 or 2-2:

[Formula 2-1]

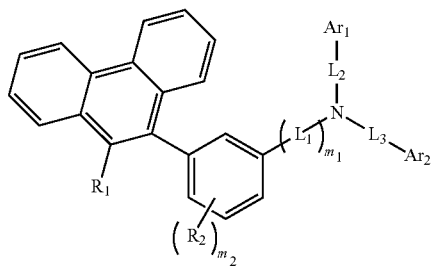

[Formula 2-2]

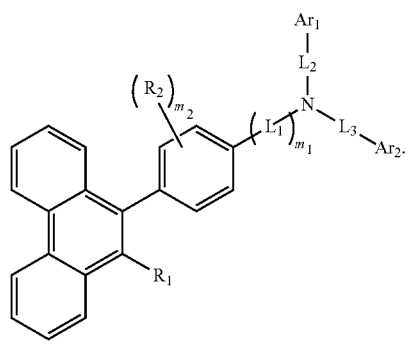

In Formulae 2-1 and 2-2, $m_1$ may be 0 or 1, $m_2$ may be an integer of 0 to 2, $R_2$ may be a hydrogen atom, a deuterium atom, a substituted or unsubstituted alkyl group having 1 to 10 carbon atoms, a substituted or unsubstituted aryl group having 6 to 30 carbon atoms for forming a ring, a substituted or unsubstituted heteroaryl group having 2 to 30 carbon atoms for forming a ring, or a substituted or unsubstituted aryl silyl group, or may be combined with an adjacent group to form a ring, and $Ar_1$, $Ar_2$, $L_1$, $L_2$, $L_3$, and $R_1$ are the same as described above.

In an embodiment, the monoamine compound represented by Formula 2-1 may be represented by one of the following Formulae 2-1-1 to 2-1-3:

[Formula 2-1-1]

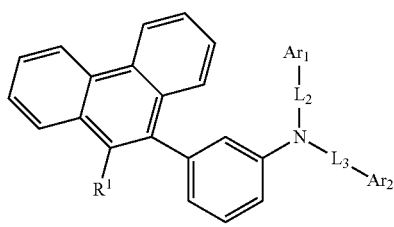

[Formula 2-1-2]

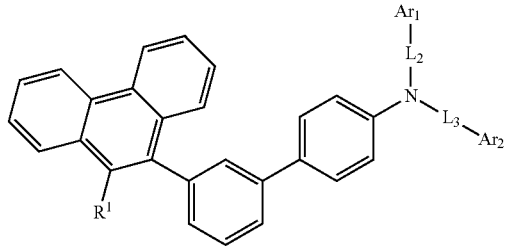

[Formula 2-1-3]

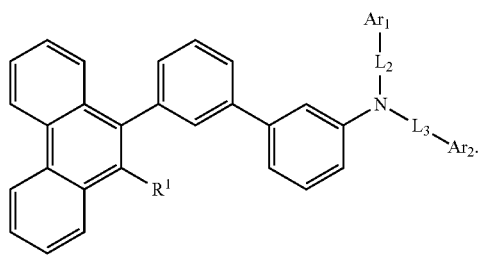

In Formulae 2-1-1 to 2-1-3, $Ar_1$ and $Ar_2$, $L_2$ and $L_3$, and $R_1$ are the same as described above.

In an embodiment, the monoamine compound represented by Formula 2-2 may be represented by one of the following Formulae 2-2-1 to 2-2-3.

[Formula 2-2-1]

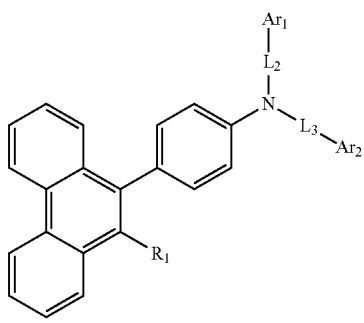

[Formula 2-2-2]

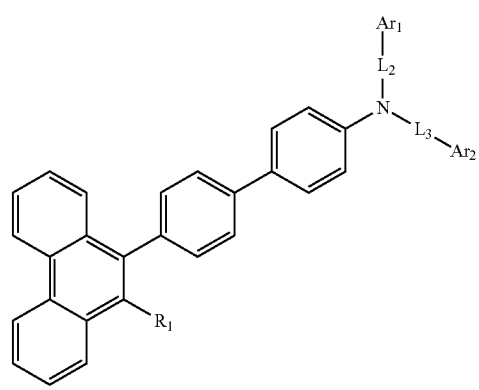

[Formula 2-2-3]

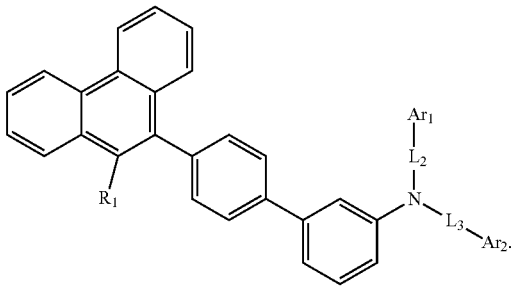

In Formulae 2-2-1 to 2-2-3, $Ar_1$ and $Ar_2$, $L_2$ and $L_3$ and $R_1$ are the same as described above.

$R_1$ may be a substituted or unsubstituted phenyl group, $L_3$ may be a substituted or unsubstituted phenylene group, and $Ar_2$ may be a substituted or unsubstituted naphthyl group.

$L_2$ may be a substituted or unsubstituted phenylene group, and $Ar_1$ may be a substituted or unsubstituted phenyl group.

$L_2$ may be a direct linkage, and $Ar_1$ may be a substituted or unsubstituted dibenzofuranyl group.

In an embodiment, $L_1$ may be a substituted or unsubstituted phenylene group, a substituted or unsubstituted divalent biphenyl group, or a substituted or unsubstituted naphthylene group.

In an embodiment, $R_1$ may be a substituted or unsubstituted phenyl group, a substituted or unsubstituted naphthyl group, a substituted or unsubstituted biphenyl group, or a substituted or unsubstituted nitrogen-containing heteroaryl group.

In an embodiment, $Ar_1$ and $Ar_2$ may each independently be a substituted or unsubstituted phenyl group, a substituted or unsubstituted biphenyl group, a substituted or unsubstituted terphenyl group, a substituted or unsubstituted naphthyl group, a substituted or unsubstituted phenanthryl group, or a substituted or unsubstituted fluorenyl group.

In an embodiment, $Ar_1$ and $Ar_2$ may each independently be a substituted or unsubstituted dibenzofuranyl group, a substituted or unsubstituted dibenzothiophenyl group, a substituted or unsubstituted benzonaphthofuranyl group, or a substituted or unsubstituted benzonaphthothiophenyl group.

In an embodiment, $Ar_1$ and $Ar_2$ may each independently be represented by the following Formula 3:

[Formula 3]

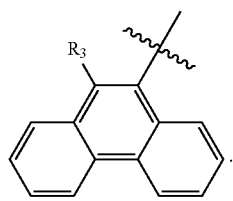

in case $Ar_1$ and $Ar_2$ are each independently represented by Formula 3, in formula 1, $L_2$ and $L_3$ may each independently be a substituted or unsubstituted arylene group having 6 to 30 carbon atoms for forming a ring, or a substituted or unsubstituted heteroarylene group having 2 to 30 carbon atoms for forming a ring In formula 3, $R_3$ is a substituted or unsubstituted alkyl group having 1 to 10 carbon atoms, a substituted or unsubstituted aryl group having 6 to 30 carbon atoms for forming a ring, a substituted or unsubstituted heteroaryl group having 2 to 30 carbon atoms for forming a ring, or a substituted or unsubstituted aryl silyl group.

In an embodiment, $Ar_1$ and $Ar_2$ may each independently be represented by the following Formula 4:

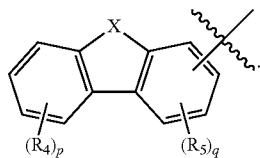

[Formula 4]

In Formula 4, X is O or S, $R_4$ and $R_5$ may each independently be a hydrogen atom, a deuterium atom, a substituted or unsubstituted alkyl group having 1 to 10 carbon atoms, a substituted or unsubstituted aryl group having 6 to 30 carbon atoms for forming a ring, a substituted or unsubstituted heteroaryl group having 2 to 30 carbon atoms for forming a ring, or a substituted or unsubstituted aryl silyl group, p may be an integer of 0 to 4, and q may be an integer of 0 to 3.

In an embodiment, $L_2$ and $L_3$ may each independently be a direct linkage, a substituted or unsubstituted phenylene group, a substituted or unsubstituted divalent biphenyl group, or a substituted or unsubstituted naphthylene group.

In an example embodiment, an organic electroluminescence device includes a first electrode, a hole transport region provided on the first electrode, an emission layer provided on the hole transport region, an electron transport region provided on the emission layer, and a second electrode provided on the electron transport region. At least one of the hole transport region, the emission region, and the electron transport region includes a monoamine compound represented by the following Formula 1:

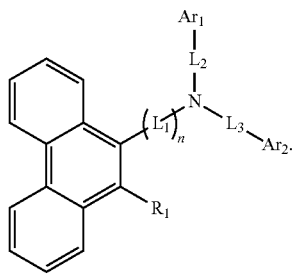

[Formula 1]

In Formula 1, $L_1$ may be a substituted or unsubstituted arylene group having 6 to 30 carbon atoms for forming a ring, or a substituted or unsubstituted heteroarylene group having 2 to 30 carbon atoms for forming a ring, n may be 1 or 2, $L_2$ and $L_3$ may each independently be a direct linkage, a substituted or unsubstituted arylene group having 6 to 30 carbon atoms for forming a ring, or a substituted or unsubstituted heteroarylene group having 2 to 30 carbon atoms for forming a ring, $R_1$ may be a substituted or unsubstituted alkyl group having 1 to 10 carbon atoms, a substituted or unsubstituted aryl group having 6 to 30 carbon atoms for forming a ring, a substituted or unsubstituted heteroaryl group having 2 to 30 carbon atoms for forming a ring, or a substituted or unsubstituted aryl silyl group, and $Ar_1$ and $Ar_2$ may each independently be a substituted or unsubstituted aryl group having 6 to 30 carbon atoms for forming a ring, or a substituted or unsubstituted heteroaryl group having 2 to 30 carbon atoms for forming a ring.

In an embodiment, the hole transport region may include the monoamine compound represented by Formula 1.

In an embodiment, the hole transport region may include a hole injection layer disposed on the first electrode and a hole transport layer disposed on the hole injection layer, and the hole transport layer may include the monoamine compound represented by Formula 1.

In an embodiment, the hole transport layer may make contact with the emission layer.

In an embodiment, the hole transport region may include a hole injection layer disposed on the first electrode, a first hole transport layer disposed on the hole injection layer, and a second hole transport layer disposed on the first hole transport layer and adjacent to the emission layer, wherein the second hole transport layer includes the monoamine compound represented by Formula 1.

BRIEF DESCRIPTION OF THE FIGURES

Features will become apparent to those of skill in the art by describing in detail example embodiments with reference to the attached drawings in which:

FIG. 3 illustrates a schematic cross-sectional view of an organic electroluminescence device according to an example embodiment.

DETAILED DESCRIPTION

Figure 1:
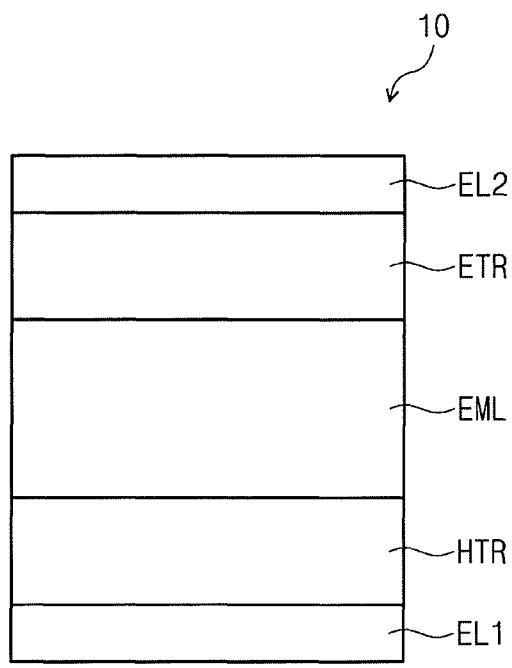
FIG. 1 illustrates a schematic cross-sectional view of an organic electroluminescence device according to an example embodiment.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey example implementations to those skilled in the art. In the drawing figures, the dimensions of layers and regions may be exaggerated for clarity of illustration. Like reference numerals refer to like elements throughout.

It will be understood that, although the terms first, second, etc. may be used herein to describe various elements, these elements should not be limited by these terms. These terms are only used to distinguish one element from another element. For example, a first element discussed below could be termed a second element, and similarly, a second element could be termed a first element. As used herein, the singular forms are intended to include the plural forms as well, unless the context clearly indicates otherwise.

It will be further understood that the terms "comprises" or "comprising," when used in this specification, specify the presence of stated features, numerals, steps, operations, elements, parts, or a combination thereof, but do not preclude the presence or addition of one or more other features, numerals, steps, operations, elements, parts, or a combination thereof. It will also be understood that when a layer, a film, a region, a plate, etc. is referred to as being 'on' another part, it can be directly on the other part, or intervening layers may also be present. On the contrary, when a layer, a film, a region, a plate, etc. is referred to as being 'under' another part, it can be directly under the other part, or intervening layers may also be present.

In the present disclosure,

means a part to be connected.

In the present disclosure, "substituted or unsubstituted" may mean substituted with at least one substituent selected from the group consisting of deuterium, halogen, cyano, nitro, silyl, boron, aryl amine, phosphine oxide, phosphine sulfide, alkyl, alkenyl, aryl, and heterocycle or unsubstituted. In addition, each of the substituent illustrated above may be substituted or unsubstituted. For example, biphenyl may be interpreted as aryl, or phenyl substituted with phenyl.

In the present disclosure, the terms "forming a ring by combining adjacent groups with each other" may mean forming a substituted or unsubstituted hydrocarbon ring or a substituted or unsubstituted heterocycle by combining adjacent groups with each other. A hydrocarbon ring may include an aliphatic hydrocarbon ring and an aromatic hydrocarbon ring. The heterocycle may include an aliphatic heterocycle and aromatic heterocycle. The hydrocarbon ring and heterocycle may be a monocycle or polycycle. In addition, the ring formed by combining adjacent groups may be connected with another ring to form a spiro structure.

In the present disclosure, the terms "an adjacent group" may mean a substituent at an atom which is directly connected with another atom at which a corresponding substituent is substituted, another substituent at an atom at which a corresponding substituent is substituted, or a substituent stereoscopically disposed at the nearest position to a corresponding substituent. For example, two methyl groups in 1,2-dimethylbenzene may be interpreted as "adjacent groups", and two ethyl groups in 1,1-diethylcyclopentene may be interpreted as "adjacent groups".

In the present disclosure, a direct linkage may mean a single bond.

In the present disclosure, a halogen atom may include a fluorine atom, a chlorine atom, a bromine atom, or an iodine atom.

In the present disclosure, the alkyl may have a linear, branched, or cyclic shape. The carbon number of the alkyl may be 1 to 30, 1 to 20, 1 to 15, 1 to 10, or 1 to 6. Examples of the alkyl may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldodecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyl eicosyl, 2-butyl eicosyl, 2-hexyl eicosyl, 2-octyl eicosyl, n-heneicosyl, n-docosyl, n-tricosyl, n-tetracosyl, n-pentacosyl, n-hexacosyl, n-heptacosyl, n-octacosyl, n-nonacosyl, n-triacontyl, etc., without limitation.

In the present disclosure, the aryl means an optional functional group or substituent derived from an aromatic hydrocarbon ring. The aryl may be monocyclic aryl or polycyclic aryl. The carbon number of the aryl for forming a ring may be 6 to 30, 6 to 20, or 6 to 15. Examples of the aryl may include phenyl, naphthyl, fluorenyl, anthracenyl, phenanthryl, biphenyl, terphenyl, quaterphenyl, quinquephenyl, sexiphenyl, triphenylenyl, pyrenyl, benzofluoranthenyl, chrysenyl, etc., without limitation.

In the present disclosure, the fluorenyl may be substituted, or two substituents may be combined with each other to form a spiro structure. For example, the fluorenyl may be 9,9'-spirobifluorenyl.

In the present disclosure, the heteroaryl may be heteroaryl including at least one of O, N, P, S, or Si as a heteroatom. The heteroaryl may be monocyclic heteroaryl or polycyclic heteroaryl. The carbon number of the heteroaryl for forming a ring may be 2 to 30, or 2 to 20. Examples of the heteroaryl may include thiophenyl, furanyl, pyrrolyl, imidazolyl, thiazolyl, oxazolyl, oxadiazolyl, triazolyl, pyridyl, bipyridyl, pyrimidyl, triazinyl, acridyl, pyridazinyl, pyrazinyl, quinolinyl, quinazolinyl, quinoxalinyl, phenoxazyl, phthalazinyl, pyrido pyrimidinyl, pyrido pyrazinyl, pyrazino pyrazinyl, isoquinolinyl, indolyl, carbazolyl, N-arylcarbazolyl, N-heteroaryl carbazolyl, N-alkyl carbazolyl, benzoxazolyl, benzoimidazolyl, benzothiazolyl, benzocarbazolyl, benzothiophenyl, dibenzothiophenyl, thienothiophenyl, benzofuranyl, phenanthroline, isooxazolyl, thiadiazolyl, phenothiazinyl, dibenzosilolyl, dibenzofuranyl, etc., without limitation.

In the present disclosure, the explanation on the aryl may be applied to the arylene, except that the arylene is divalent. The explanation on the heteroaryl may be applied to the heteroarylene, except that the heteroarylene is divalent.

In the present disclosure, the silyl may include alkyl silyl and aryl silyl. Examples of the silyl may include trimethylsilyl, triethylsilyl, t-butyl dimethylsilyl, vinyl dimethylsilyl, propyl dimethylsilyl, triphenylsilyl, diphenylsilyl, phenylsilyl, etc., without limitation.

In the present disclosure, the boron may include alkyl boron and aryl boron. Examples of the boron may include trimethyl boron, triethyl boron, t-butyl dimethyl boron, triphenyl boron, diphenyl boron, phenyl boron, etc., without limitation.

In the present disclosure, the alkenyl may be linear or branched. The carbon number is not specifically limited, however may be 2 to 30, 2 to 20, or 2 to 10. Examples of the alkenyl may include vinyl, 1-butenyl, 1-pentenyl, 1,3-butadienyl, styrenyl, styrylvinyl, etc., without limitation.

In the present disclosure, the carbon number of the amine is not specifically limited, however may be 1 to 30. The amine may include alkyl amine and aryl amine. Examples of the amine may include methylamine, dimethylamine, phenylamine, diphenylamine, naphthylamine, 9-methyl-anthracenylamine, triphenylamine, etc., without limitation.

Hereinafter, a monoamine compound according to an example embodiment will be explained.

In an example embodiment, the monoamine compound may be represented by the following Formula 1:

[Formula 1]

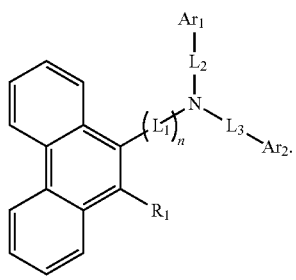

In Formula 1, $L_1$ may be a substituted or unsubstituted arylene group having 6 to 30 carbon atoms for forming a ring, or a substituted or unsubstituted heteroarylene group having 2 to 30 carbon atoms for forming a ring. $L_1$ may be a substituted or unsubstituted phenylene group. $L_1$ may be a substituted or unsubstituted divalent biphenyl group. $L_1$ may be a substituted or unsubstituted naphthylene group.

$L_1$ may be a substituted or unsubstituted arylene group having 6 to 15 carbon atoms for forming a ring.

$L_1$ may be an unsubstituted phenylene group. $L_1$ may be an m-phenylene group or a p-phenylene group. $L_1$ may be a monosubstituted phenylene group. For example, $L_1$ may be a phenylene group substituted with a phenyl group or a triphenylsilyl group.

$L_1$ may be an unsubstituted divalent biphenyl group. $L_1$ may be an unsubstituted naphthylene group.

Here, n is 1 or 2. In the case where n is 2, a plurality of $L_1$ may be the same or different.

$L_2$ and $L_3$ may be the same or different. $L_2$ and $L_3$ are each independently a direct linkage, a substituted or unsubstituted arylene group having 6 to 30 carbon atoms for forming a ring, or a substituted or unsubstituted heteroarylene group having 2 to 30 carbon atoms for forming a ring. $L_2$ and $L_3$ may each independently be a direct linkage, a substituted or unsubstituted phenylene group, or a substituted or unsubstituted divalent biphenyl group. $L_2$ and $L_3$ may each independently be a substituted or unsubstituted naphthylene group.

$L_2$ and $L_3$ may each independently be an unsubstituted divalent phenylene group. $L_2$ and $L_3$ may each independently be an m-phenylene group or a p-phenylene group. Each of $L_2$ and $L_3$ may be a monosubstituted phenylene group. Each of $L_2$ and $L_3$ may be a phenylene group substituted with an alkyl group having 1 to 10 carbon atoms or an aryl group having 6 to 30 carbon atoms. For example, each of $L_2$ and $L_3$ may be a phenylene group substituted with a methyl group or a phenyl group.

$L_2$ and $L_3$ may each independently be an unsubstituted divalent biphenyl group. $L_2$ and $L_3$ may each independently be an unsubstituted naphthylene group.

$R_1$ is an alkyl group having 1 to 10 carbon atoms, a substituted or unsubstituted aryl group having 6 to 30 carbon atoms for forming a ring, a substituted or unsubstituted heteroaryl group having 2 to 30 carbon atoms for forming a ring, or a substituted or unsubstituted aryl silyl group. $R_1$ may be a substituted or unsubstituted phenyl group, a substituted or unsubstituted naphthyl group, a substituted or unsubstituted biphenyl group, or a substituted or unsubstituted nitrogen-containing heteroaryl group. For example, $R_1$ may be a pyridinyl group or a triphenylsilyl group.

$R_1$ may be a monosubstituted phenyl group. $R_1$ may be a deuterium atom, a halogen atom, a cyano group, or a phenyl group substituted with an alkyl group having 1 to 10 carbon atoms. For example, $R_1$ may be a phenyl group substituted with a cyano group or an isopropyl group.

$Ar_1$ and $Ar_2$ may be the same or different. $Ar_1$ and $Ar_2$ are each independently a substituted or unsubstituted aryl group having 6 to 30 carbon atoms for forming a ring, or a substituted or unsubstituted heteroaryl group having 2 to 30 carbon atoms for forming a ring. $Ar_1$ and $Ar_2$ will be described in detail below.

In an example embodiment, in Formula 1, only the $R_1$ position in the illustrated phenanthryl group is substituted, and other positions are not substituted. In the case where a substituent is positioned at the other positions of the phenanthryl group, the energy levels of the HOMO and LUMO of the phenanthryl group may change due to the substituent, and hole transport properties may be deteriorated. In an example embodiment, in a monoamine compound in which only the $R_1$ position of the phenanthryl group is substituted, hole transport properties may be enhanced for use of the monoamine compound as a hole transport material.

In example embodiments, Formula 1 may be represented by the following Formula 2-1 or 2-2:

[Formula 2-1]

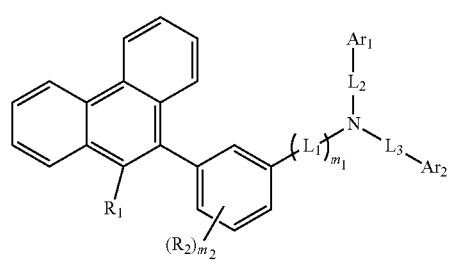

[Formula 2-2]

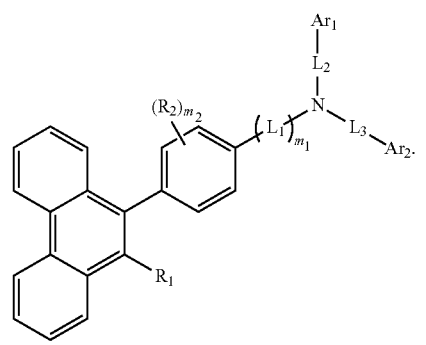

Here, $m_1$ may be 0 or 1, and $m_2$ may be an integer of 0 to 2.

$R_2$ may be a hydrogen atom, a deuterium atom, a substituted or unsubstituted alkyl group having 1 to 10 carbon atoms, a substituted or unsubstituted aryl group having 6 to 30 carbon atoms for forming a ring, a substituted or unsubstituted heteroaryl group having 2 to 30 carbon atoms for forming a ring, or a substituted or unsubstituted aryl silyl group. For example, $R_2$ may be a hydrogen atom, an unsubstituted phenyl group, or a triphenylsilyl group.

In the case where $m_2$ is 2, a plurality of $R_2$ may be the same or different. $R_2$ may be combined with an adjacent group to form a ring. For example, $R_2$ may be combined with an adjacent group to form a substituted or unsubstituted hydrocarbon ring, or a substituted or unsubstituted heterocycle. $R_2$ may be combined with an adjacent group to form a substituted or unsubstituted aromatic hydrocarbon ring.

In Formulae 2-1 and 2-2, the particular explanation on $Ar_1$, $Ar_2$, $L_1$, $L_2$, $L_3$, and $R_1$ is the same as the explanation referring to Formula 1 and will not be repeated.

Formula 2-1 may be represented by one of the following Formulae 2-1-1 to 2-1-3:

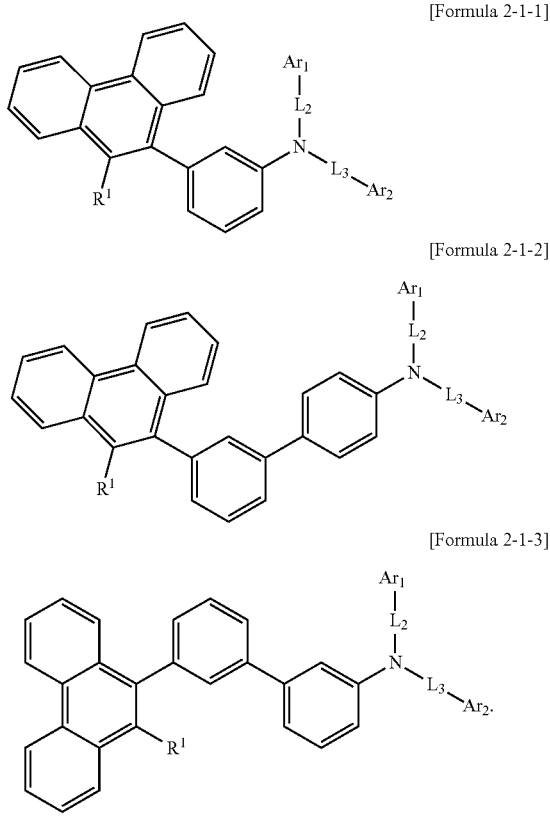

[Formula 2-1-1]

[Formula 2-1-2]

[Formula 2-1-3]

In Formulae 2-1-1 to 2-1-3, $Ar_1$, $Ar_2$, $L_2$, $L_3$, and $R_1$ are the same as defined in Formula 1.

In Formulae 2-1-1 to 2-1-3, $R_1$ may be a substituted or unsubstituted phenyl group, $L_3$ may be a substituted or unsubstituted phenylene group, and $Ar_2$ may be a substituted or unsubstituted naphthyl group. More specifically, the monoamine compound may be represented by the following Formula 2-1-1, $R_1$ may be a substituted or unsubstituted phenyl group, $L_3$ may be a substituted or unsubstituted phenylene group, and $Ar_2$ may be a substituted or unsubstituted naphthyl group. In case $Ar_2$ is a substituted or unsubstituted naphthyl group, $L_3$ may be connected at the carbon of position 1 of the naphthyl group.

In Formulae 2-1-1 to 2-1-3, $L_2$ may be a substituted or unsubstituted phenylene group, and $Ar_1$ may be a substituted or unsubstituted phenyl group. More specifically, the monoamine compound may be represented by the following Formula 2-1-1, $R_1$ may be a substituted or unsubstituted phenyl group, $L_3$ may be a substituted or unsubstituted phenylene group, $Ar_2$ may be a substituted or unsubstituted naphthyl group, $L_2$ may be a substituted or unsubstituted phenylene group, and $Ar_1$ may be a substituted or unsubstituted phenyl group.

In Formulae 2-1-1 to 2-1-3, $L_2$ may be a direct linkage, and $Ar_1$ may be a substituted or unsubstituted dibenzofuranyl group. More specifically, the monoamine compound may be represented by the following Formula 2-1-1, $R_1$ may be a substituted or unsubstituted phenyl group, $L_3$ may be a substituted or unsubstituted phenylene group, $Ar_2$ may be a substituted or unsubstituted naphthyl group, $L_2$ may be a direct linkage, and $Ar_1$ may be a substituted or unsubstituted dibenzofuranyl group.

Formula 2-2 may be represented by one of the following Formulae 2-2-1 to 2-2-3:

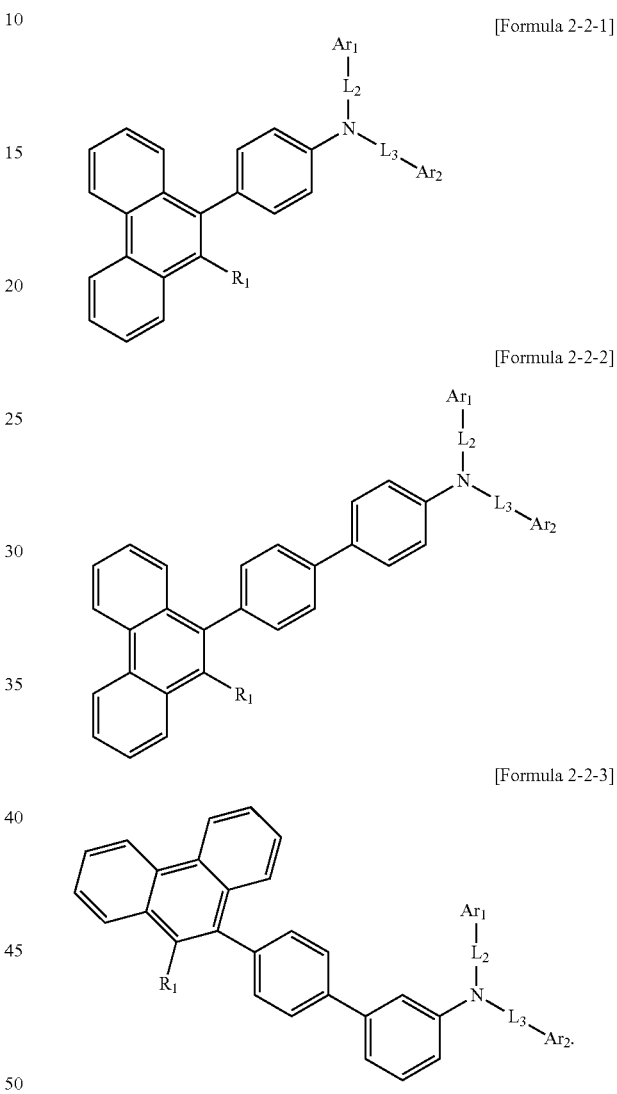

[Formula 2-2-1]

[Formula 2-2-2]

[Formula 2-2-3]

In Formulae 2-2-1 to 2-2-3, $Ar_1$, $Ar_2$, $L_2$, $L_3$, and $R_1$ are the same as defined in Formula 1.

In Formula 1, $Ar_1$ and $Ar_2$ may be each independently a substituted or unsubstituted phenyl group. $Ar_1$ and $Ar_2$ may each independently be a mono- or di-substituted phenyl group. $Ar_1$ and $Ar_2$ may each independently be a phenyl group substituted with a deuterium atom, a halogen atom, a cyano group, or an alkyl group having 1 to 10 carbon atoms. For example, $Ar_1$ and $Ar_2$ may each independently be a phenyl group substituted with a fluorine atom or a substituted or unsubstituted octyl group.

$Ar_1$ and $Ar_2$ may each independently be a substituted or unsubstituted biphenyl group. $Ar_1$ and $Ar_2$ may each independently be a substituted or unsubstituted terphenyl group. $Ar_1$ and $Ar_2$ may each independently be a substituted or unsubstituted naphthyl group. $Ar_1$ and $Ar_2$ may each independently be a substituted or unsubstituted phenanthryl group.

$Ar_1$ and $Ar_2$ may each independently be a substituted or unsubstituted fluorenyl group. $Ar_1$ and $Ar_2$ may each independently be a disubstituted fluorenyl group. For example, $Ar_1$ and $Ar_2$ may each independently be a fluorenyl group substituted with an aryl group.

$Ar_1$ and $Ar_2$ may each independently be a substituted or unsubstituted dibenzofuranyl group. $Ar_1$ and $Ar_2$ may each independently be a monosubstituted dibenzofuranyl group. $Ar_1$ and $Ar_2$ may each independently be a dibenzofuranyl group substituted with an alkyl group having 1 to 10 carbon atoms, a substituted or unsubstituted aryl group having 6 to 30 carbon atoms for forming a ring, or a substituted or unsubstituted heteroaryl group having 2 to 30 carbon atoms for forming a ring. For example, $Ar_1$ and $Ar_2$ may each independently be a dibenzofuranyl group substituted with a phenyl group or a cyclohexyl group.

$Ar_1$ and $Ar_2$ may each independently be a substituted or unsubstituted dibenzothiophenyl group. $Ar_1$ and $Ar_2$ may each independently be a substituted or unsubstituted benzonaphthofuranyl group. $Ar_1$ and $Ar_2$ may each independently be a substituted or unsubstituted benzonaphthothiophenyl group.

$Ar_1$ and $Ar_2$ may each independently be represented by the following Formula 3:

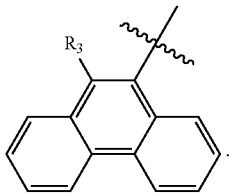

[Formula 3]

$R_3$ may be an alkyl group having 1 to 10 carbon atoms, a substituted or unsubstituted aryl group having 6 to 30 carbon atoms for forming a ring, a substituted or unsubstituted heteroaryl group having 2 to 30 carbon atoms for forming a ring, or a substituted or unsubstituted aryl silyl group, and

indicates bonding to an adjacent moiety.

In the case where $Ar_1$ and $Ar_2$ are each independently represented by Formula 3, in formula 1, $L_2$ and $L_3$ may each independently be a substituted or unsubstituted arylene group having 6 to 30 carbon atoms for forming a ring, or a substituted or unsubstituted heteroarylene group having 2 to 30 carbon atoms for forming a ring.

In the case where $Ar_1$ and $Ar_2$ are each independently represented by Formula 3, in formula 1, $L_2$ and $L_3$ may each independently be a substituted or unsubstituted phenylene group or a substituted or unsubstituted divalent biphenyl group. $L_2$ and $L_3$ may each independently be an unsubstituted phenylene group.

$Ar_1$ and $Ar_2$ may be represented by the following Formula 4:

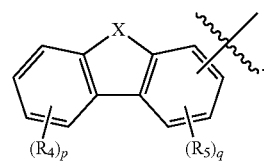

[Formula 4]

X may be O or S.

$R_4$ and $R_5$ may each independently be a hydrogen atom, a deuterium atom, a substituted or unsubstituted alkyl group having 1 to 10 carbon atoms, a substituted or unsubstituted aryl group having 6 to 30 carbon atoms for forming a ring, a substituted or unsubstituted heteroaryl group having 2 to 30 carbon atoms for forming a ring, or a substituted or unsubstituted aryl silyl group. $R_4$ and $R_5$ may each independently be a cycloalkyl group. For example, $R_4$ and $R_5$ may each independently be a cyclohexyl group.

"p" may be an integer of 0 to 4. "q" may be and integer of 0 to 3. In the case where "p" is an integer of 2 or more, a plurality of $R_4$ may be the same or different. In the case where "q" is an integer of 2 or more, a plurality of $R_5$ may be the same or different. In the case where "p" and "q" are each independently an integer of 2 or more, $R_4$ and $R_5$ may each independently be combined with an adjacent group to form a ring. For example, in the case where at least one of $R_4$ and $R_5$ forms an aromatic ring, $Ar_1$ and $Ar_2$ may be a heteroaryl group having four or five rings.

The monoamine compound represented by Formula 1 may be at least one selected from the monoamine compounds represented in the following Compound Group 1. However, an example embodiment is not limited thereto.

[Compound Group 1]

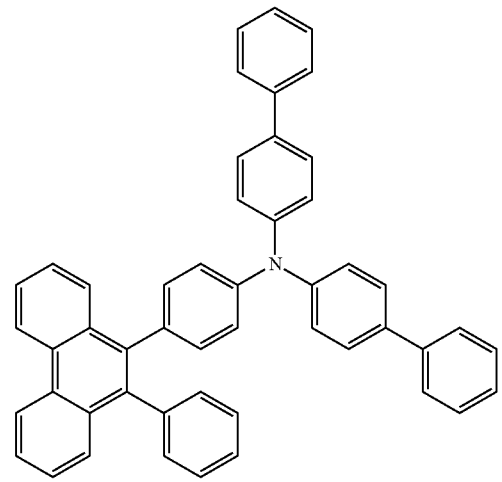

1

2
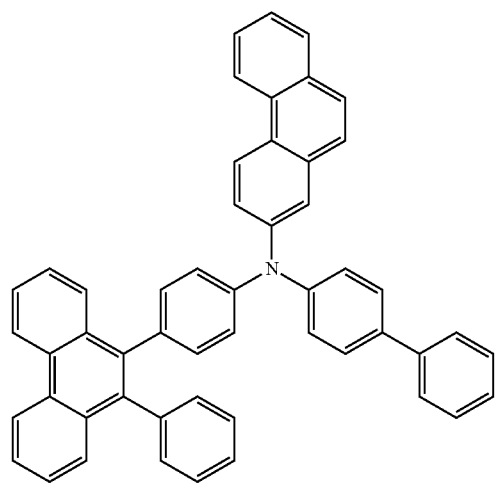
3
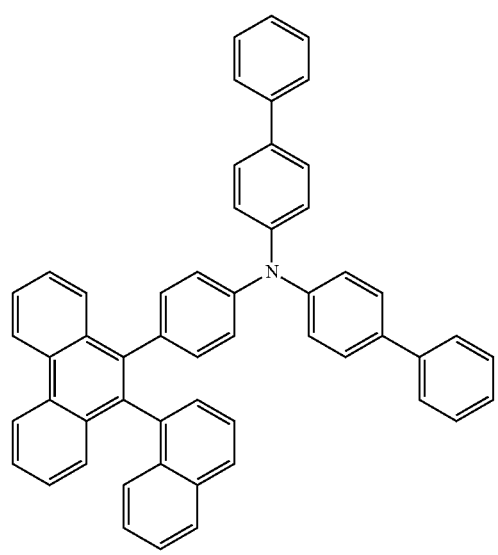
4
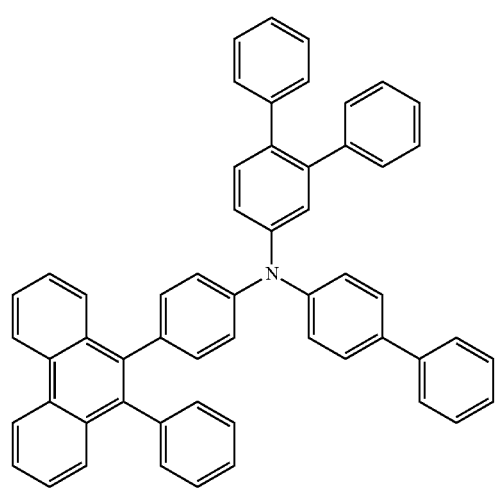
5
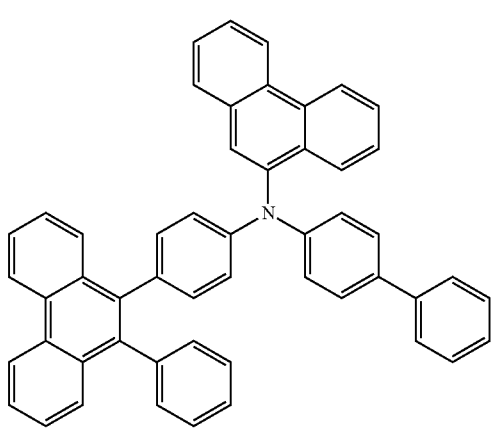
6
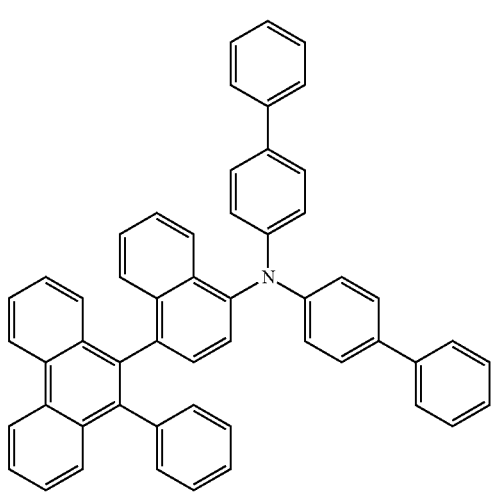
7
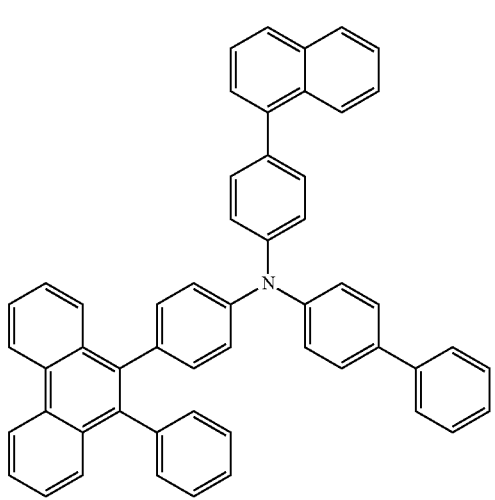

8
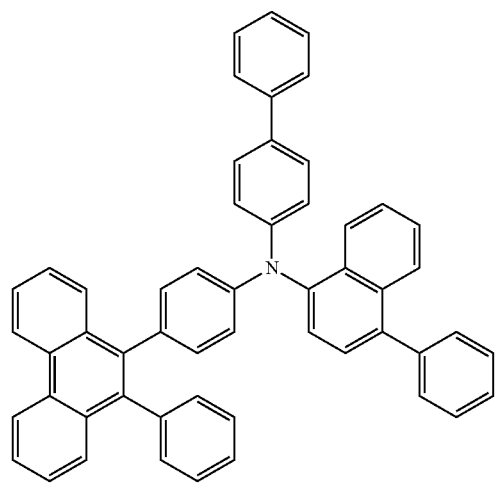
9
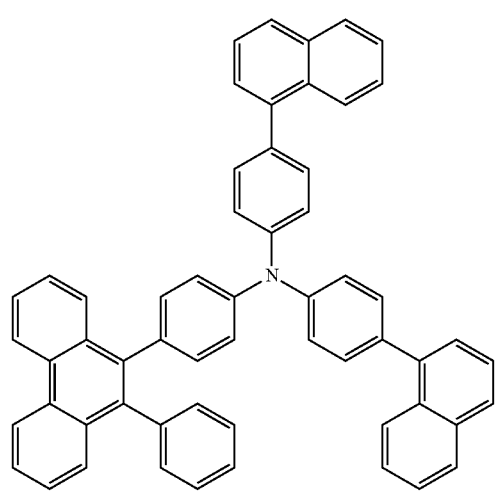
10
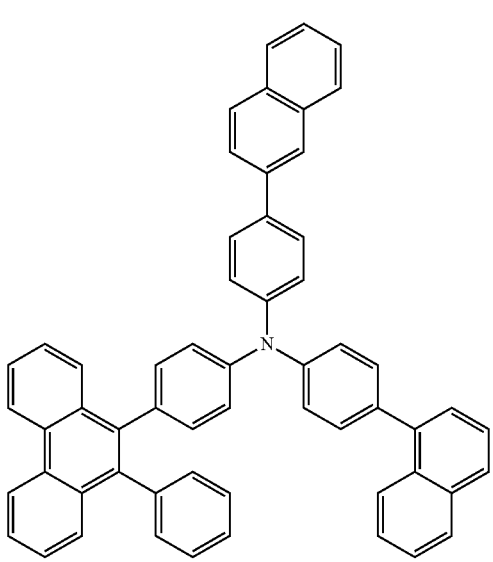
11
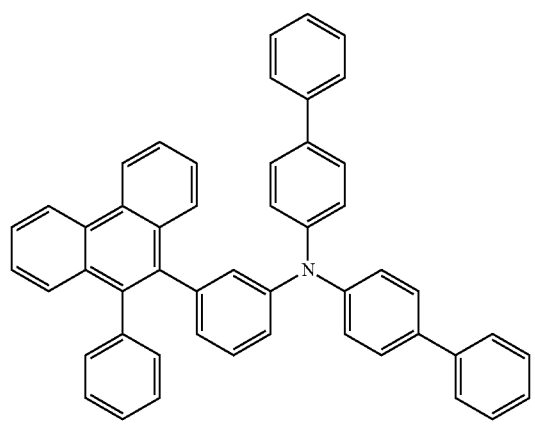
12
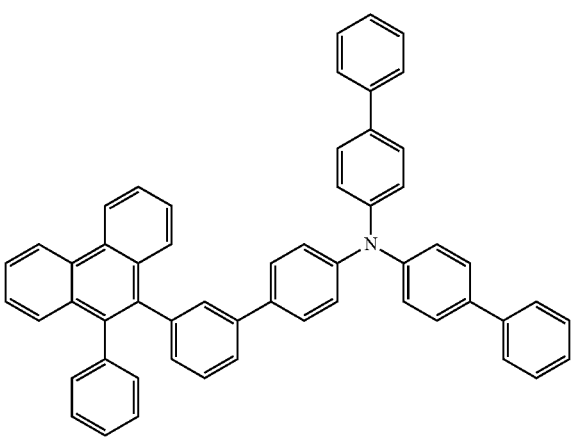
13
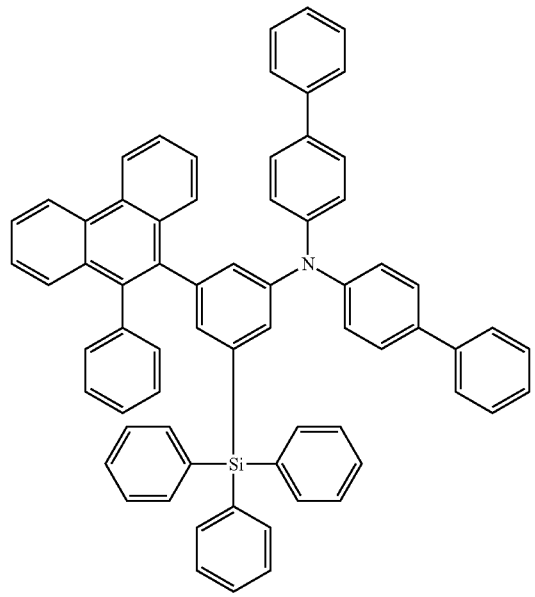

14
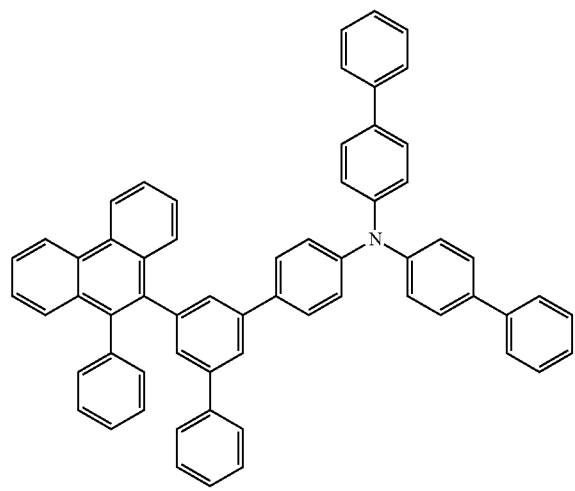
15
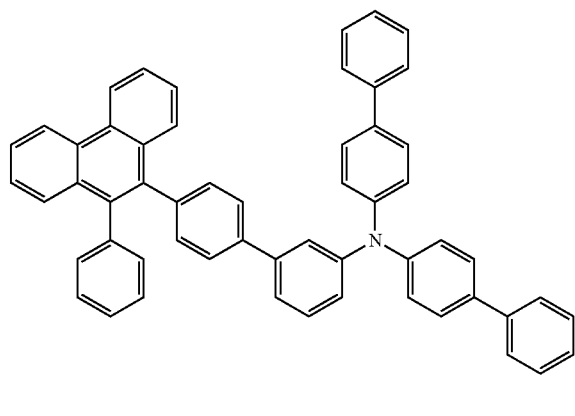
16
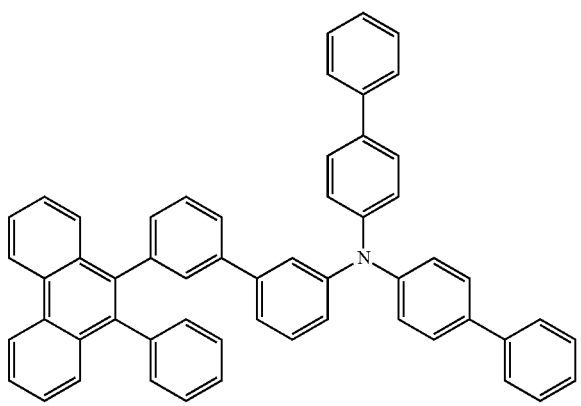
17
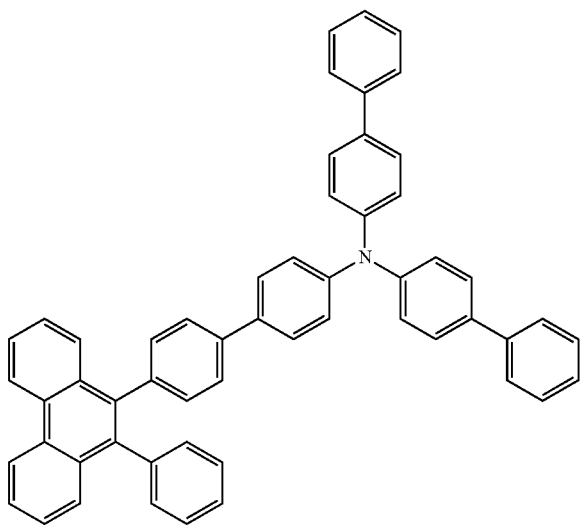
18
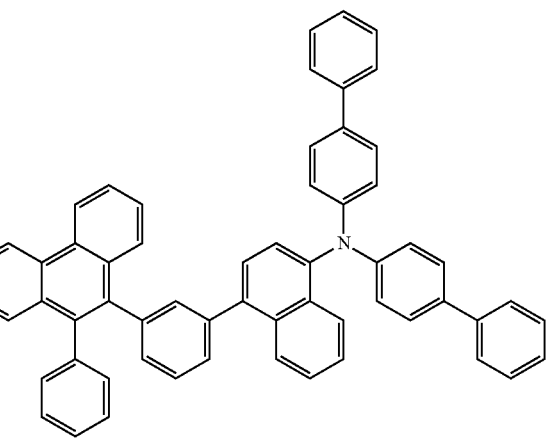
19
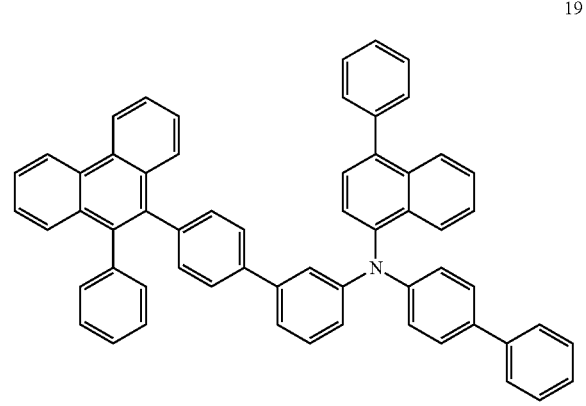

20
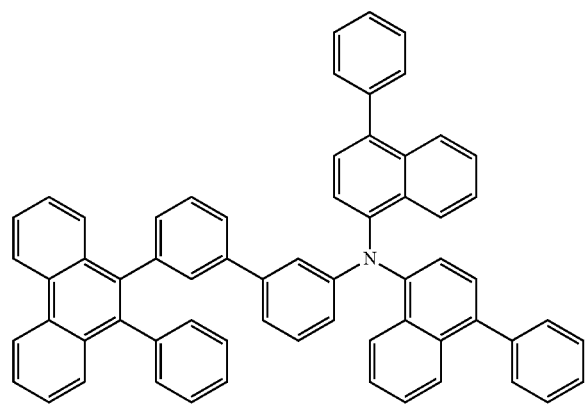
21
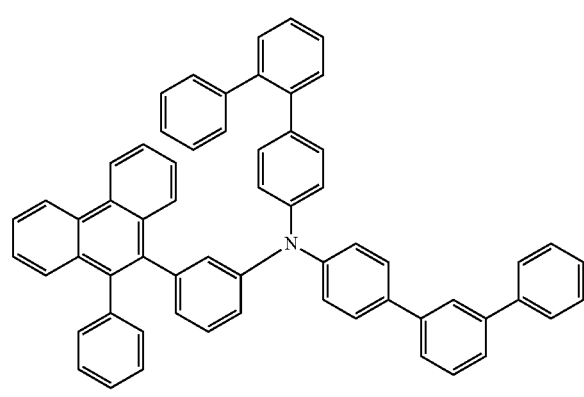
22
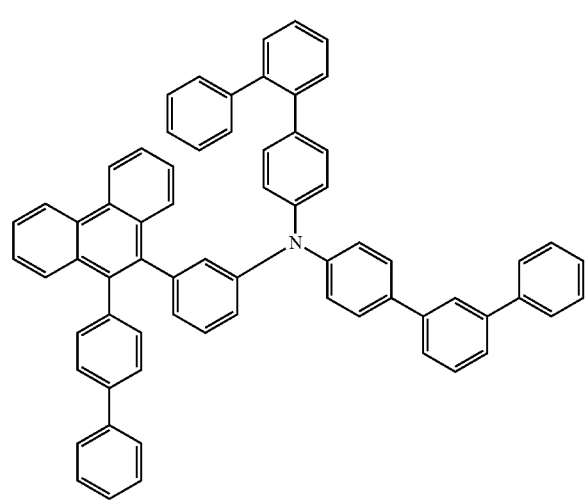
23
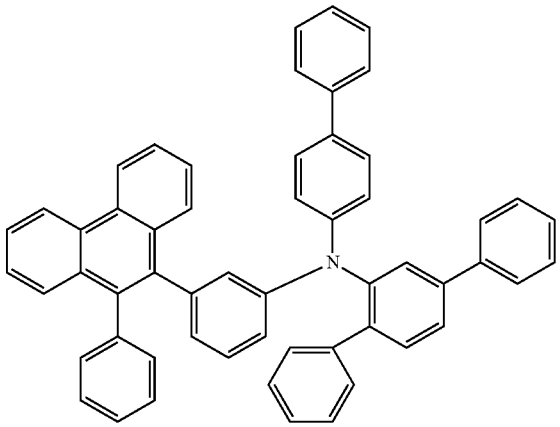
24
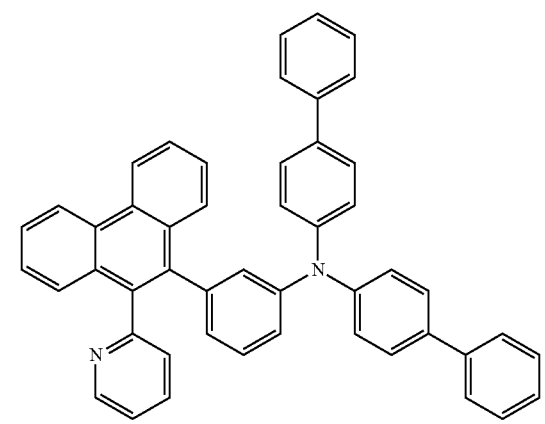
25
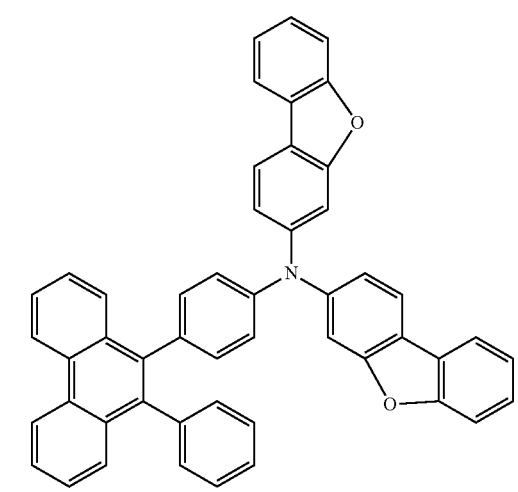

26
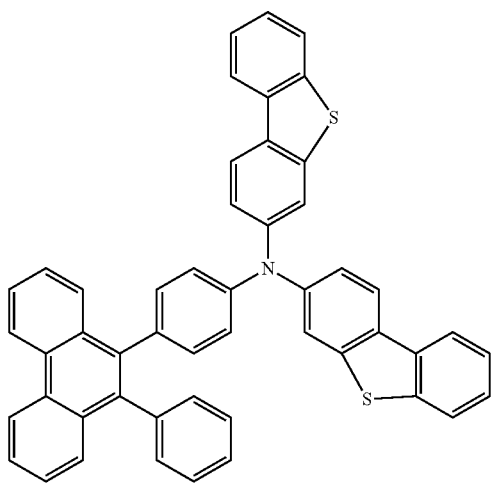
27
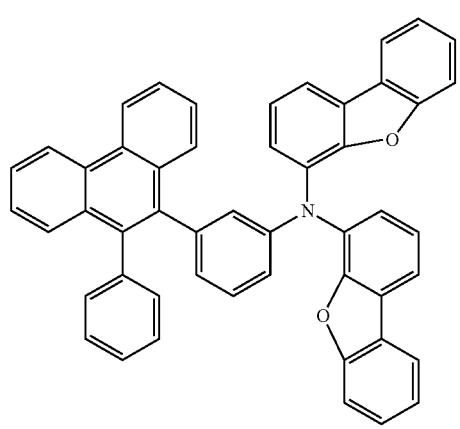
28
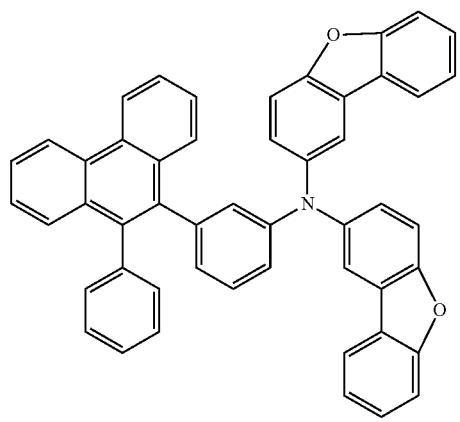
29
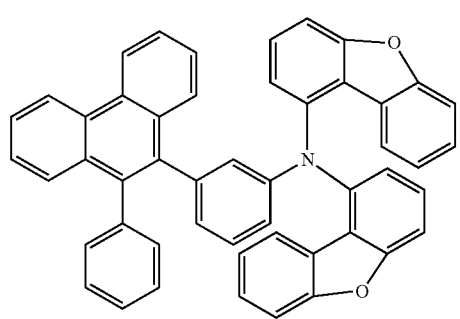
30
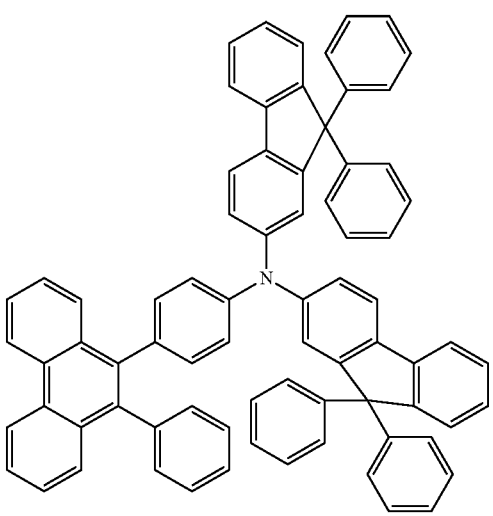
31
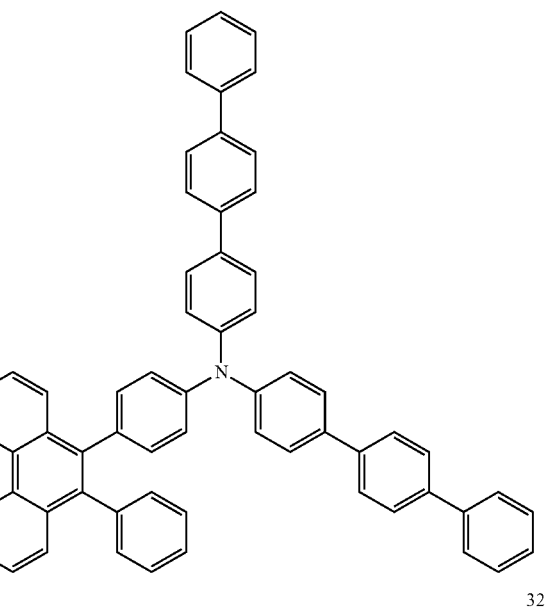
32

33
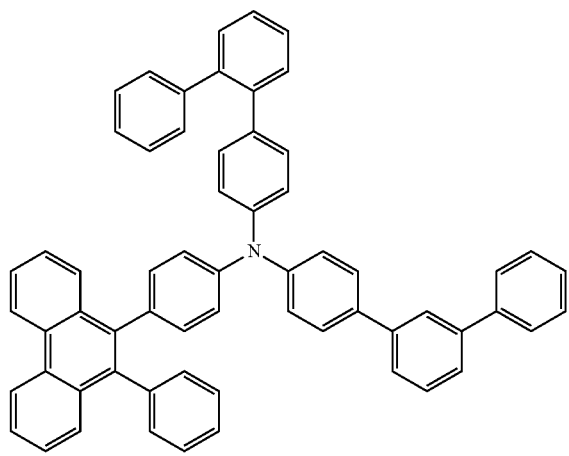
34
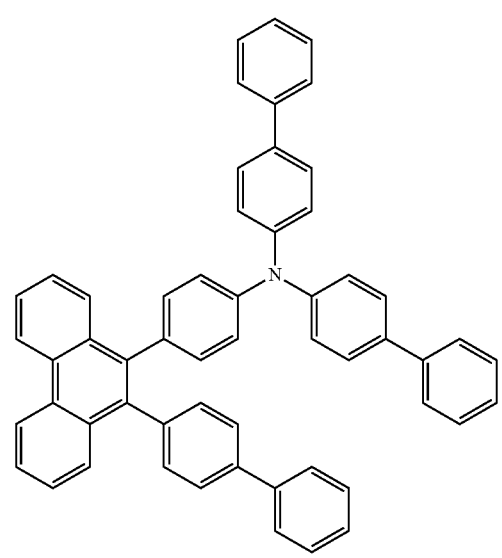
35
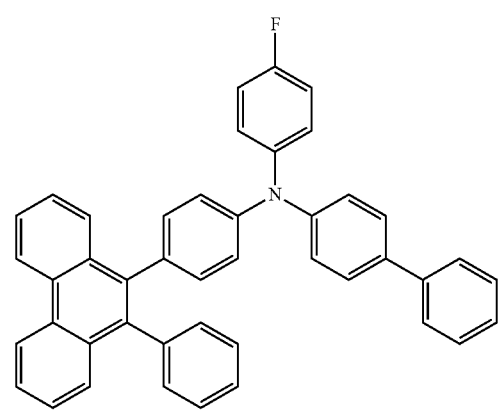
36
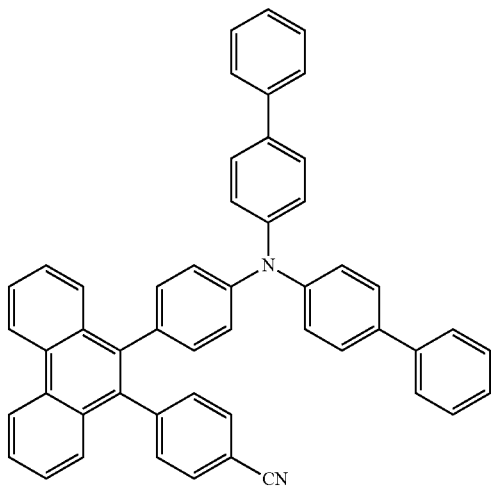
37
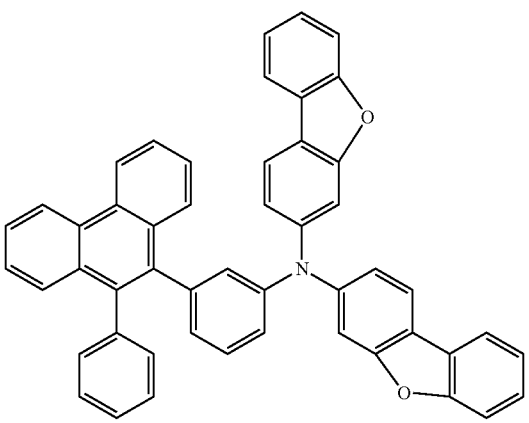
38
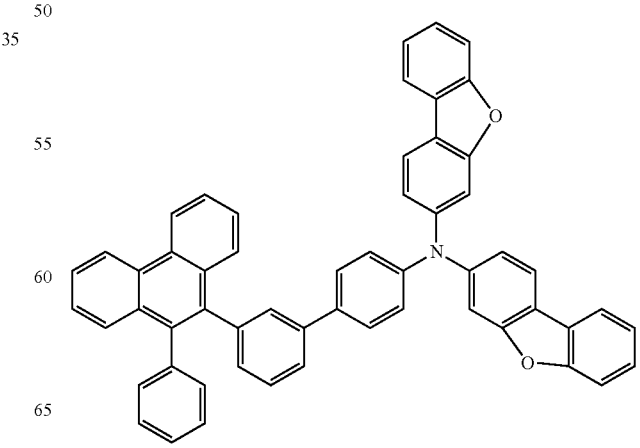

39
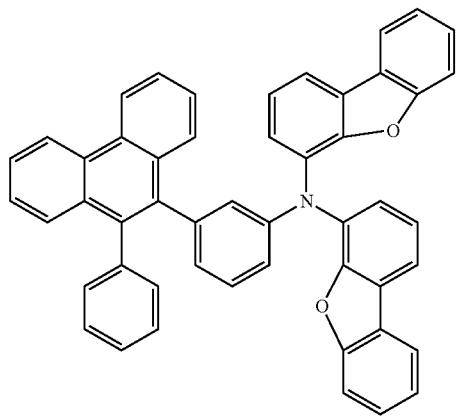
40
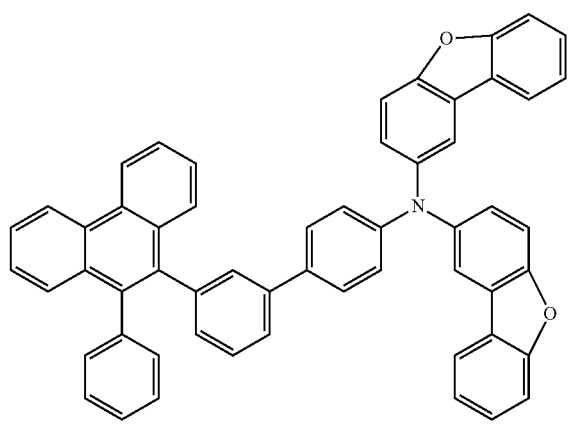
41
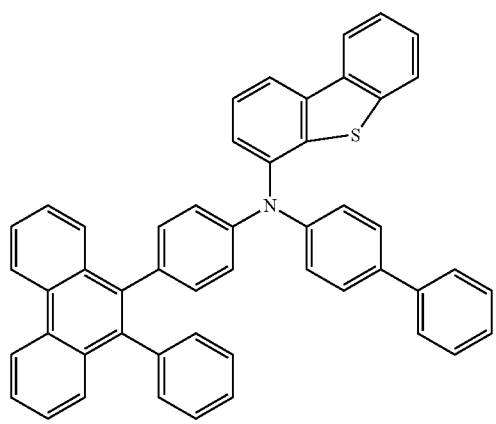
42
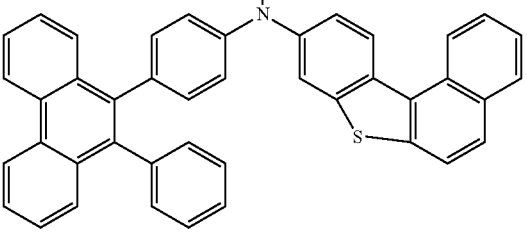
43
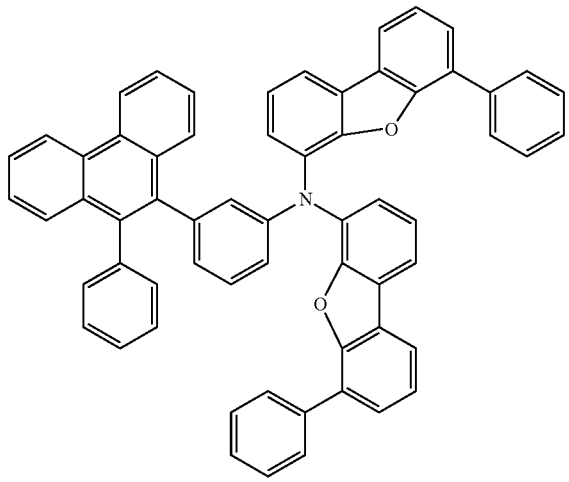
44
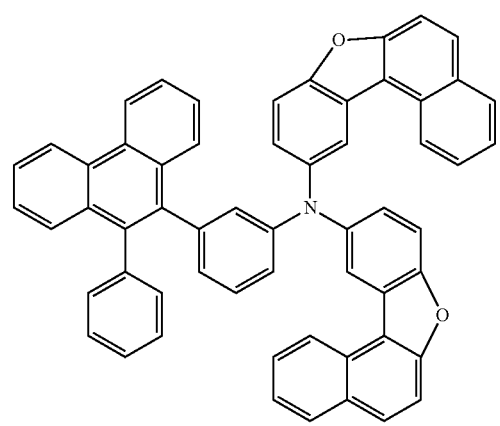

45
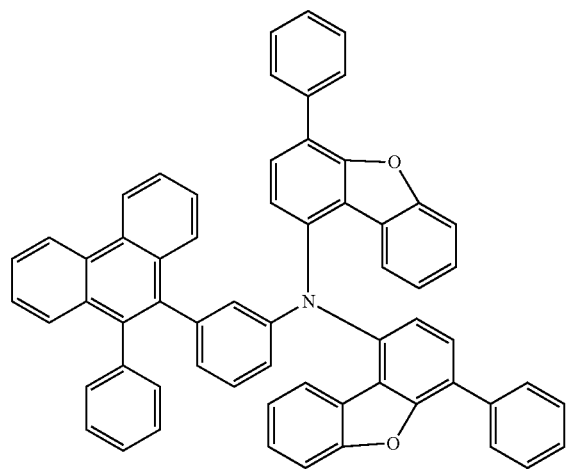
46
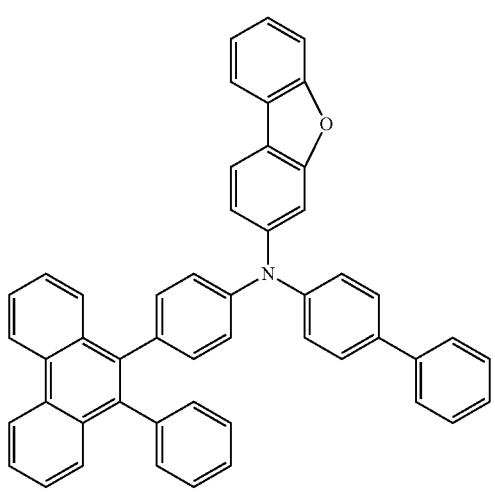
47
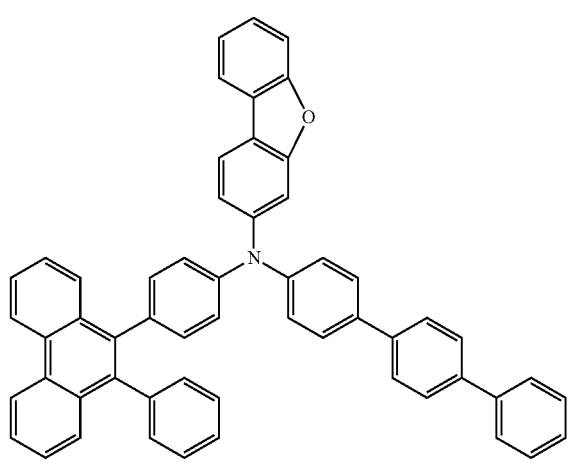
48
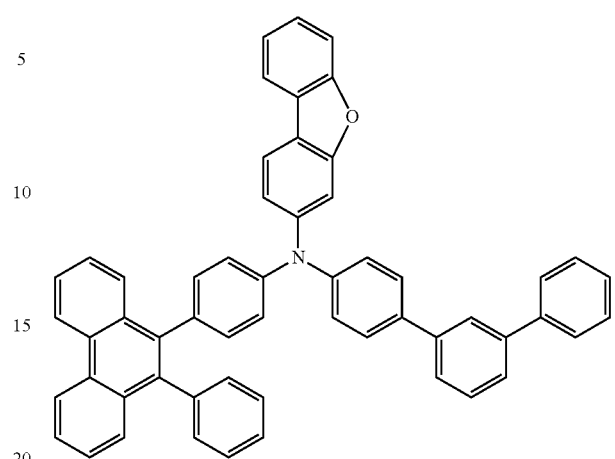
49
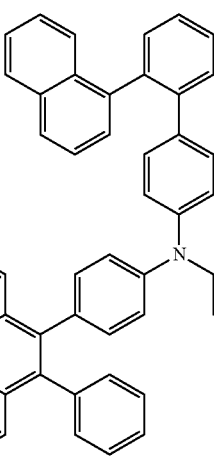
50
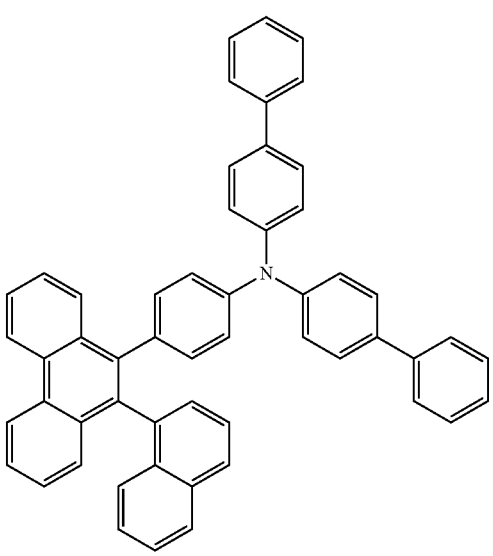

51
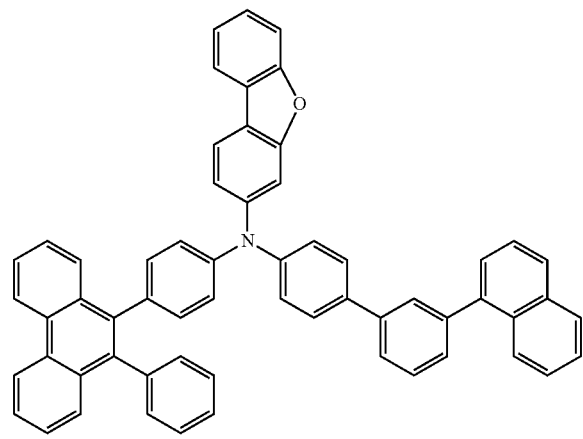
52
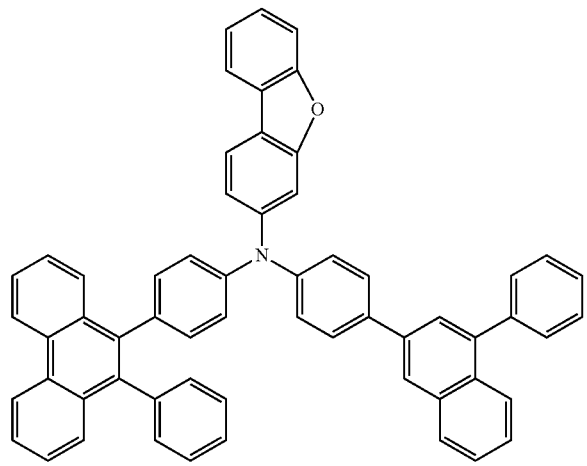
53
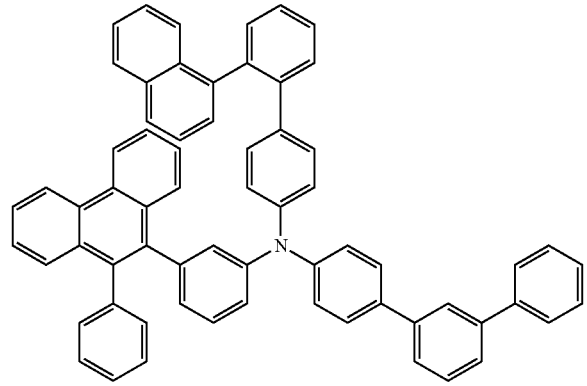
54
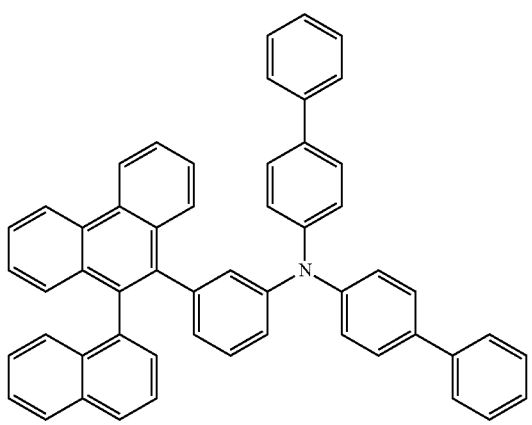
55
56
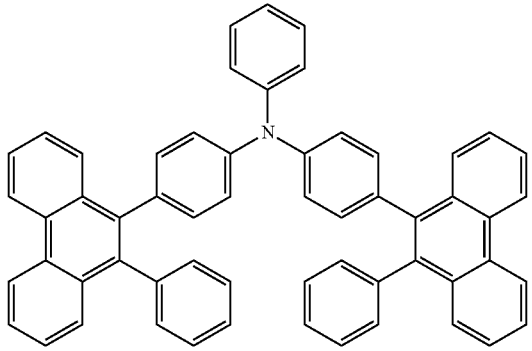

57
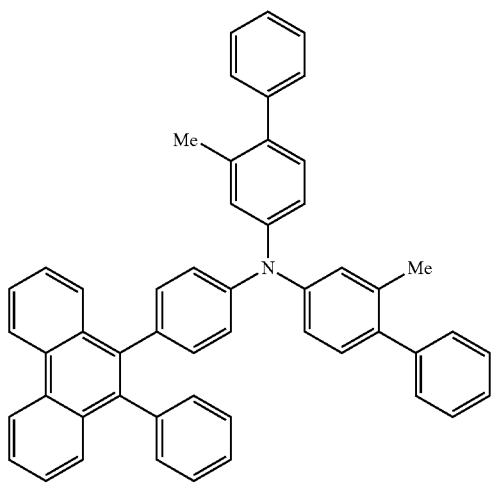
58
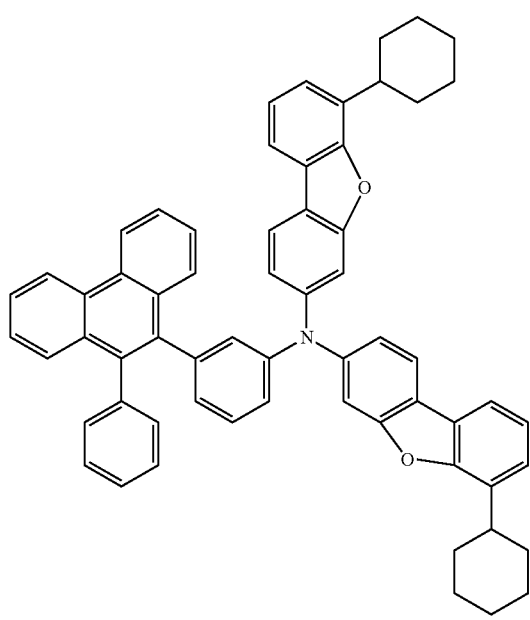
59
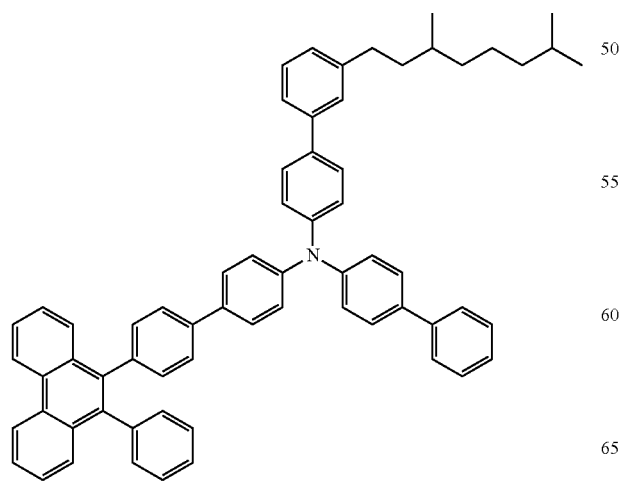
60
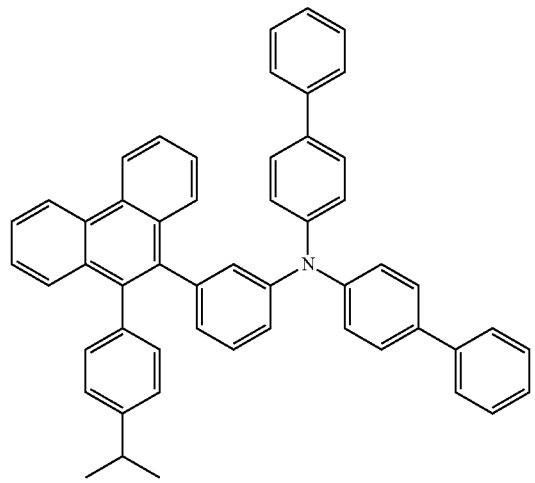
61
62
63

64
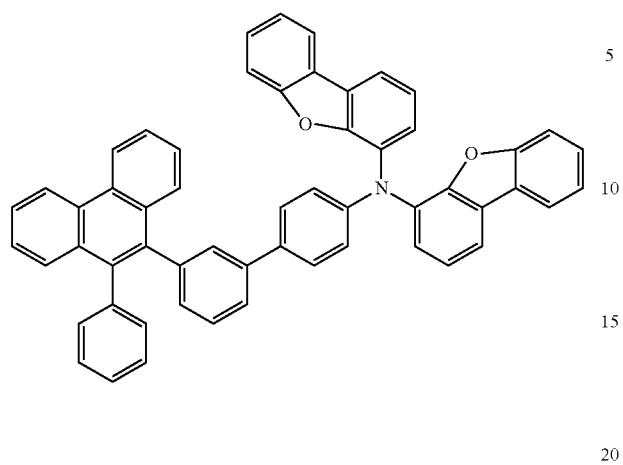
65
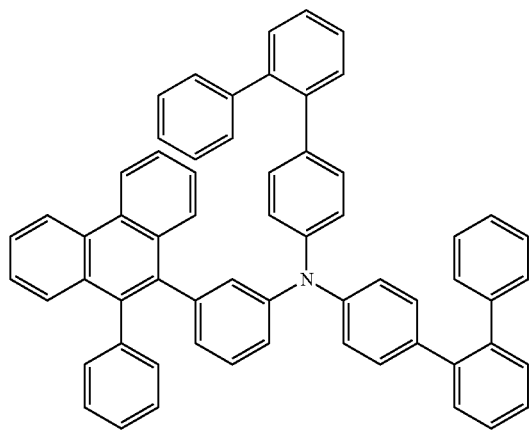
66
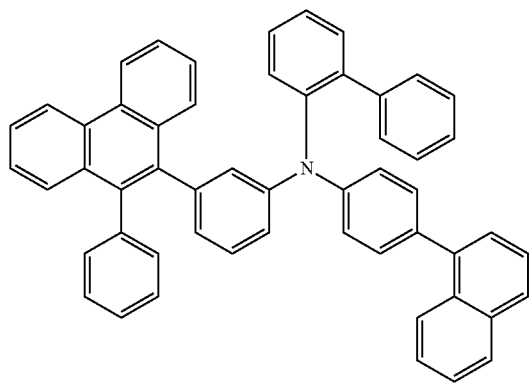
67
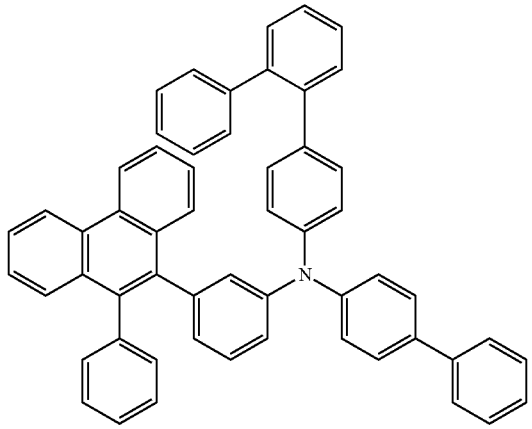
68
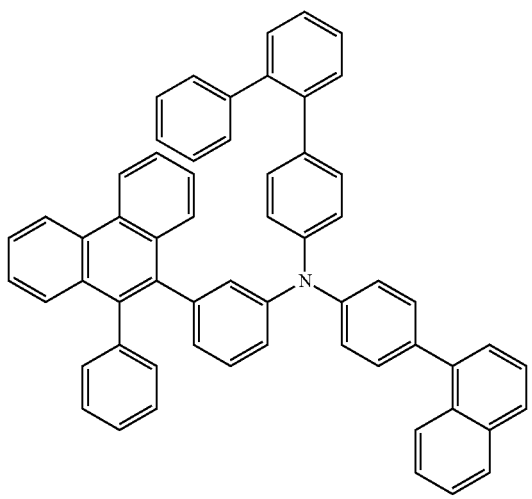
69
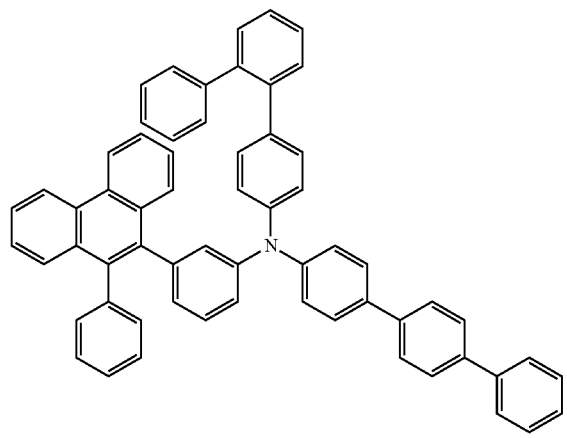

70
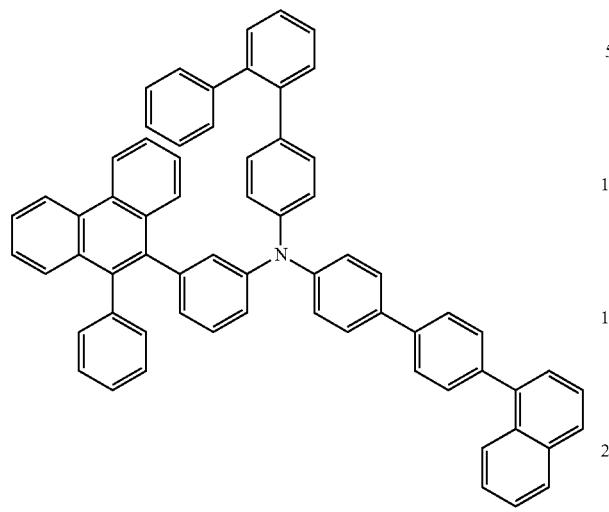
71
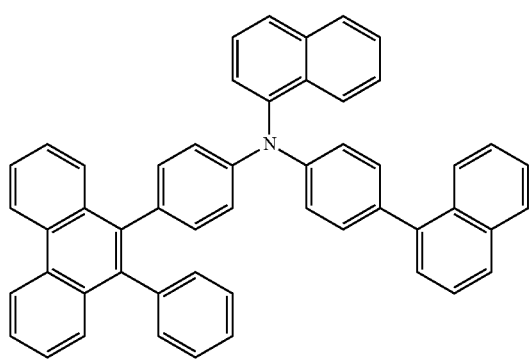
72
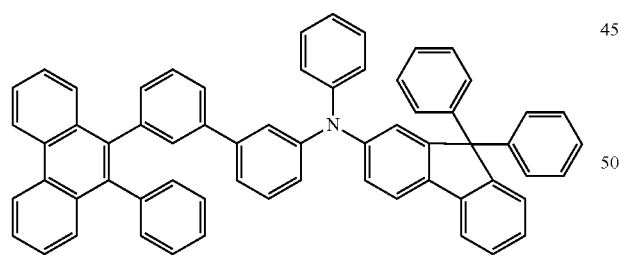
73
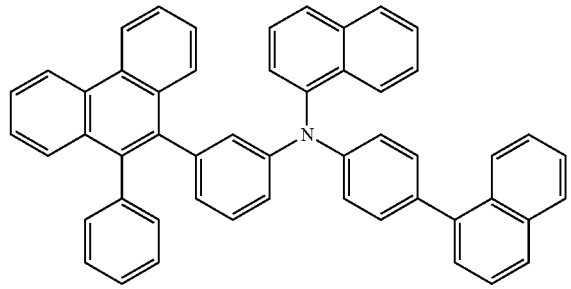
74
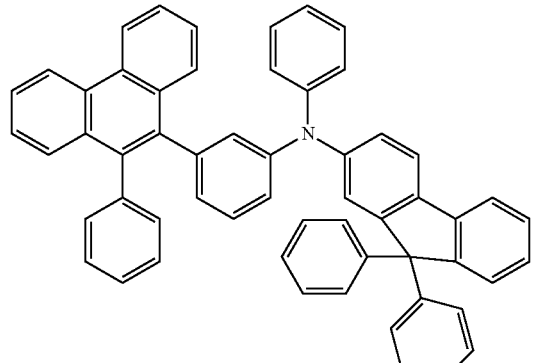
75
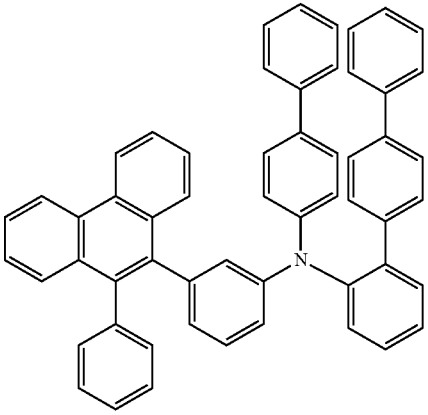
76
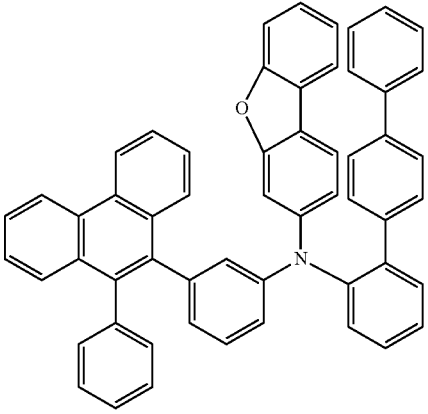
77
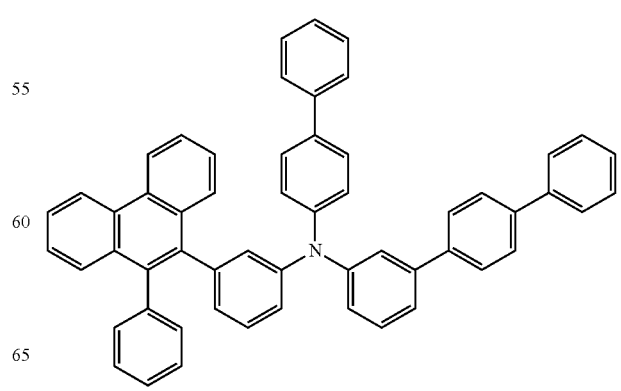

78
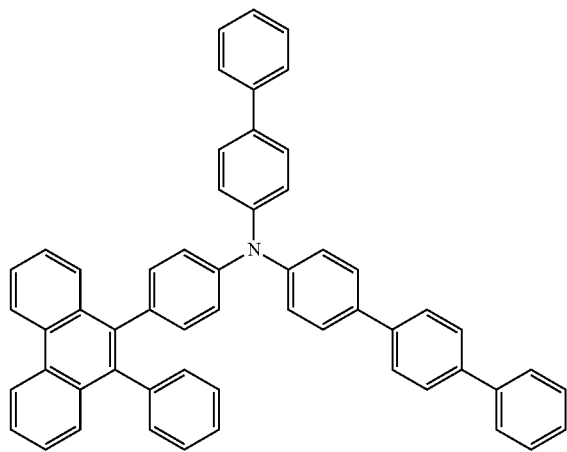
79
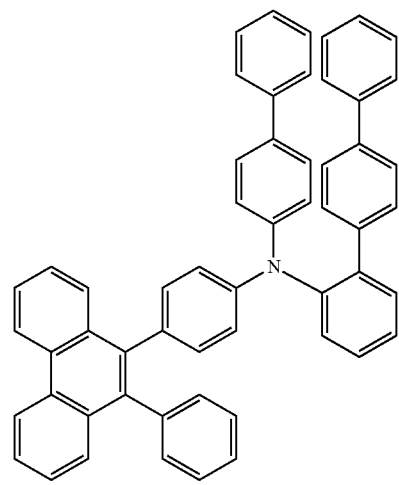
80
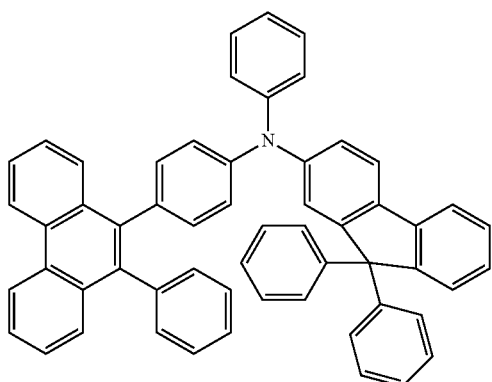
81
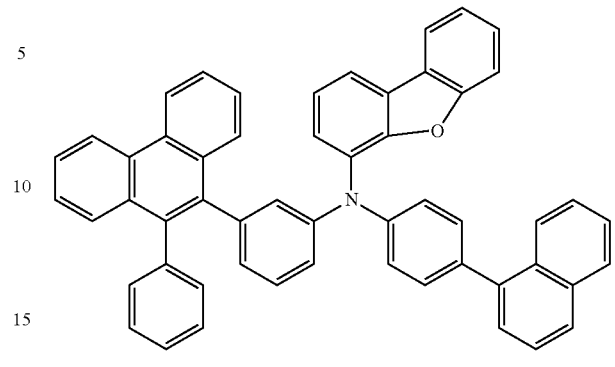
82
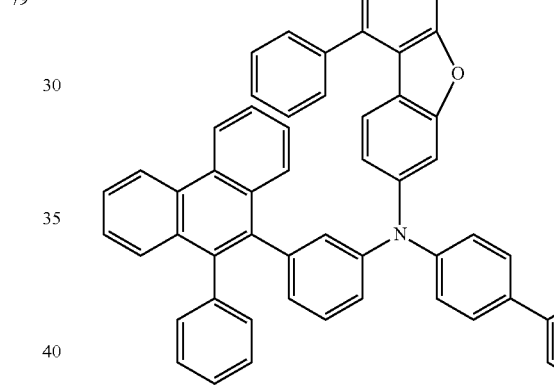
83
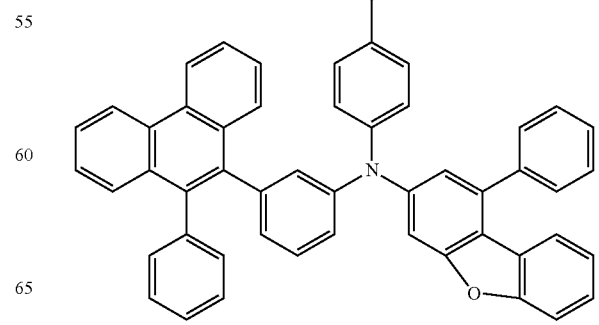

84
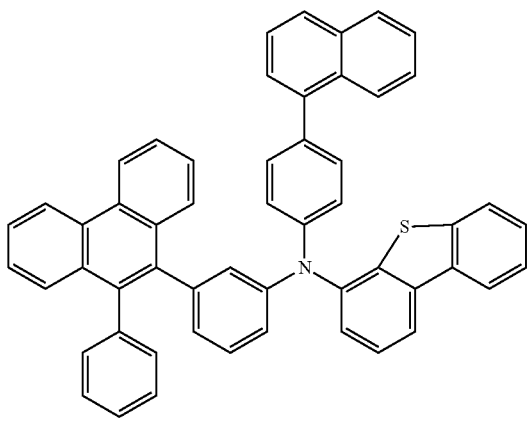
85
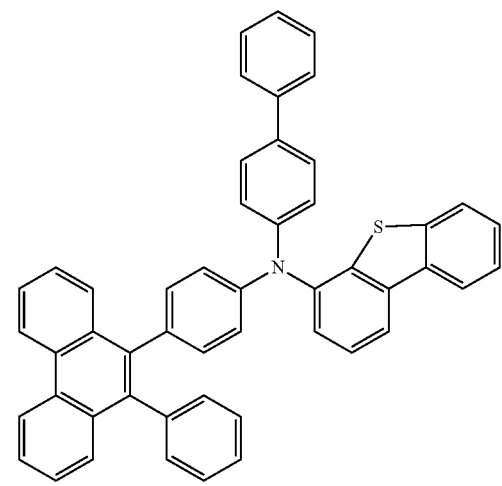
86
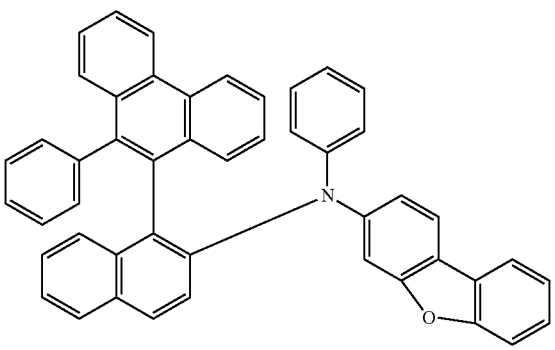
87
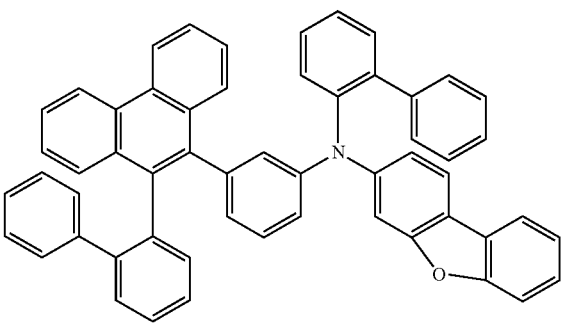
88
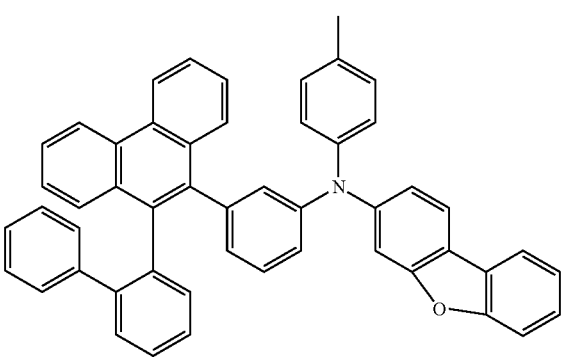
89
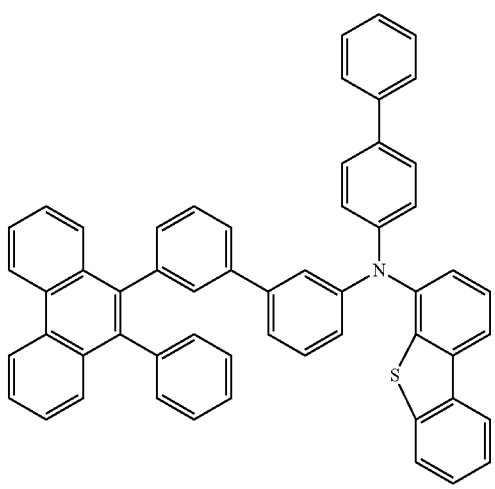
90
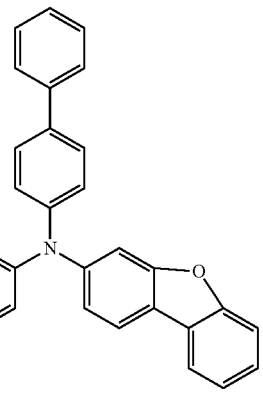

91
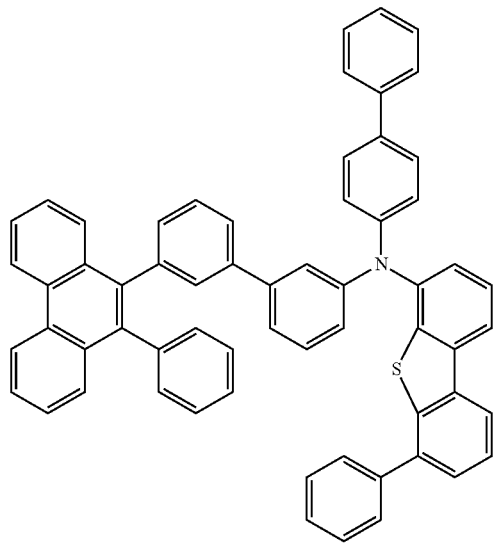
92
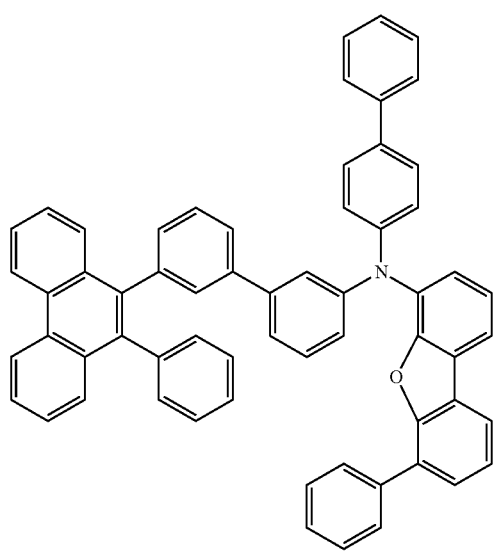
93
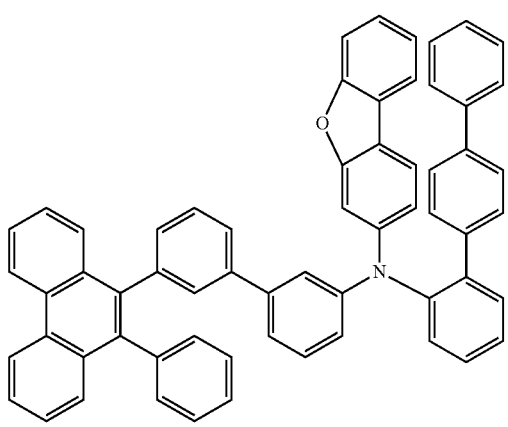
94
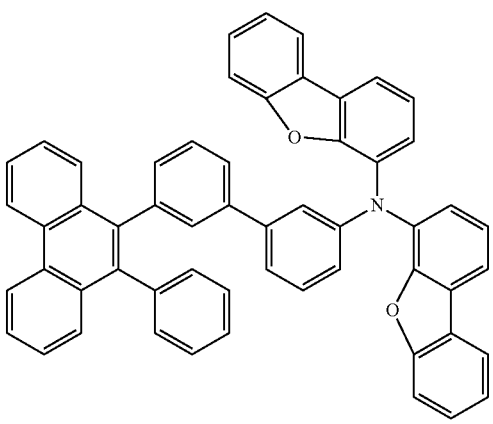
95
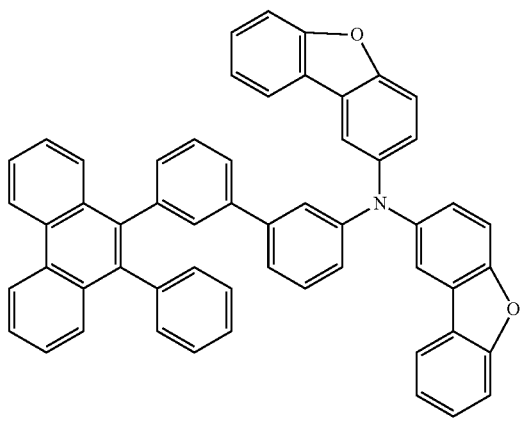
96
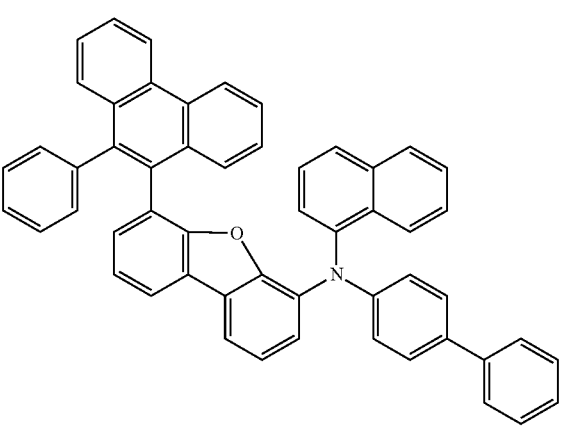

97
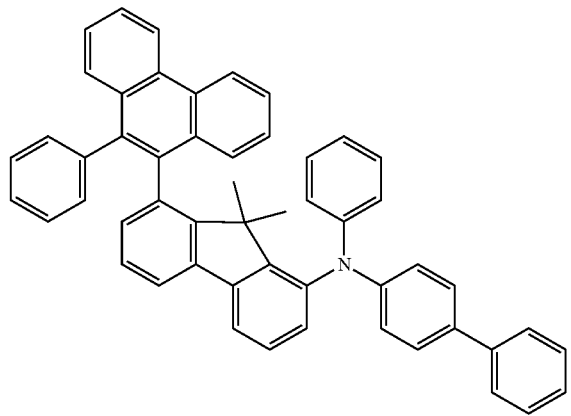
98
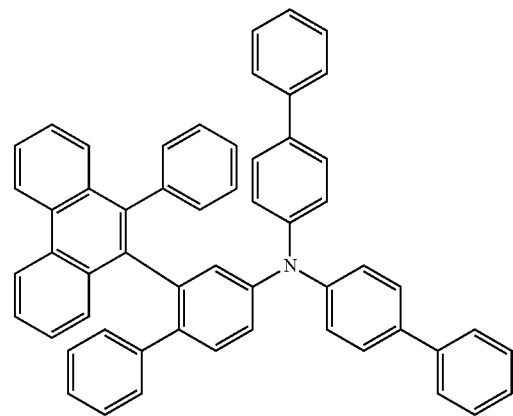
99
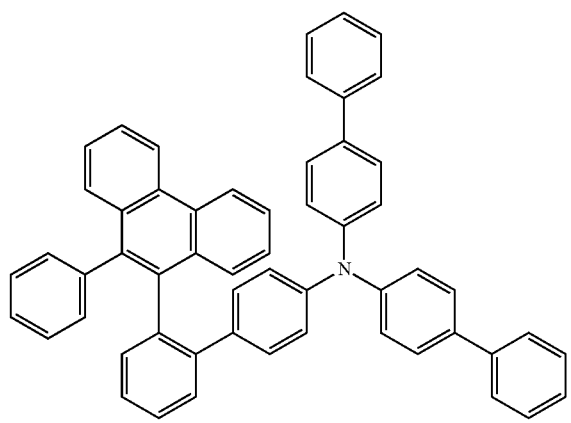
100
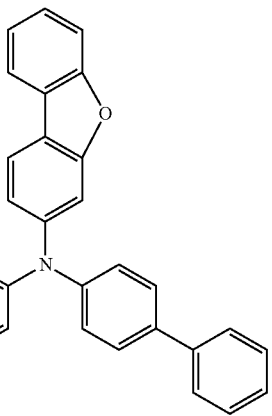
101
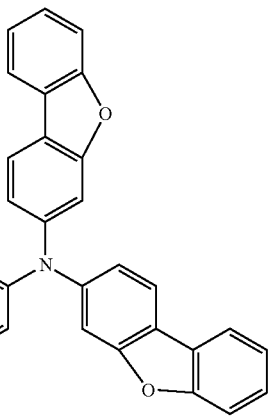
102
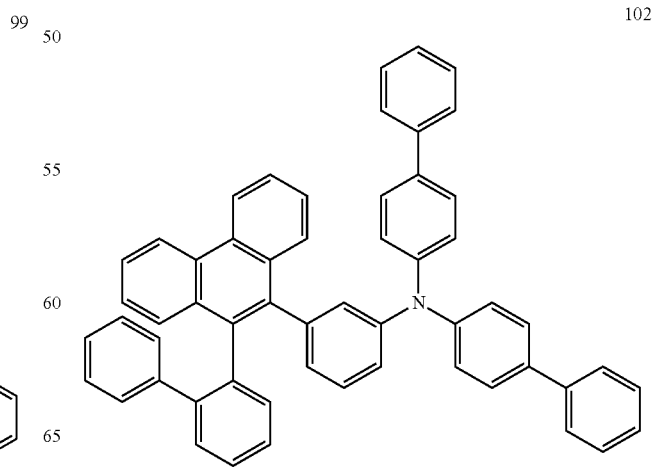

103
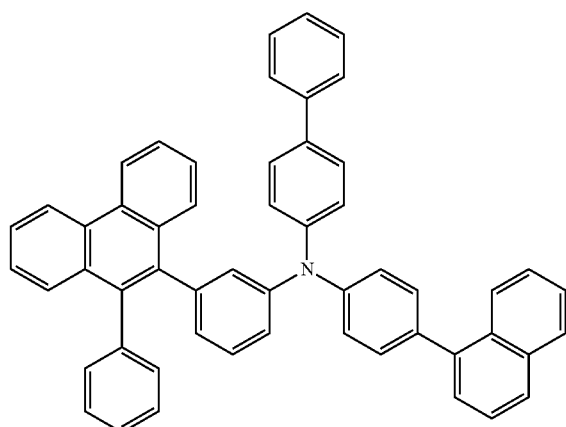
104
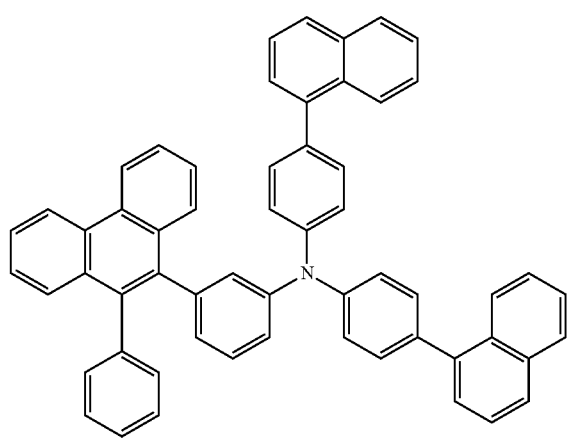
105
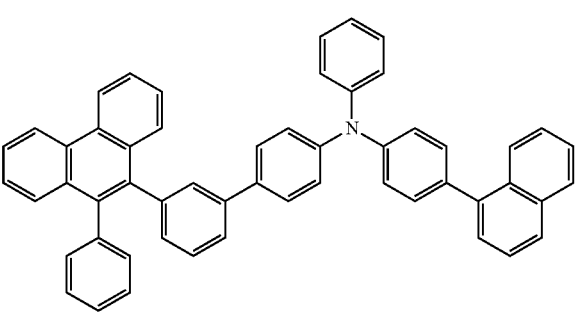
106
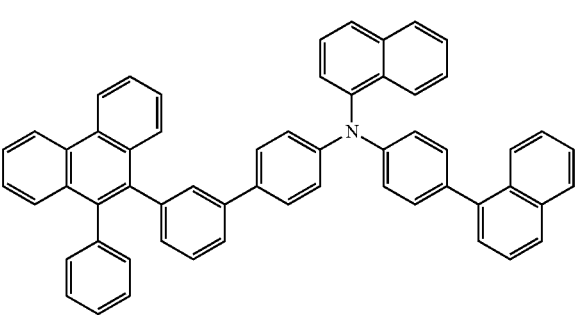
107
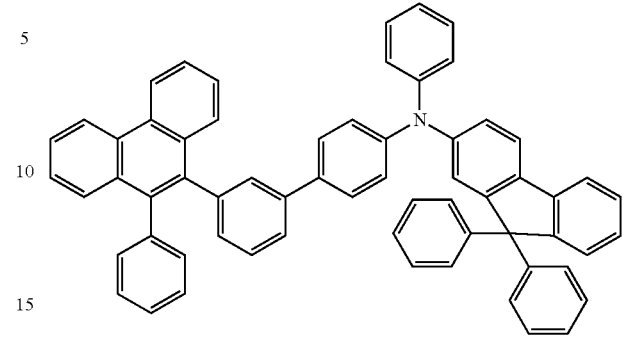
108
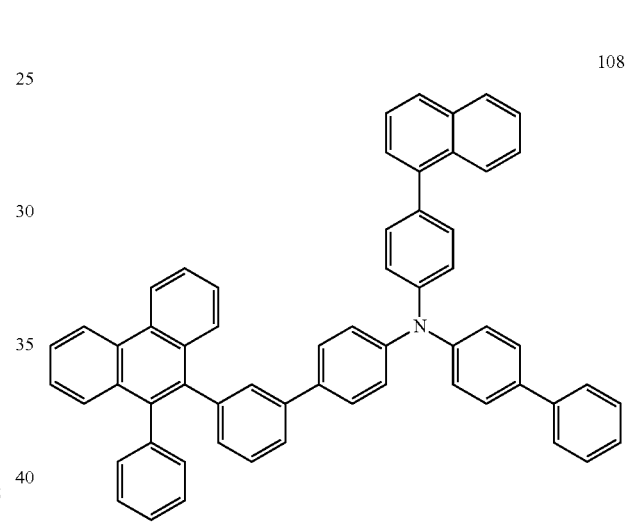
109
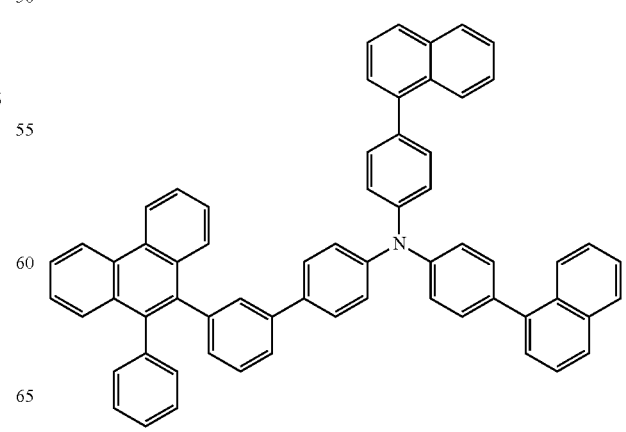

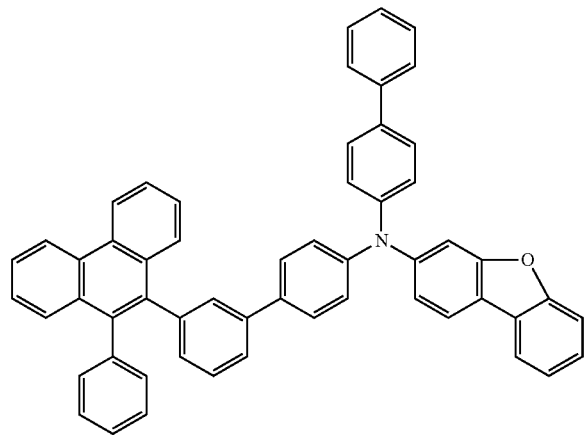
110
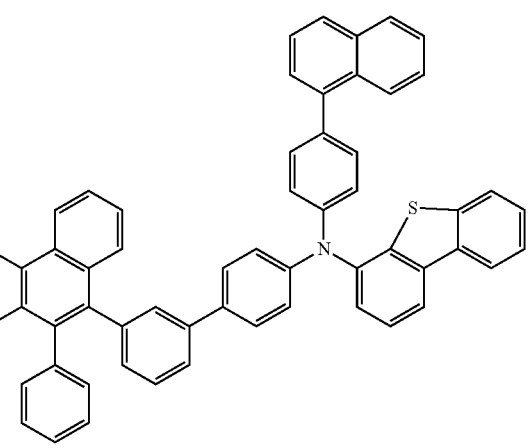
113
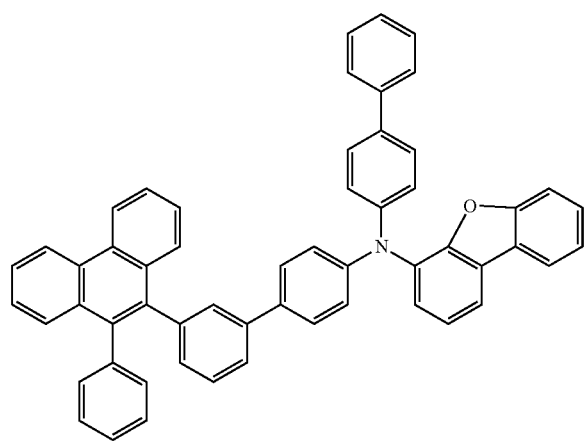
111
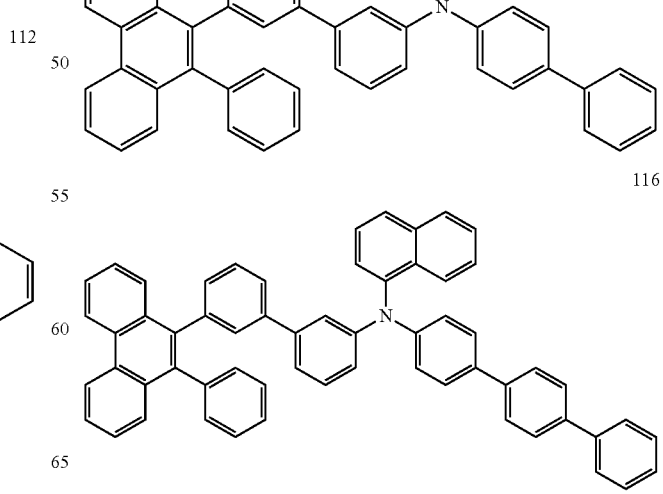
114
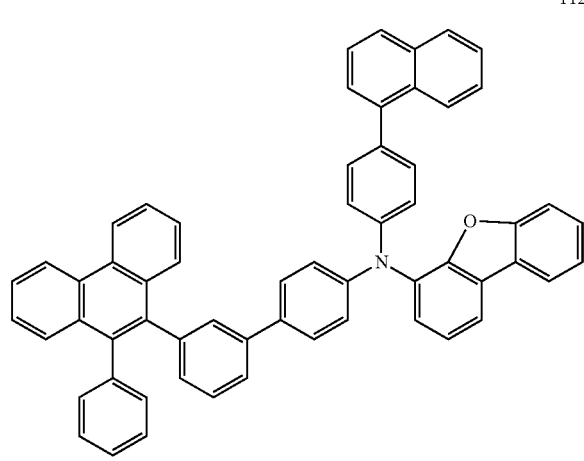
112

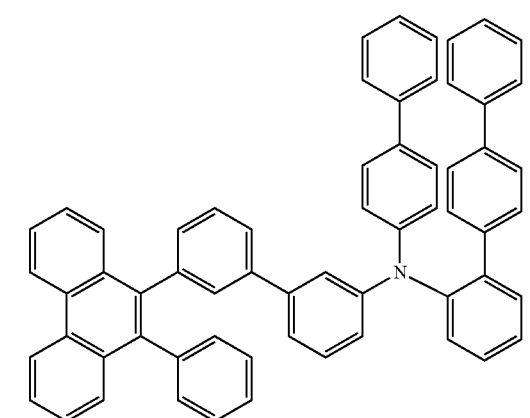
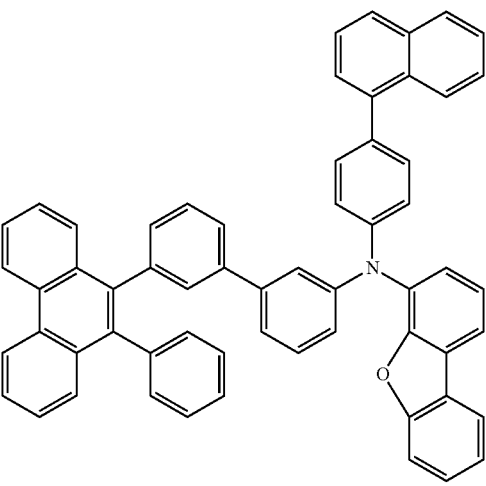

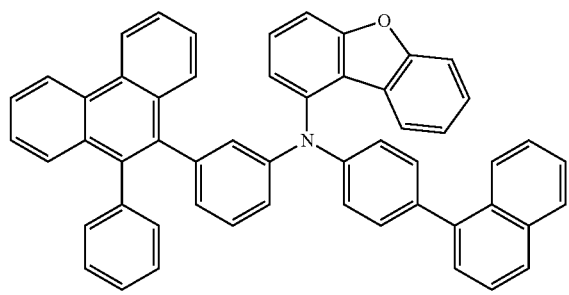
124
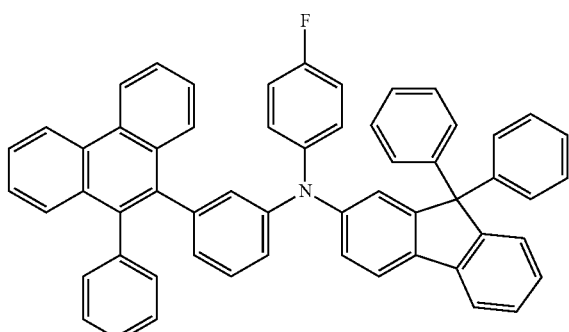
125
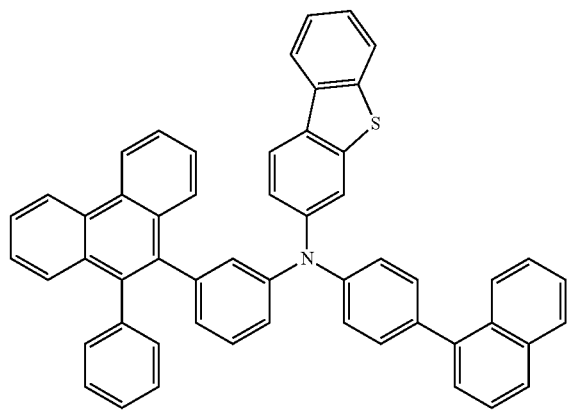
126
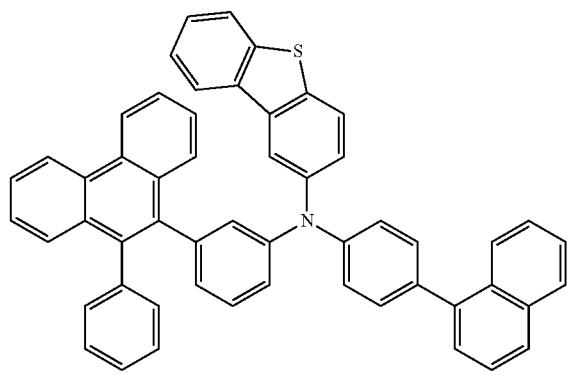
127
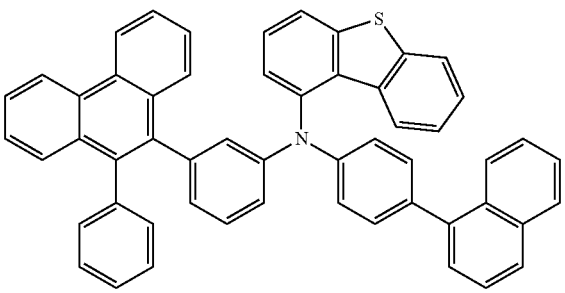
128
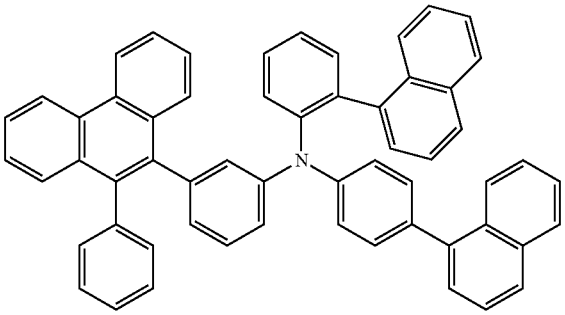
129
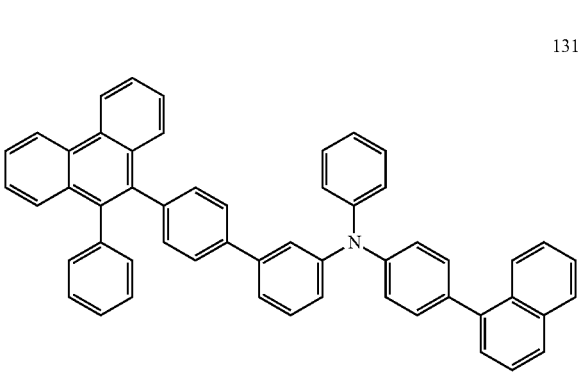
130
131

-continued

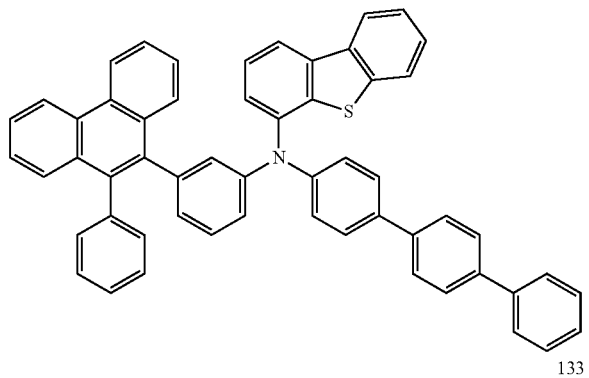
132

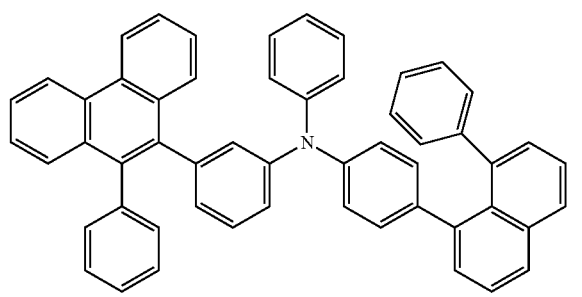
133

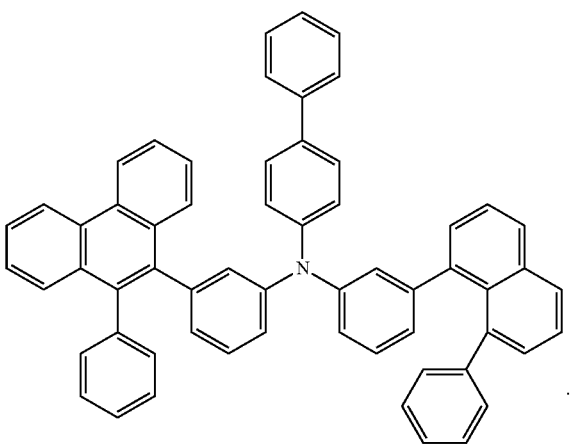
134

The monoamine compound according to an example embodiment may have a relatively large volume. Accordingly, when the monoamine compound represented by Formula 1 is applied to an organic electroluminescence device, high emission efficiency may be secured.

In particular, in an example embodiment, the monoamine compound represented by Formula 1 has a phenanthryl group connected with an amine group via an arylene linker, and a substituent having a large volume such as an aryl group is positioned at an adjacent position to a position where the phenanthryl group is connected with the arylene linker. Accordingly, steric repulsion may arise between the substituent and the arylene linker, the bonding angle between the phenanthryl group and the arylene linker may increase, and the volume occupied by the phenanthryl group may increase. Therefore, the monoamine compound according to an example embodiment may decrease interaction between phenanthryl groups. The decrease of the interaction between the phenanthryl groups may result in the decrease of electron mobility. In the case where the monoamine compound according to an example embodiment is disposed in a hole transport layer HTL adjacent to an emission layer EML, the diffusion of electrons from the emission layer to a hole transport region HTR may be restrained, and high emission efficiency of an organic electroluminescence device may be secured.

Hereinafter, an organic electroluminescence device according to an example embodiment will be explained. The explanation will be mainly given with difference features from the monoamine compound according to an example embodiment, and unexplained parts will follow the above-description on the monoamine compound according to an example embodiment.

An organic electroluminescence device according to an example embodiment includes the monoamine compound according to an example embodiment.

Figure 2:
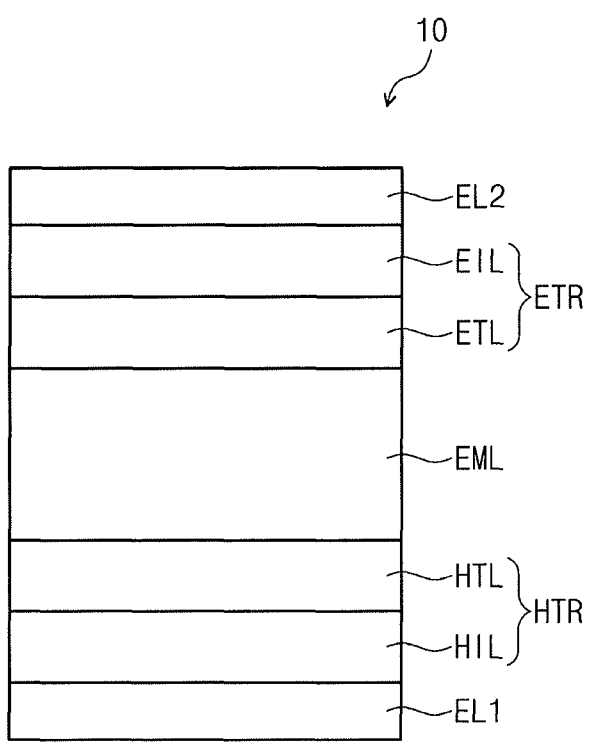
FIG. 2 illustrates a schematic cross-sectional view of an organic electroluminescence device according to an example embodiment.

FIG. 1 is a schematic cross-sectional view illustrating an organic electroluminescence device according to an example embodiment. FIG. 2 is a schematic cross-sectional view illustrating an organic electroluminescence device according to an example embodiment. FIG. 3 is a schematic cross-sectional view illustrating an organic electroluminescence device according to an example embodiment.

Referring to FIGS. 1 and 2, an organic electroluminescence device 10 according to an example embodiment includes a first electrode EL1, a hole transport region HTR, an emission layer EML, an electron transport region ETR, and a second electrode EL2.

The first electrode EL1 has electrical conductivity. The first electrode EL1 may be, for example, a pixel electrode or an anode. The first electrode EL1 may be, for example, a transmissive electrode, a transflective electrode, or a reflective electrode. In the case where the first electrode EL1 is the transmissive electrode, the first electrode EL1 may be formed using, for example, a transparent metal oxide such as indium tin oxide (ITO), indium zinc oxide (IZO), zinc oxide (ZnO), or indium tin zinc oxide (ITZO). In the case where the first electrode EL1 is the transflective electrode or reflective electrode, the first electrode EL1 may include, for example, Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). Also, the first electrode EL1 may have a structure including a plurality of layers including a reflective layer or transflective layer formed using the above materials, and a transparent layer formed using ITO, IZO, ZnO, or ITZO.

The monoamine compound according to an example embodiment may be included in at least one organic layer provided between the first electrode EL1 and the second electrode EL2. Hereinafter, an embodiment that includes the monoamine compound according to an example embodiment in a hole transport region HTR will be explained. However, embodiments are not limited thereto, and, for example, the monoamine compound according to an example embodiment may be included in an emission layer EML.

The organic electroluminescence device according to an example embodiment may include the monoamine compound represented by Formula 1 in a hole transport region HTR. The hole transport region HTR may include one or more monoamine compounds represented by Formula 1.

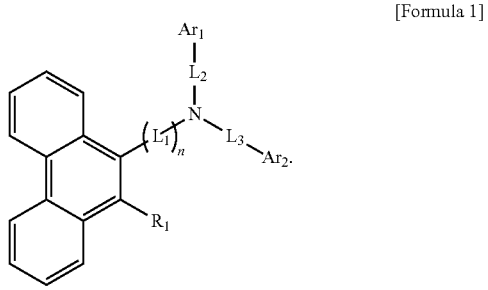

[Formula 1]

In Formula 1, the particular explanation on $R_1$, $L_1$ to $L_3$, n, $Ar_1$ and $Ar_2$ is the same as the above description and will not be repeated.

Particular explanation on the monoamine compound represented by Formula 1 may be applied as the above description and will not be repeated.

The hole transport region HTR may be provided on the first electrode EL1. The hole transport region HTR may include at least one of a hole injection layer HIL, a hole transport layer HTL, a hole buffer layer, or an electron blocking layer. The thickness of the hole transport region HTR may be, for example, from about 1,000 Å to about 1,500 Å.

The hole transport region HTR may have, for example, a single layer formed using a single material, a single layer formed using a plurality of different materials, or a multi-layer structure including a plurality of layers formed using a plurality of different materials.

For example, as shown in FIG. 2, the hole transport region HTR may have a single layer structure of a hole injection layer HIL or a hole transport layer HTL, or may have a single layer structure formed using a hole injection material and a hole transport material. In addition, the hole transport region HTR may have a single layer structure formed using a plurality of different materials, or a laminated structure from the first electrode EL1 of hole injection layer HIL/hole transport layer HTL, hole injection layer HIL/hole transport layer HTL/hole buffer layer, hole injection layer HIL/hole buffer layer, hole transport layer HTL/hole buffer layer, or hole injection layer HIL/hole transport layer HTL/electron blocking layer, without limitation.

As shown in FIG. 3, the hole transport region HTR may have a plurality of hole transport layers. The hole transport region HTR may include a first hole transport layer HTL1 and a second hole transport layer HTL2 which is disposed on the first hole transport layer HTL1. The second hole transport layer HTL2 may be a hole transport layer which is adjacent to the emission layer EML among the plurality of the hole transport layers.

The hole transport region HTR may be formed using various methods such as a vacuum deposition method, a spin coating method, a cast method, a Langmuir-Blodgett (LB) method, an inkjet printing method, a laser printing method, and a laser induced thermal imaging (LITI) method.

The hole transport region HTR may include the monoamine compound according to an example embodiment as a hole transport material. The layer including the monoamine compound according to an example embodiment may be a hole transport layer HTL. In the case where the hole transport layer includes the first hole transport layer HTL1 and the second hole transport layer HTL2 as shown in FIG. 3, the monoamine compound according to an example embodiment may be included in the second hole transport layer HTL2. The monoamine compound according to an example embodiment may be included in an adjacent layer to the emission layer EML, in the hole transport region HTR.

In the case where the hole transport layer HTL includes the monoamine compound according to an example embodiment, the hole injection layer HIL may include, for example, a phthalocyanine compound such as copper phthalocyanine; N,N'-diphenyl-N,N'-bis-[4-(phenyl-M tolyl-amino)-phenyl]-biphenyl-4,4'-diamine (DNTPD), 4,4',4"-tris(3-methylphenylphenylamino)triphenylamine (M MTDATA), 4,4', 4"-tris(N,N-diphenylamino)triphenylamine (TDATA), 4,4', 4"-tris{N-(2-naphthyl)-N-phenylamino}-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-di(naphthalene-1-yl)-N,N'-diphenyl-benzidine (NPB), triphenylamine-containing polyether ketone (TPAPEK), 4-isopropyl-4'-methyldiphenyliodonium tetrakis(pentafluorophenyl)borate, dipyrazino[2,3-f:2',3'-h]quinoxaline-2,3,6,7,10,11-hexacarbonitrile (HAT-CN), etc.

In the case where the hole transport layer HTL does not include the monoamine compound according to an embodiment, but, for example, the emission layer EML includes the monoamine compound according to an embodiment, the hole transport layer HTL may include, for example, carbazole derivatives such as N-phenyl carbazole, and polyvinyl carbazole, fluorine-based derivatives, N,N'-bis(3-methylphenyl)-N,N'-diphenyl-[1,1-biphenyl]-4,4'-diamine (TPD), triphenylamine-based derivatives such as 4,4',4"-tris (N-carbazolyl)triphenylamine (TCTA), N,N'-di(1-naphthyl)-N,N'-diphenylbenzidine (NPB), 4,4'-cyclohexylidene bis[N,N-bis(4-methylphenyl)benzenamine] (TAPC), 4,4'-bis[N,N'-(3-tolyl)amino]-3,3'-dimethylbiphenyl (HMTPD), N-([1,1'-biphenyl]-4-yl)-9,9-dimethyl-N-(4-(9-phenyl-9H-carbazol-3-yl)phenyl)-9H-fluoren-2-amine, etc.

The thickness of the hole transport region HTR may be, for example, from about 100 Å to about 10,000 Å, for example, from about 100 Å to about 1,000 Å. In the case where the hole transport region HTR includes both the hole injection layer HIL and the hole transport layer HTL, the thickness of the hole injection layer HIL may be, for example, from about 100 Å to about 10.000 Å, for example, from about 100 Å to about 1,000 Å, and the thickness of the hole transport layer HTL may be, for example, from about 30 Å to about 1,000 Å. In the case where the thicknesses of the hole transport region HTR, the hole injection layer HIL, and the hole transport layer HIT satisfy the above-described ranges, satisfactory hole transport properties may be obtained without the substantial increase of a driving voltage.

The hole transport region HTR may further include a charge generating material in addition to the above-described materials to improve conductivity. The charge generating material may be dispersed in the hole transport region HTR uniformly or non-uniformly. The charge generating material may be, for example, a p-dopant. The p-dopant may be one of quinone derivatives, metal oxides, or cyano group-containing compounds, without limitation. For example, non-limiting examples of the p-dopant may include quinone derivatives such as tetracyanoquinodimethane (TCNQ), and 2,3,5,6-tetrafluoro-tetracyanoquinodimethane (F4-TCNQ), metal oxides such as tungsten oxide, and molybdenum oxide, without limitation.

As described above, the hole transport region HTR may further include at least one of a hole buffer layer or an electron blocking layer in addition to the hole injection layer HIL and the hole transport layer HTL. The hole buffer layer may compensate an optical resonance distance according to the wavelength of light emitted from the emission layer EML and increase light emission efficiency. Materials included in the hole transport region HTR may be used as materials included in the hole buffer layer. The electron blocking layer is a layer preventing electron injection from the electron transport region ETR into the hole transport region HTR.

The emission layer EML may be provided on the hole transport region HTR. The thickness of the emission layer EML may be, for example, from about 100 Å to about 300 Å. The emission layer EML may have a single layer formed using a single material, a single layer formed using a plurality of different materials, or a multilayer structure having a plurality of layers formed using a plurality of different materials.

The emission layer EML may emit, for example, one of red light, green light, blue light, white light, yellow light, or cyan light. The emission layer EML may include, for example, a fluorescent material or a phosphorescent material. The emission layer EML may include a host and a dopant. The emission layer EML may have a thickness of, for example, about 10 to about 60 nm.

The host material of the emission layer EML may be selected from, for example, anthracene derivatives, fluoranthene derivatives, pyrene derivatives, arylacetylene derivatives, fluorene derivatives, perylene derivatives, chrysene derivatives, and phenanthrene derivatives, and may for example be pyrene derivatives, perylene derivatives, chrysene derivatives, phenanthrene derivatives, or anthracene derivatives. For example, anthracene derivatives represented by the following Formula 5 may be used as the host material of the emission layer EML.

[Formula 5]

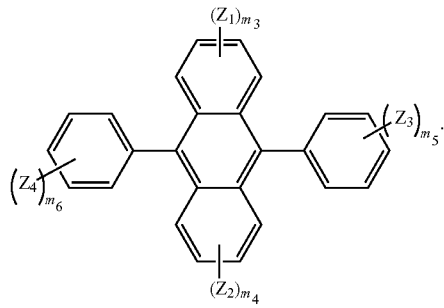

In Formula 5, $Z_1$ to $Z_4$ are each independently a hydrogen atom, a deuterium atom, a halogen atom, a substituted or unsubstituted silyl group, a substituted or unsubstituted alkyl group having 1 to 15 carbon atoms, a substituted or unsubstituted aryl group having 6 to 30 carbon atoms for forming a ring, or a substituted or unsubstituted heteroaryl group having 2 to 30 carbon atoms for forming a ring, $m_3$ and $m_4$ are each independently an integer of 0 to 4, and $m_5$ and $m_6$ are each independently an integer of 0 to 5. In Formula 5, $Z_3$ and $Z_4$ may each independently be combined with an adjacent group to from a ring.

The compound represented by Formula 5 may be the compounds represented as the following structures. However, embodiments of the compound represented by Formula 5 are not limited thereto.

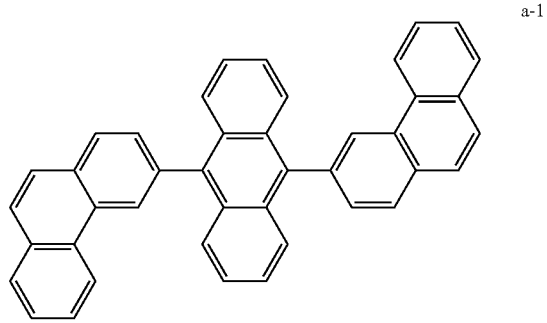

a-1

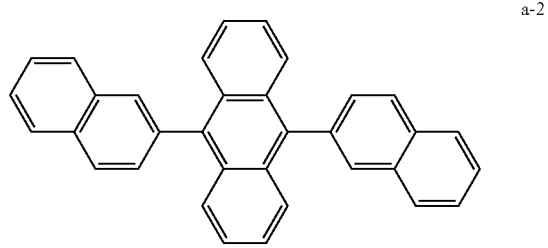

a-2

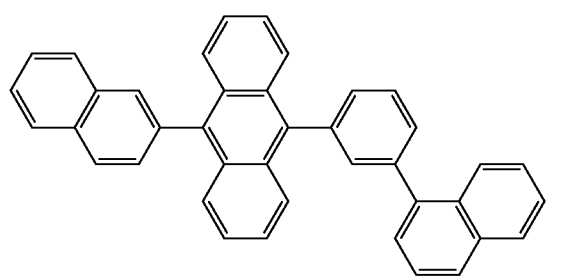

a-3

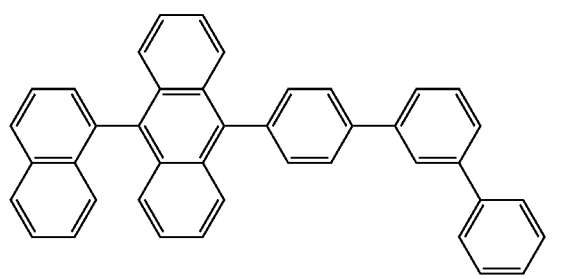

a-4

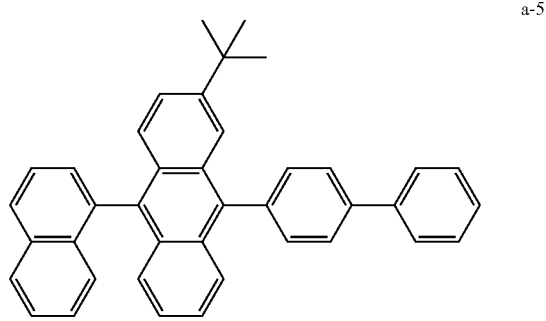

a-5 a-6
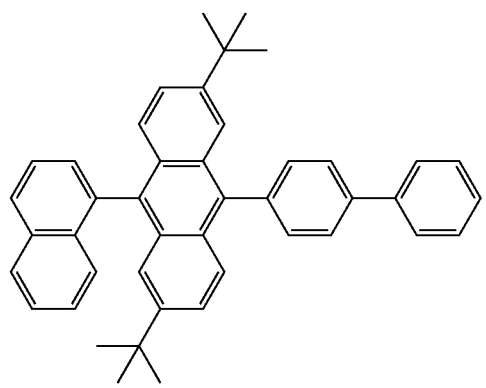

a-7
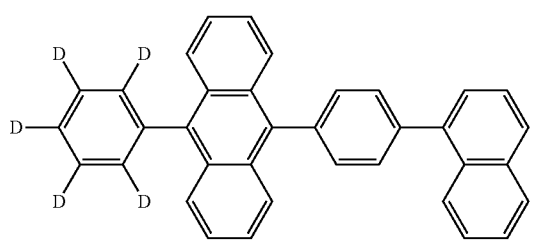

a-8
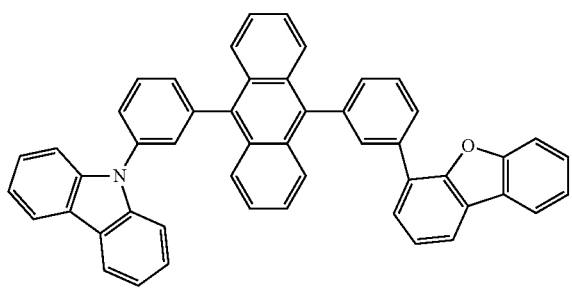

a-9
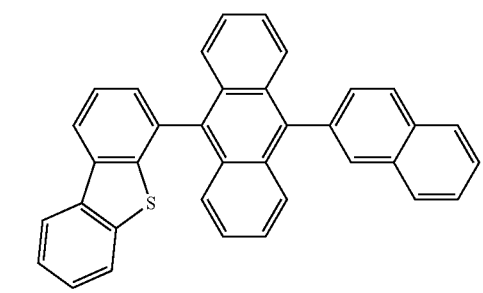

a-10
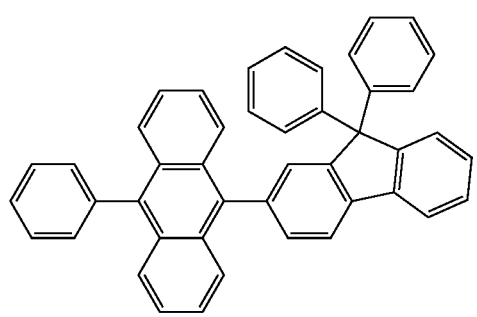

a-11
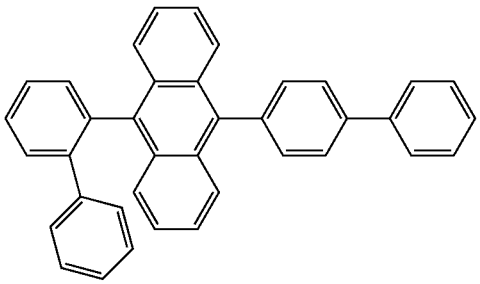

a-12
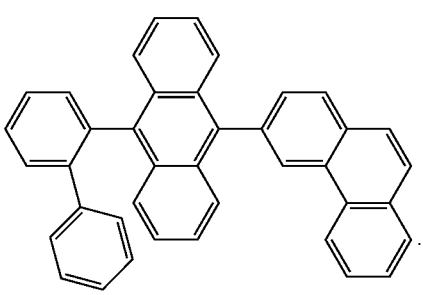

The host may be or include, for example, tris(8-hydroxyquinolino)aluminum ($Alq_3$), 4,4'-bis(N-carbazolyl)-1,1'-biphenyl (CBP), poly(N-vinylcarbazole) (PVK), 9,10-di(naphthaline-2-yl)anthracene (ADN), 4,4',4"-tris(carbazol-9-yl)-triphenylamine (TCTA), 1,3,5-tris(N-phenylbenzimidazole-2-yl)benzene (TPBi), 3-tert-butyl-9,10-di(naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), etc.

The dopant may be or include, for example, styryl derivatives (for example, 1,4-bis[2-(3-N-ethylcarbazolyl)vinyl]benzene (BCzVB), 4-(di-p-tolylamino)-4'-[(di-p-tolylamino)styryl]stilbene (DPAVB), N-(4-((E)-2-(6-((E)-4-(diphenylamino)styryl)naphthalen-2-yl)vinyl)phenyl)-N-phenylbenzenamine (N-BDAVBi)), perylene and the derivatives thereof (for example, 2,5,8,11-tetra-t-butylperylene (TBP)), pyrene and the derivatives thereof (for example, 1,1-dipyrene, 1,4-dipyrenylbenzene, 1,4-bis(N,N-diphenylamino)pyrene), $N^1,N^6$-di(naphthalen-1-yl)-$N^1,N^6$-diphenylpyrene-1,6-diamine, etc.

When the emission layer EML emits red light, the emission layer EML may include, for example, tris(dibenzoylmethanato)phenanthroline europium ($PBD:Eu(DBM)_3$(Phen)), or a fluorescent material including perylene. In the case that the emission layer EML emits red light, the dopant included in the emission layer EML may be selected from, for example, a metal complex or an organometallic complex such as bis(1-phenylisoquinoline)acetylacetonate iridium (PIQIr(acac)), bis(1-phenylquinoline)acetylacetonate iridium (PQIr(acac), tris(1-phenylquinoline)iridium (PQIr), and octaethylporphyrin platinum (PtOEP), rubrene and the derivatives thereof, or 4-dicyanomethylene-2-(p-dimethylaminostyryl)-6-methyl-4H-pyran (DCM) and the derivatives thereof.

In the case where the emission layer EML emits green light, the emission layer EML may include, for example, a fluorescent material including, for example, tris(8-hydroxyquinolino)aluminum ($Alq_3$). In the case where the emission layer EML emits green light, the dopant included in the emission layer EML may be selected from, for example, a metal complex or organometallic complex such as fac-tris (2-phenylpyridine)iridium (Ir(ppy)$_3$), or coumarin and the derivatives thereof.

In the case where the emission layer EML emits blue light, the emission layer EML may further include, for example, a fluorescent material including, for example, one or more of spiro-DPVBi, spiro-6P, distyryl-benzene (DSB). distyryl-arylene (DSA), a polyfluorene (PFO)-based polymer, and a poly(p-phenylene vinylene) (PPV)-based polymer. In the case where the emission layer EML emits blue light, the dopant included in the emission layer EML may be selected from, for example, a metal complex or an organometallic complexes such as (4,6-F$_2$ppy)$_2$Irpic, or perylene and the derivatives thereof.

The electron transport region ETR may be provided on the emission layer EML. The electron transport region ETR may include, for example, at least one of an hole blocking layer, an electron transport layer ETL or an electron injection layer EIL, without limitation.

The electron transport region ETR may have, for example, a single layer formed using a single material, a single layer formed using a plurality of different materials, or a multilayer structure having a plurality of layers formed using a plurality of different materials.

For example, the electron transport region ETR may have a single layer structure of the electron injection layer EIL or the electron transport layer ETL, or a single layer structure formed using an electron injection material and an electron transport material. In addition, the electron transport region ETR may have a single layer structure having a plurality of different materials, or a structure laminated from the first electrode EL1 of electron transport layer ETL/electron injection layer EIL, or hole blocking layer/electron transport layer ETL/electron injection layer EIL, without limitation. The thickness of the electron transport region ETR may be, for example, from about 1,000 Å to about 1,500 Å.

The electron transport region ETR may be formed using various methods such as a vacuum deposition method, a spin coating method, a cast method, a Langmuir-Blodgett (LB) method, an inkjet printing method, a laser printing method, and a laser induced thermal imaging (LITI) method.

In the case where the electron transport region ETR includes the electron transport layer ETL, the electron transport region ETR may include, for example, tris(8-hydroxyquinolinato)aluminum (Alq$_3$), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazolyl-1-ylphenyl)-9,10-dinaphthylanthracene, 1,3,5-tri(1-phenyl-1H-benzo[d]imidazol-2-yl)benzene (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,08)-(1,1'-biphenyl-4-olato) aluminum (BAlq), berylliumbis(benzoquinolin-10-olate (Bebq$_2$), 9,10-di(naphthalene-2-yl)anthracene (ADN), or a mixture thereof, without limitation. The thickness of the electron transport layer ETL may be, for example, from about 100 Å to about 1,000 Å and may be from about 150 Å to about 500 Å. If the thickness of the electron transport layer ETL satisfies the above-described range, satisfactory electron transport property may be obtained without substantial increase of a driving voltage.

When the electron transport region ETR includes the electron injection layer EIL, the electron injection layer EIL may include, for example, a metal such as Al, Ag, Li, Mg and Ca and a mixture thereof. However, an example embodiment is not limited thereto. For example, the electron injection layer EIL may use LiF, lithium quinolate (Liq), Li$_2$O, BaO, NaCl, CsF, a metal in lanthanides such as Yb, or a metal halide such as RbCl and RbI, without limitation. The electron injection layer EIL also may be formed using a mixture material of an electron transport material and an insulating organo metal salt. The organo metal salt may be a material having an energy band gap of, for example, about 4 eV or more. For example, the organo metal salt may include a metal acetate, a metal benzoate, a metal acetoacetate, a metal acetylacetonate, or a metal stearate. The thickness of the electron injection layer EIL may be, for example, from about 1 Å to about 100 Å, and from about 3 Å to about 90 Å. In the case where the thickness of the electron injection layer EIL satisfies the above described range, satisfactory electron injection properties may be obtained without inducing the substantial increase of a driving voltage.

The electron transport region ETR may include a hole blocking layer, as described above. The hole blocking layer may include at least one of, for example, 2,9-dimethyl-4,7-diphenyl-1,10-phenanthroline (BCP), or 4,7-diphenyl-1,10-phenanthroline (Bphen), without limitation.

The second electrode EL2 may be provided on the electron transport region ETR. The second electrode EL2 may be, for example, a common electrode or a cathode. The second electrode EL2 may be, for example, a transmissive electrode, a transflective electrode, or a reflective electrode. In the case where the second electrode EL2 is the transmissive electrode, the second electrode EL2 may be formed using, for example, ITO, IZO, ZnO, ITZO, etc.

In the case where the second electrode EL2 is the transflective electrode or the reflective electrode, the second electrode EL2 may include, for example, Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). The second electrode EL2 may have, for example, a multilayered structure including a reflective layer or a transflective layer formed using the above-described materials and a transparent conductive layer formed using ITO, IZO, ZnO, ITZO, etc.

In an implementation, the second electrode EL2 may be connected with an auxiliary electrode. In the case where the second electrode EL2 is connected with the auxiliary electrode, the resistance of the second electrode EL2 may decrease.

In the organic electroluminescence device 10, according to the application of a voltage to each of the first electrode EL1 and second electrode EL2, holes injected from the first electrode EL1 may move via the hole transport region HTR to the emission layer EML, and electrons injected from the second electrode EL2 may move via the electron transport region ETR to the emission layer EML. The electrons and the holes may recombine in the emission layer EML to generate excitons, and the excitons may emit light via transition from an excited state to a ground state.

In the case where the organic electroluminescence device 10 is a top emission type, the first electrode EL1 may be a reflective electrode, and the second electrode EL2 may be a transmissive electrode or a transflective electrode. In the case where the organic electroluminescence device 10 is a bottom emission type, the first electrode EL1 may be a transmissive electrode or a transflective electrode, and the second electrode EL2 may be a reflective electrode.

The organic electroluminescence device according to an example embodiment includes a monoamine compound represented by Formula 1, which may help provide high emission efficiency. The monoamine compound represented by Formula 1 may have a relatively large volume. In an example embodiment, in the monoamine compound represented by Formula 1, a phenanthryl group is connected with an amine group via an arylene linker, and a substituent having a large volume such as an aryl group is positioned at an adjacent position to a position where the phenanthryl group is connected with the arylene linker. Accordingly, steric repulsion may arise between the substituent and the arylene linker, the bonding angle between the phenanthryl group and the arylene linker may increase, and the volume occupied by the phenanthryl group may increase. Therefore, a monoamine compound according to an example embodiment may decrease interaction between phenanthryl groups. The decrease of the interaction between the phenanthryl groups may result in the decrease of electron mobility. In the case where the monoamine compound according to an example embodiment is disposed in a hole transport layer HTL which is adjacent to an emission layer EML, the diffusion of electrons from the emission layer to a hole transport region HTR may be restrained, and high emission efficiency of an organic electroluminescence device may be secured.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Compounds according to example embodiments may be synthesized, for example, as follows. However, an example embodiment is not limited thereto.

SYNTHETIC EXAMPLES

1. Synthesis of Compound 1

Compound 1 which is a compound according to an example embodiment may be synthesized by the following reaction.

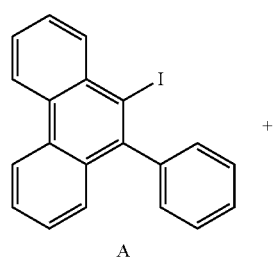

A

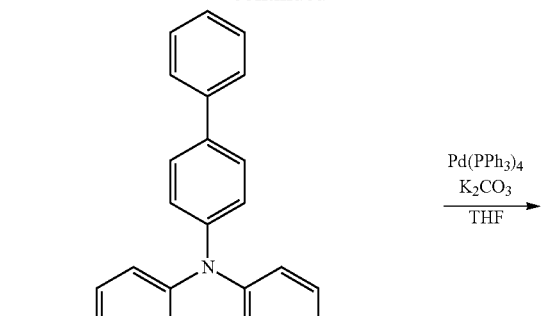

B

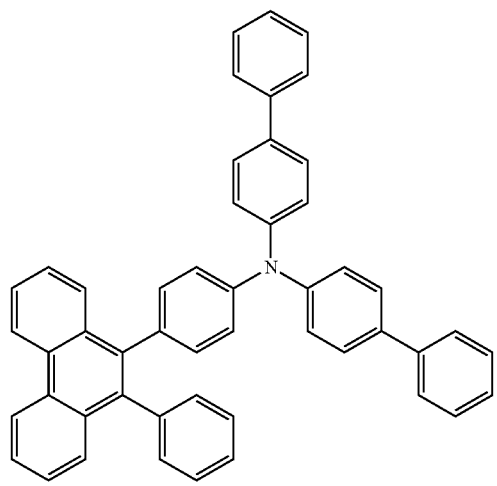

1

Under an argon (Ar) atmosphere, 4.30 g of Compound A, 9.98 g of Compound B, 654 mg of tetrakis(triphenylphosphine)palladium(0) (Pd(PPh$_3$)$_4$), and 6.91 g of potassium carbonate (K$_2$CO$_3$) were added to a solvent of THF (200 ml)/water (50 ml) and deaerated. The reaction mixture was stirred and refluxed for 8 hours. After that, the reactant was cooled, extracted with chloroform, and washed with a saturated saline solution. The organic layer thus obtained was dried with anhydrous sodium sulfate, filtered, and concentrated, and residues were separated by column chromatography to obtain 5.29 g (yield 72%) of Compound 1 as a white solid. The molecular weight of the compound measured by FAB-MS was 649. In addition, the chemical shift values of the compound measured by $^1$H-NMR were 8.93 (m, 2H), 7.83 (m, 1H), 7.76-7.55 (12H), 7.51 (ddd, 1H, J=1, 7, 8 Hz), 7.47-7.34 (7H), 7.34-7.26 (2H), 7.26-7.19 (2H), 7.18-7.09 (6H), 7.05 (ddd, 2H, J=2, 2, 9 Hz). From the results, the white solid compound was identified as Compound 1.

2. Synthesis of Compound 12

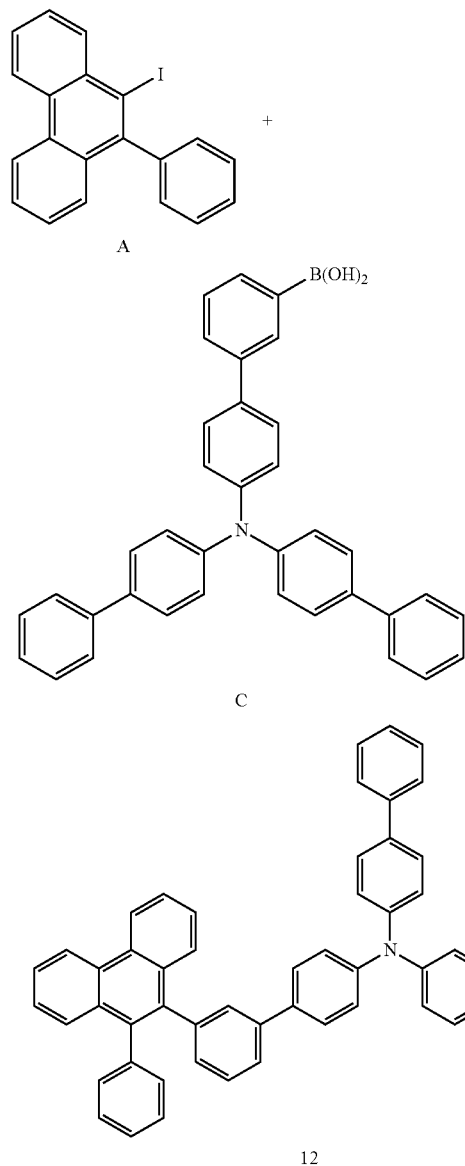

12

Under an argon (Ar) atmosphere, 3.78 g of Compound A, 10.3 g of Compound C, 575 mg of tetrakis(triphenylphosphine)palladium(0) (Pd(PPh$_3$)$_4$), and 6.34 g of potassium carbonate (K$_2$CO$_3$) were added to a solvent of THF (200 ml)/water (50 ml) and deaerated. The reaction mixture was stirred and refluxed for 8 hours. After that, the reactant was cooled, extracted with chloroform, and washed with a saturated saline solution. The organic layer thus obtained was dried with anhydrous sodium sulfate, filtered, and concentrated, and residues were separated by column chromatography to obtain 4.55 g (yield 63%) of Compound 12 as a white solid. The molecular weight of the compound measured by FAB-MS was 725. In addition, the chemical shift values of the compound measured by $^1$H-NMR were 8.93 (d, 2H, J=8 Hz), 7.74-7.55 (12H), 7.55-7.46 (6H), 7.46-7.12 (19H). From the results, the white solid compound was identified as Compound 12.

3. Synthesis of Compound 38

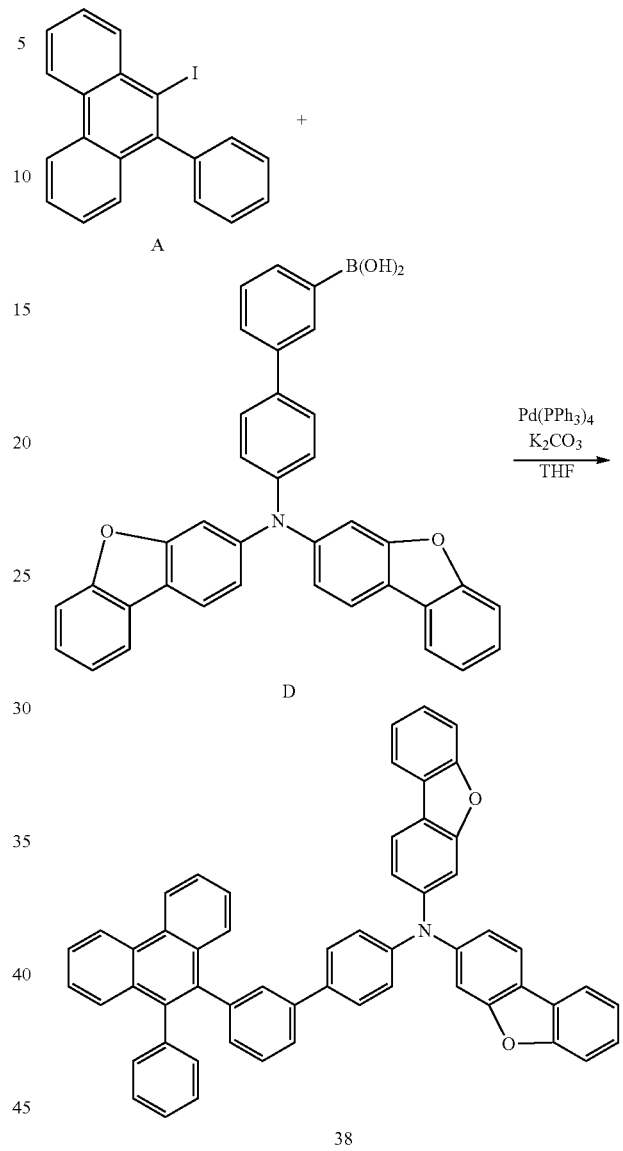

38

Under an argon (Ar) atmosphere, 2.51 g of Compound A, 7.19 g of Compound D, 381 mg of tetrakis(triphenylphosphine)palladium(0) (Pd(PPh$_3$)$_4$), and 5.31 g of potassium carbonate (K$_2$CO$_3$) were added to a solvent of THF (200 ml)/water (50 ml) and deaerated. The reaction mixture was stirred and refluxed for 8 hours. After that, the reactant was cooled, extracted with chloroform, and washed with a saturated saline solution. The organic layer thus obtained was dried with anhydrous sodium sulfate, filtered, and concentrated, and residues were separated by column chromatography to obtain 3.38 g (yield 68%) of Compound 38 as a white solid. The molecular weight of the compound measured by FAB-MS was 753. In addition, the chemical shift values of the compound measured by $^1$H-NMR were 8.87 (m, 2H), 7.96 (m, 2H), 7.92 (d, 2H, J=8H), 7.75 (m, 1H), 7.71-7.50 (7H), 7.50-7.36 (5H), 7.36-7.10 (16H). From the results, the white solid compound was identified as Compound 38.

4. Synthesis of Compound 11
(Synthesis of Compound F)

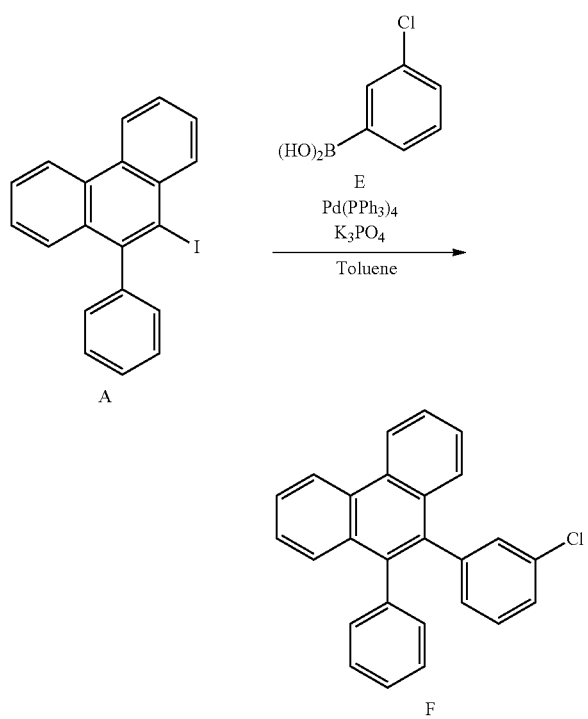

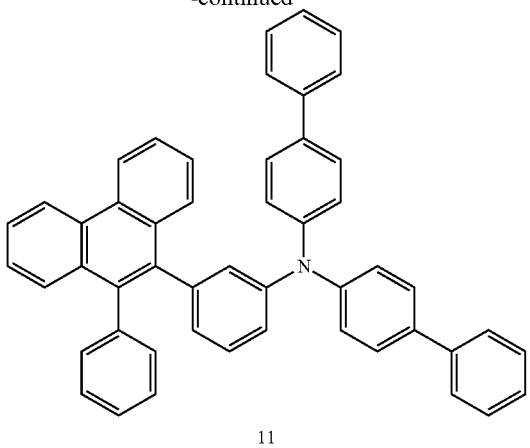

11

Under an argon (Ar) atmosphere, 10.0 g of Compound A, 29.2 g of Compound E, 2.22 g of tetrakis(triphenylphosphine)palladium(0) (Pd(PPh$_3$)$_4$), and 431 mg of palladium acetate (Pd(OAc)$_2$) were added to a solvent of toluene (300 ml)/ethyl alcohol (130 ml)/aqueous solution of 2 M tripotassium orthophosphate (K$_3$PO$_4$) (64 ml), and deaerated. The reaction mixture was stirred and refluxed for 24 hours. After that, the reaction product was cooled, extracted with chloroform, and washed with a saturated saline solution.

The organic layer thus obtained was dried with anhydrous sodium sulfate, filtered, and concentrated, and residues were separated by column chromatography to obtain 16.1 g (yield 69%) of Compound F as a white solid.

(Synthesis of Compound 11)

Under an argon (Ar) atmosphere, 4.01 g of Compound F, 3.89 g of Compound G, 1.06 g of sodium t-butoxide, 316 mg of bis(dibenzylideneacetone)palladium(0) (Pd(dba)$_2$), and 1.47 ml of 1.5 M toluene solution of tri-t-butyl phosphine ($^t$Bu$_3$P) were added to 150 ml of toluene, and deaerated. The reaction mixture was stirred and refluxed for 24 hours. After that, the reaction product was cooled, extracted with chloroform, and washed with a saturated saline solution.

The organic layer thus obtained was dried with anhydrous sodium sulfate, filtered, and concentrated, and residues were separated by column chromatography to obtain 6.01 g (yield 84%) of Compound 11 as a white solid. The molecular weight of the compound measured by FAB-MS was 649. In addition, the chemical shift values of the compound measured by $^1$H-NMR were 8.88 (d, 2H. J=10 Hz), 7.76-7.43 (21H), 7.43-7.17 (5H), 7.09 (ddd, 4H, J=2, 2, 8 Hz), 7.04-6.90 (3H). From the results, the white solid compound was identified as Compound 11.

5. Synthesis of Compound 16
(Synthesis of Compound 11)

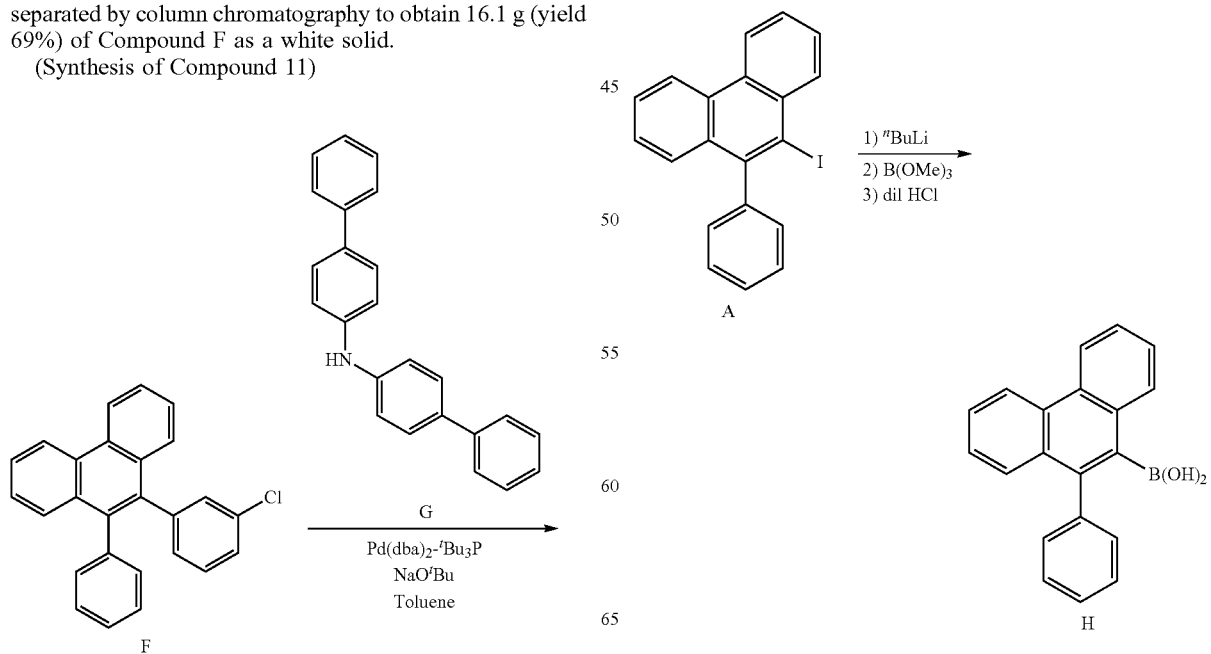

Under an argon (Ar) atmosphere, 20.0 g of Compound A was stirred in 300 ml of THF at −78° C. for 10 minutes, and 21.7 ml of n-butyllithium (n-BuLi) with 1.6 M concentration was slowly added thereto dropwise using a dropping funnel, followed by additionally stirring for 30 minutes. Then, 7.05 ml of trimethyl borate (B(OMe)$_3$) was slowly added thereto dropwise using a dropping funnel and additionally stirred at room temperature for 3 hours. After that, 300 ml of 1 M HCl solution was added and extracted once. Then, the product thus obtained was additionally extracted three times using water and toluene. The organic layer thus obtained was dried with anhydrous sodium sulfate, filtered, and concentrated, and residues were separated by column chromatography to obtain 4.78 g (yield 30%) of Compound H as a white solid.

(Synthesis of Compound J)

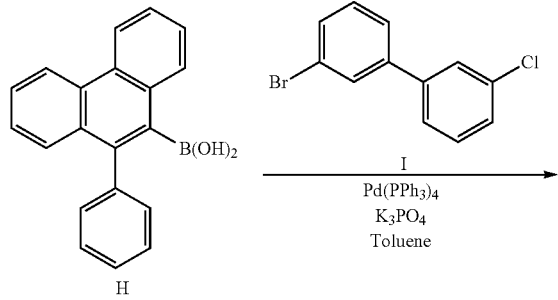

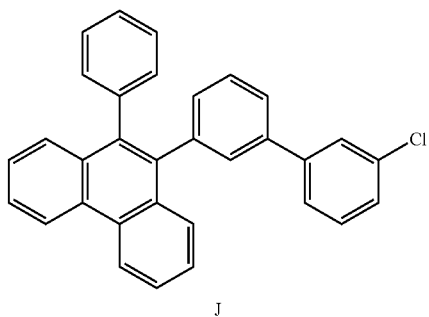

Under an argon (Ar) atmosphere, 4.50 g of Compound H, 4.04 g of Compound I, 9.61 g of tripotassium orthophosphate (K$_3$PO$_4$), and 872 mg of tetrakis(triphenylphosphine)palladium(0) (Pd(PPh$_3$)$_4$), were added to a solvent of toluene (150 ml)/ethyl alcohol (10 ml)/water (5 ml), and deaerated. The reaction mixture was stirred and refluxed for 24 hours. After that, the reaction product was cooled, extracted with chloroform, and washed with a saturated saline solution. The organic layer thus obtained was dried with anhydrous sodium sulfate, filtered, and concentrated, and residues were separated by column chromatography to obtain 2.80 g (yield 42%) of Compound J as a white solid.

(Synthesis of Compound 16)

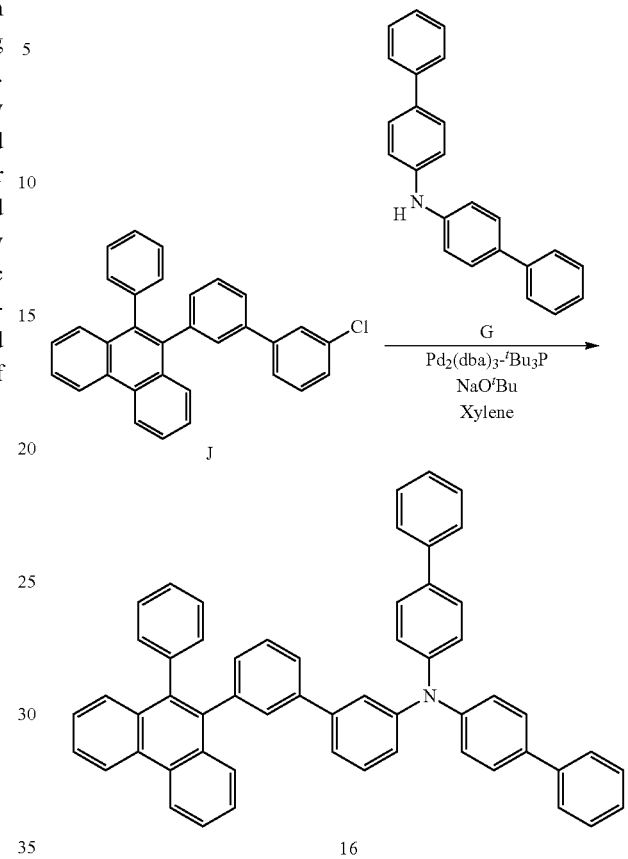

Under an argon (Ar) atmosphere, 2.45 g of Compound J, 1.79 g of Compound G, 1.06 g of sodium t-butoxide, 152 mg of tris(dibenzylideneacetone)dipalladium(0) (Pd$_2$(dba)$_3$), and 0.21 ml of 1.6 M toluene solution of tri-t-butyl phosphine ($^t$Bu$_3$P) were added to 150 ml of xylene, and deaerated. The reaction mixture was stirred and refluxed for 8 hours. After that, the reaction product was cooled, extracted with chloroform, and washed with a saturated saline solution. The organic layer thus obtained was dried with anhydrous sodium sulfate, filtered, and concentrated, and residues were separated by column chromatography to obtain 3.11 g (yield 70%) of Compound 16 as a white solid. The molecular weight of the compound measured by FAB-MS was 725. In addition, the chemical shift values of the compound measured by $^1$H-NMR were 8.92 (d, 2H, J=8 Hz), 7.75-7.56 (11H), 7.56-6.95 (26H). From the results, the white solid compound was identified as Compound 16.

5. Synthesis of Compound 73

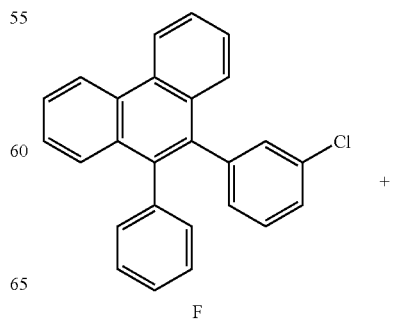

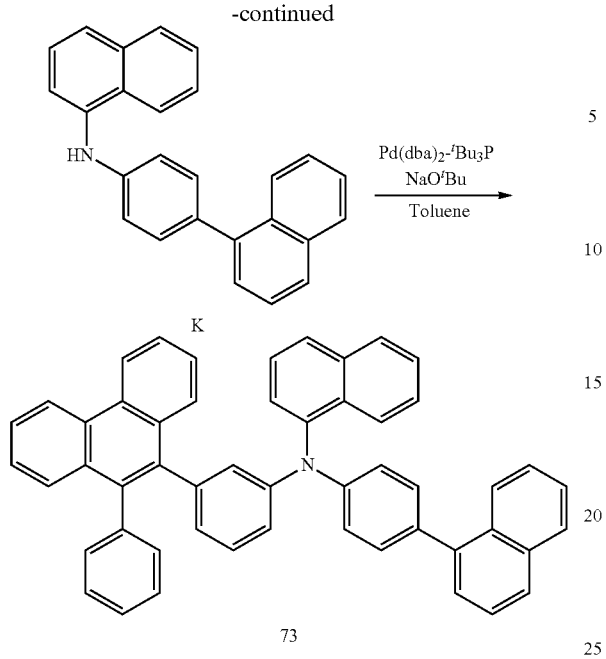

Compound F was synthesized by the same synthetic method of Compound F in the synthetic method of Compound 11. Then, under an argon (Ar) atmosphere, 5.00 g of Compound F, 5.21 g of Compound K, 1.32 g of sodium t-butoxide, 390 mg of bis(dibenzylideneacetone)palladium (0) (Pd(dba)$_2$), and 1.83 ml of 1.5 M toluene solution of tri-t-butyl phosphine ($^t$Bu$_3$P) were added to 150 ml of toluene, and deaerated. The reaction mixture was stirred and refluxed for 24 hours. After that, the reaction product was cooled, extracted with chloroform, and washed with a saturated saline solution.

The organic layer thus obtained was dried with anhydrous sodium sulfate, filtered, and concentrated, and residues were separated by column chromatography to obtain 6.65 g (yield 72%) of Compound 73 as a white solid. The molecular weight of the compound measured by FAB-MS was 673. In addition, the chemical shift values of the compound measured by $^1$H-NMR were 8.88 (d, 2H, J=9 Hz), 8.05-7.77 (6H), 7.72-7.60 (3H), 7.60-7.27 (16H), 7.24 (m, 1H), 7.20-7.08 (3H), 6.97 (m, 2H), 6.92-6.82 (2H). From the results, the white solid compound was identified as Compound 16.

7. Synthesis of Compound 103

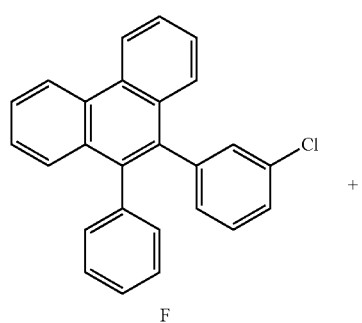

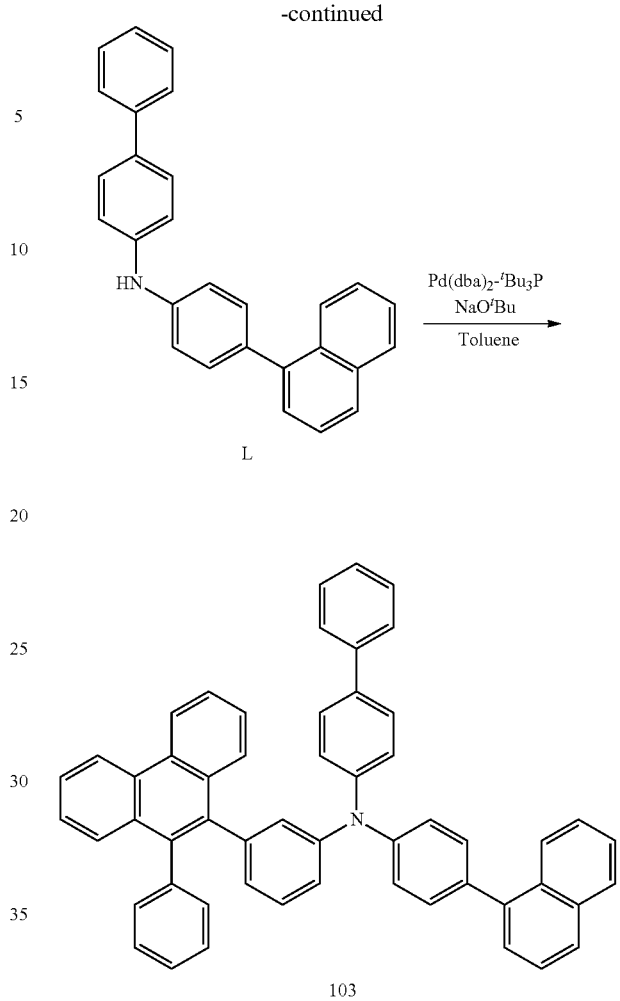

Compound F was synthesized by the same synthetic method of Compound F in the synthetic method of Compound 11. Then, under an argon (Ar) atmosphere, 4.20 g of Compound F, 4.70 g of Compound L, 1.11 g of sodium t-butoxide, 331 mg of bis(dibenzylideneacetone)palladium (0) (Pd(dba)$_2$), and 1.53 ml of 1.5 M toluene solution of tri-t-butyl phosphine ($^t$Bu$_3$P) were added to 150 ml of toluene, and deaerated. The reaction mixture was stirred and refluxed for 24 hours. After that, the reaction product was cooled, extracted with chloroform, and washed with a saturated saline solution.

The organic layer thus obtained was dried with anhydrous sodium sulfate, filtered, and concentrated, and residues were separated by column chromatography to obtain 6.93 g (yield 86%) of Compound 103 as a white solid. The molecular weight of the compound measured by FAB-MS was 699. In addition, the chemical shift values of the compound measured by $^1$H-NMR were 8.89 (d, 2H, J=8 Hz), 8.00 (d, 1H, J=8 Hz), 7.92 (dd, 1H, J=2, 8 Hz), 7.86 (d, 1H, J=8 Hz), 7.78-7.33 (21H), 7.33-7.20 (4H), 7.20-7.03 (6H), 6.99 (ddd, 1H, J=1, 1, 8 Hz). From the results, the white solid compound was identified as Compound 103.

8. Synthesis of Compound 104

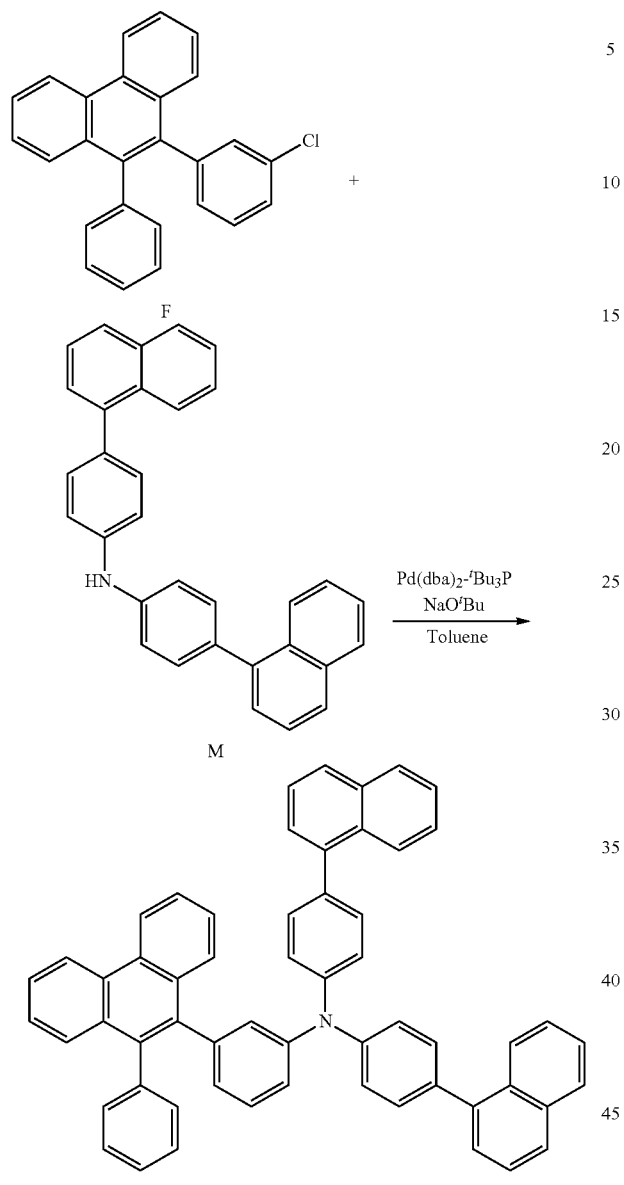

Compound F was synthesized by the same synthetic method of Compound F in the synthetic method of Compound 11. Then, under an argon (Ar) atmosphere, 5.00 g of Compound F, 6.35 g of Compound M, 1.32 g of sodium t-butoxide, 390 mg of bis(dibenzylideneacetone)palladium (0) (Pd(dba)$_2$), and 1.83 ml of 1.5 M toluene solution of tri-t-butyl phosphine ($^t$Bu$_3$P) were added to 150 ml of toluene, and deaerated. The reaction mixture was stirred and refluxed for 24 hours. After that, the reaction product was cooled, extracted with chloroform, and washed with a saturated saline solution.

The organic layer thus obtained was dried with anhydrous sodium sulfate, filtered, and concentrated, and residues were separated by column chromatography to obtain 8.53 g (yield 83%) of Compound 104 as a white solid. The molecular weight of the compound measured by FAB-MS was 699. In addition, the chemical shift values of the compound measured by $^1$H-NMR were 8.90 (d, 2H, J=9 Hz), 8.02 (d, 2H, J=9 Hz), 7.92 (d, 2H, J=8 Hz), 7.86 (d, 2H, J=8 Hz), 7.78-7.62 (3H), 7.62-7.40 (16H), 7.40-7.09 (11H), 7.00 (m, 1H). From the results, the white solid compound was identified as Compound 104.

9. Synthesis of Compound 122

(Synthesis of Compound P)

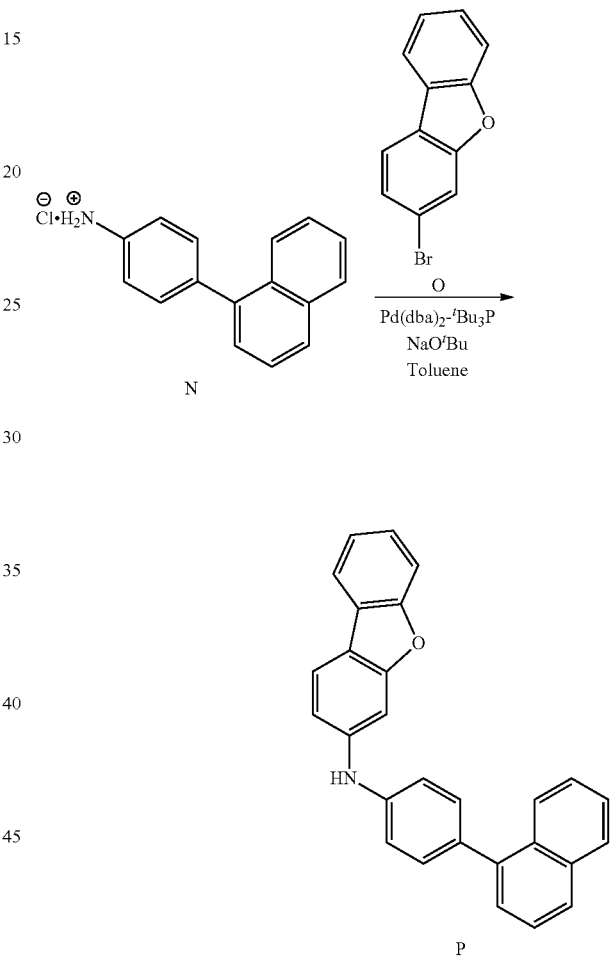

Under an argon (Ar) atmosphere, 7.25 g (28.3 mmol) of Compound N, 7.00 g (28.3 mmol) of Compound O, 326 mg (0.566 mmol) of bis(dibenzylideneacetone)palladium(0) (Pd (dba)$_2$), 0.687 ml (1.13 mmol) of a 1.65 M tri-t-butylphosphine ($^t$Bu$_3$P) solution, and 2.72 g (28.3 mmol) of sodium t-butoxide were added to 200 ml of toluene, and deaerated. The reaction mixture was stirred at about 90° C. for about 4 hours. After that, the reaction product was cooled at room temperature, and treated with a filtration column, and the reaction product thus filtered was concentrated. The concentrated reaction product was recrystallized with toluene-ethanol to obtain 7.30 g (18.9 mmol, yield 67%) of Compound P.

(Synthesis of Compound 122)

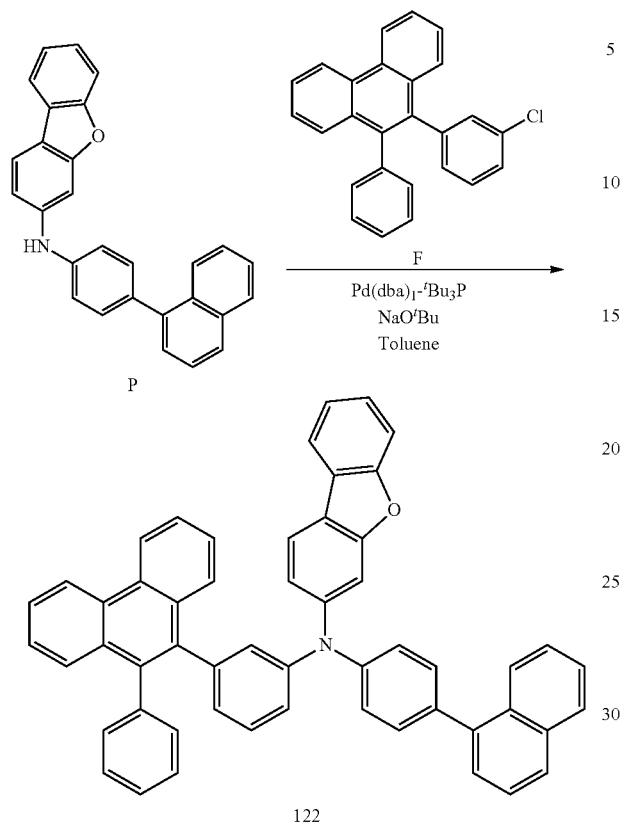

[Example Compounds]

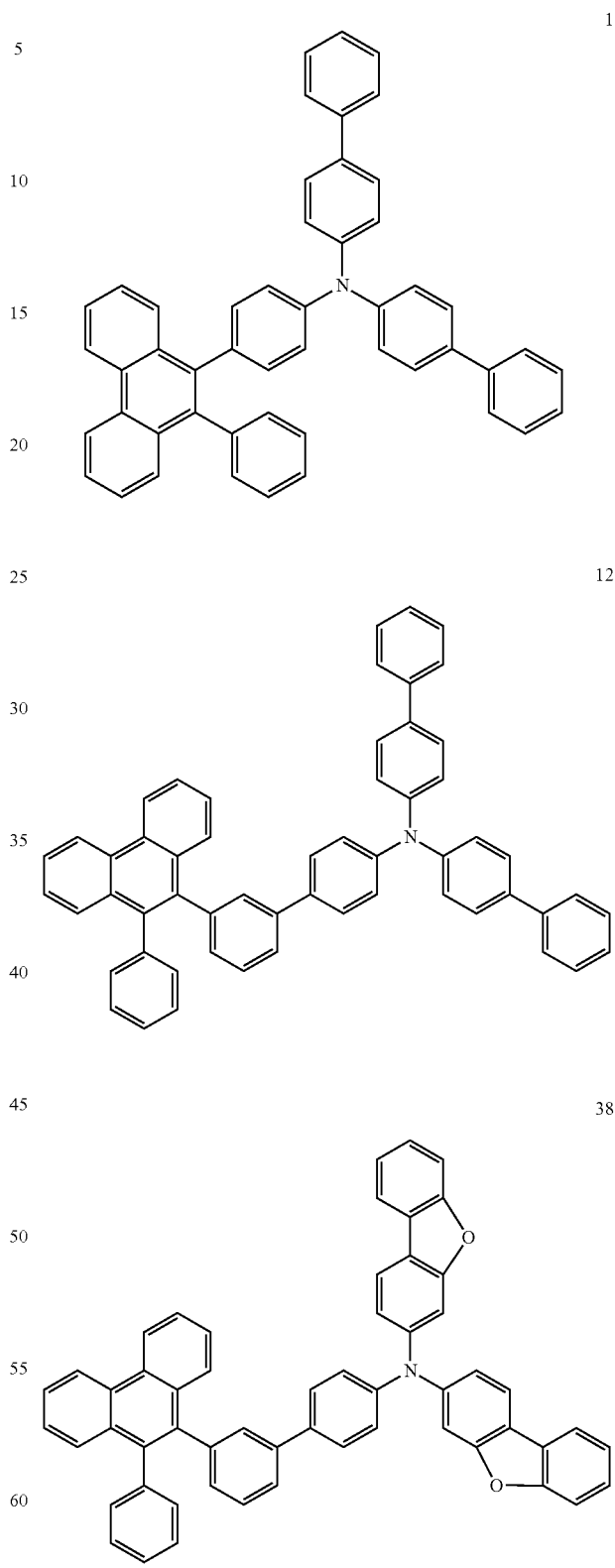

Under an argon (Ar) atmosphere, 6.80 g (17.6 mmol) of Compound P, 6.44 g (17.6 mmol) of Compound F, 406 mg (0.706 mmol) of bis(dibenzylideneacetone)palladium(O) (Pd(dba)$_2$), 0.856 ml (1.41 mmol) of a 1.65 M tri-t-butylphosphine ($^t$Bu$_3$P) solution, and 2.54 g (26.3 mmol) of sodium t-butoxide were added to 200 ml of toluene, and deaerated. The reaction mixture was heated and refluxed while heating and stirring for about 20 hours. After that, the reaction product was cooled at room temperature, and treated with a filtration column, and the reaction product thus filtered was concentrate. The concentrated reaction product was recrystallized with toluene-ethanol to obtain 8.52 g (12.0 mmol, yield 68%) of Compound 122. The molecular weight of the compound measured by FAB-MS was 713. In addition, the chemical shift values of the compound measured by $^1$H-NMR were 8.89 (d, 2H, J=9 Hz), 8.05-7.82 (5H), 7.79-7.05 (27H), 6.99 (ddd, 1H, J=1.2 Hz, 1.2 Hz, 7.4 Hz). From the results, the compound thus obtained was identified as Compound 122.

DEVICE MANUFACTURING EXAMPLES

Hereinafter, device manufacture and evaluation of emission efficiency properties were conducted twice with respect to devices having different configuration.

DEVICE MANUFACTURING EXAMPLES 1

Organic electroluminescence devices according to Examples 1 to 3 were manufactured using Compounds 1, 12 and 38 as hole transport materials.

Organic electroluminescence devices according to Comparative Examples 1 to 6 were manufactured using Comparative Compounds c1 to c6 as hole transport materials.

[Comparative Compounds]
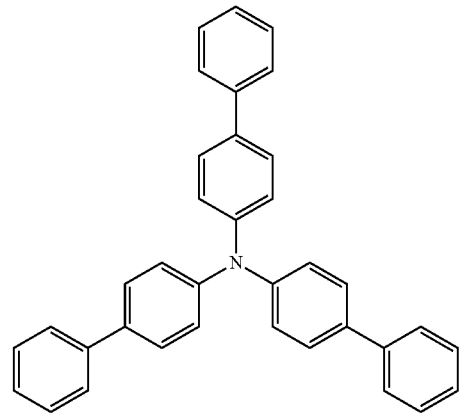
c1
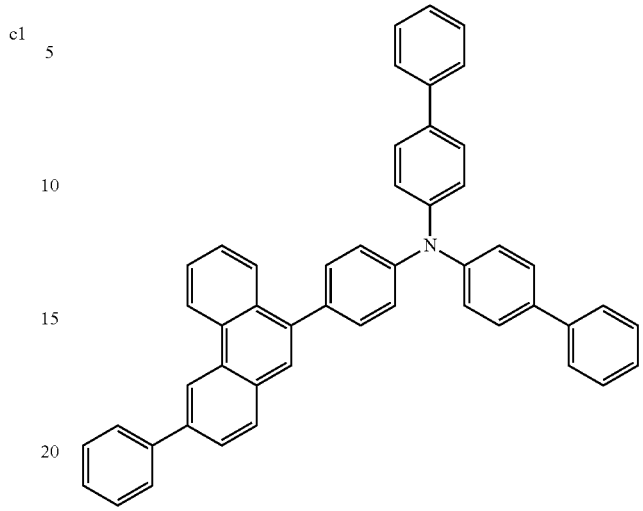
c4
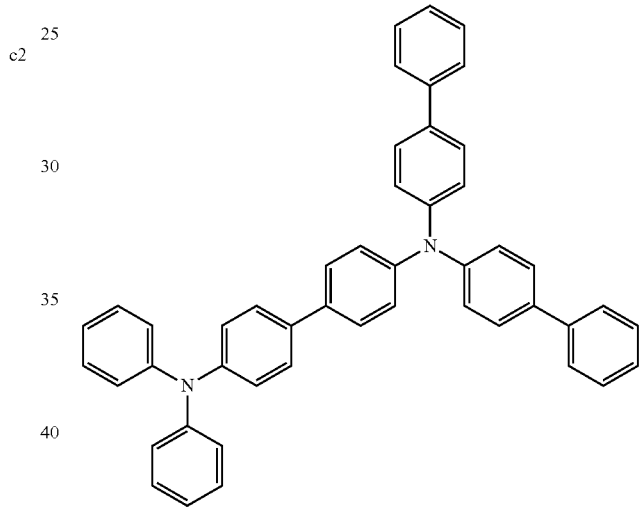
c5
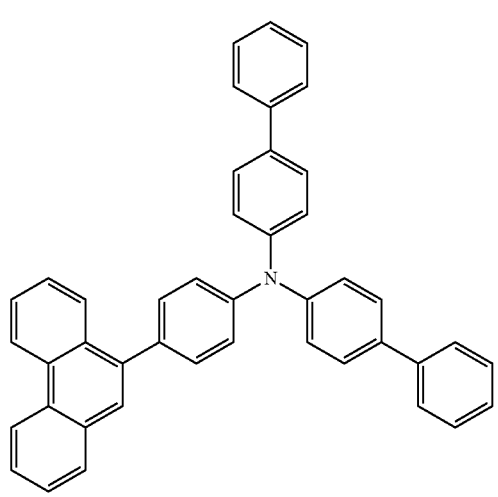
c3
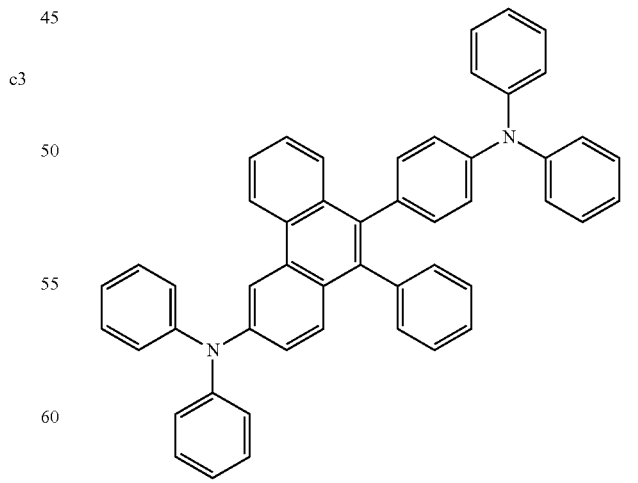
c6
Organic electroluminescence devices according to Examples 1 to 3 and Comparative Examples 1 to 6 were manufactured by forming a first electrode using ITO to a thickness of about 150 nm, a hole injection layer using tris naphthyl phenyl amino triphenylamine (TNATA) to a thickness of about 60 nm, a hole transport layer using the compound according to the example or the comparative example to a thickness of about 30 nm, an emission layer using dinaphthyl anthracene (ADN) doped with 3% tetra-t-butylperylene (TBP) to a thickness of about 25 nm, an electron transport layer using tris(8-hydroxyquinolinato)aluminum ($Alq_3$) to a thickness of about 25 nm, an electron injection layer using LiF to a thickness of about 1 nm, and a second electrode using Al to a thickness of about 100 nm. Each layer was formed by a vacuum deposition method.

Then, the emission efficiency of the organic electroluminescence device thus manufactured was evaluated. The emission efficiency was measured as a relative emission efficiency ratio of each example and comparative example when considering the emission efficiency of an organic electroluminescence device of Comparative Example 3 as 100%.

TABLE 1

| Device Manufacturing Example | Hole Transport Layer Material | Emission Efficiency (Relative Ratio To Comparative Example 3) |
|---|---|---|
| Example 1 | Example Compound 1 | 110% |
| Example 2 | Example Compound 12 | 108% |
| Example 3 | Example Compound 38 | 106% |
| Comparative Example 1 | Comparative Compound c1 | 70% |
| Comparative Example 2 | Comparative Compound c2 | 98% |
| Comparative Example 3 | Comparative Compound c3 | 100% |
| Comparative Example 4 | Comparative Compound c4 | 92% |
| Comparative Example 5 | Comparative Compound c5 | 65% |
| Comparative Example 6 | Comparative Compound c6 | 68% |

Referring to the results of Table 1, emission efficiency was improved for Examples 1 to 3 when compared to that of Comparative Examples 1 to 6. From the results in Table 1, it may be found that organic electroluminescence devices including the compounds according to example embodiments may attain high emission efficiency.

In Examples 1 to 3, a monoamine compound including a phenyl group as an adjacent group to a position where a phenanthryl group and an arylene linker are connected is included. Without being bound by theory, it is believed that a volume near a phenanthryl group in which a LUMO orbital which is related to electron transportation is distributed, is increased, while maintaining amine properties, and the transportation of electrons from an emission layer to a hole transport layer becomes difficult, and thus, the concentration of excitons in the emission layer is increased to increase the emission efficiency.

In Comparative Example 3, a compound in which a phenanthryl group and an amine group are connected via an arylene linker is included, but the phenanthryl group in the compound included in Comparative Example 3 is not substituted with a phenyl group. Accordingly, without being bound by theory, it is believed that blocking effect of electrons transported from an emission layer to a hole transport layer is not attained, and emission efficiency is lower than that of the examples.

In Comparative Example 4, a compound in which a phenyl group is substituted at a phenanthryl group is included, but the phenyl group is not substituted at a position adjacent to a position where the phenanthryl group and an arylene linker are connected, that is, not at the carbon of position 10 of the phenanthryl group, but at the carbon of position 3. Accordingly, without being bound by theory, it is believed that the volume increase at an active position, where a LUMO orbital which is related to electron transportation is distributed, is not attained, and emission efficiency is reduced when compared to that of the examples.

In Comparative Examples 5 and 6, the devices included a diamine compound having a low HOMO energy level, such that hole injection from a hole injection layer to a hole transport layer may be deteriorated. Accordingly, emission efficiency was lower when compared to that of the examples.

DEVICE MANUFACTURING EXAMPLES 2

Organic electroluminescence devices according to Examples 4 to 12 were manufactured using Compounds 1, 11, 12, 16, 38, 73, 103, 104, and 122 as second hole transport materials.

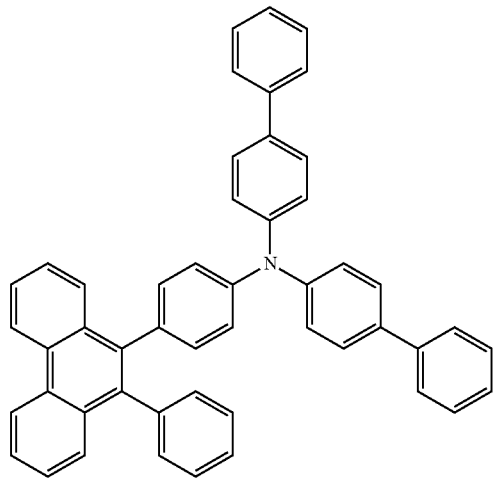

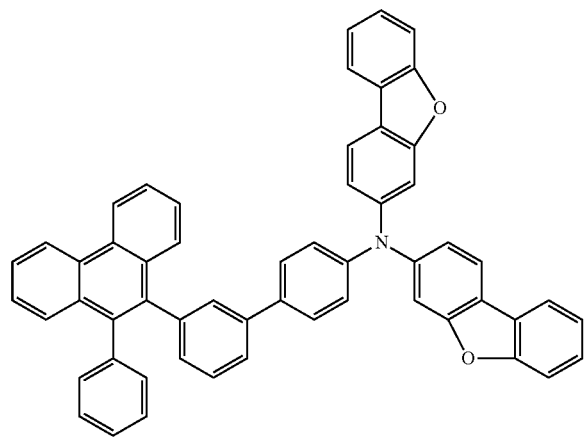
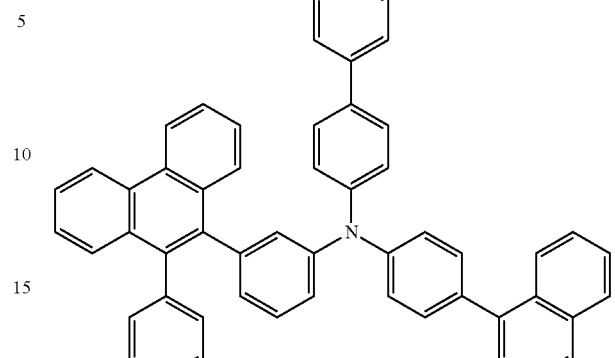
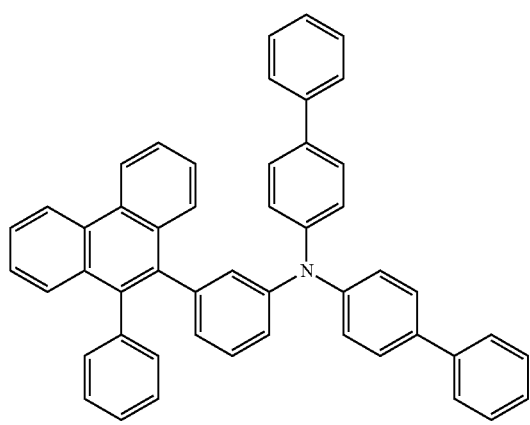
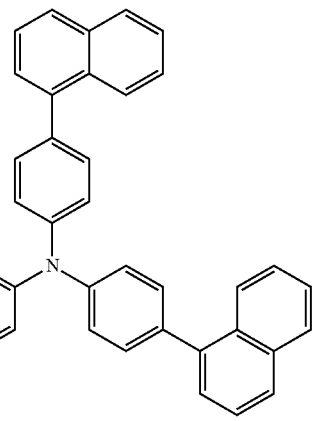
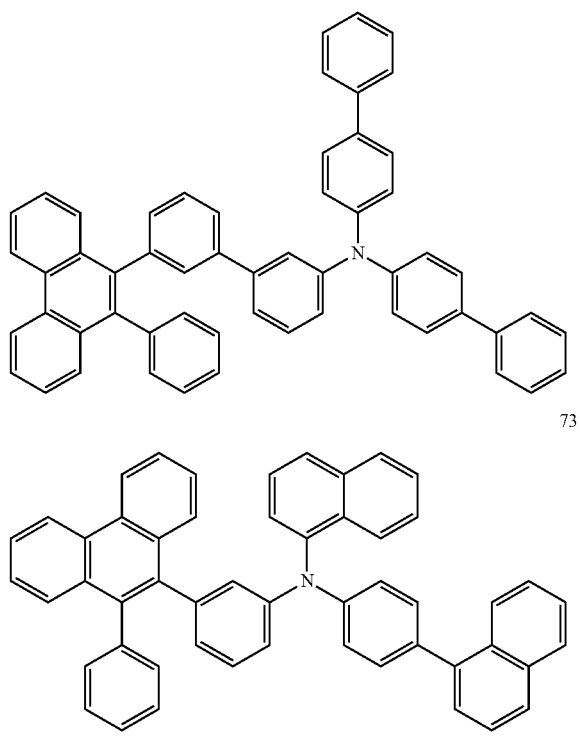
Organic electroluminescence devices according to Comparative Examples 7 to 15 were manufactured using Comparative Compounds c1 to c9 as hole transport materials.

[Comparative Compounds]
c1
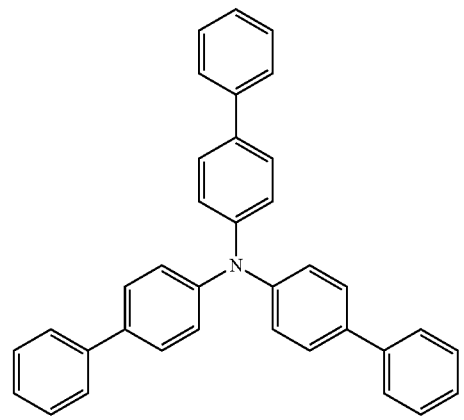
c2
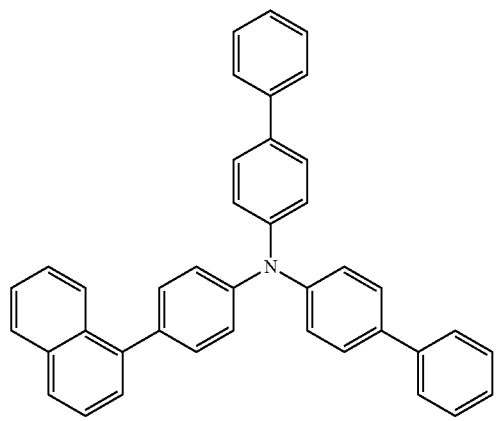
c3
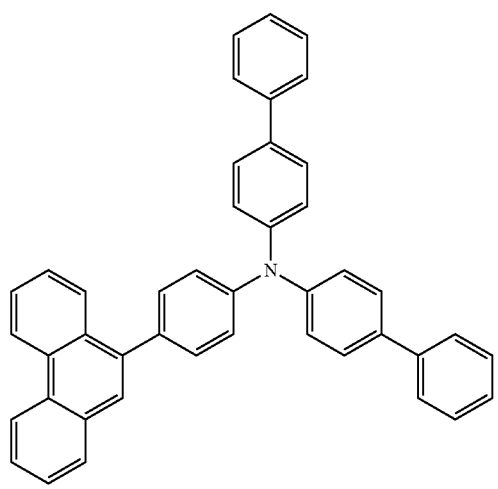
c4
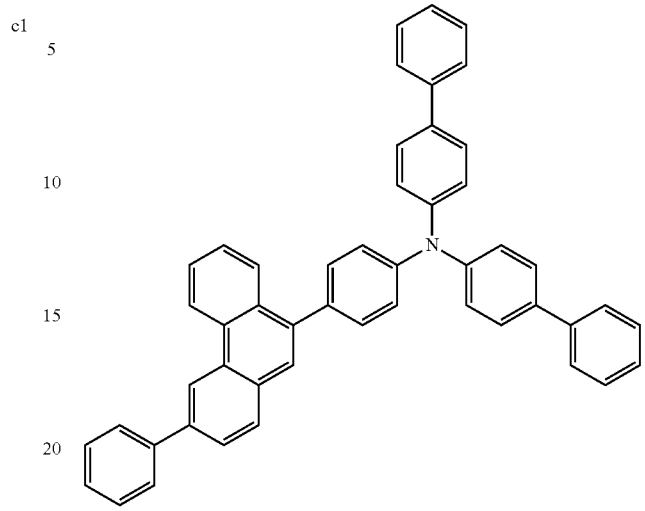
c5
c6
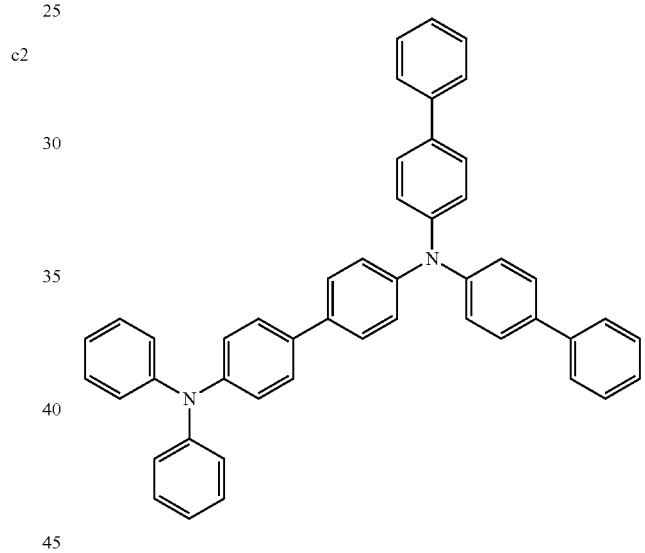

-continued

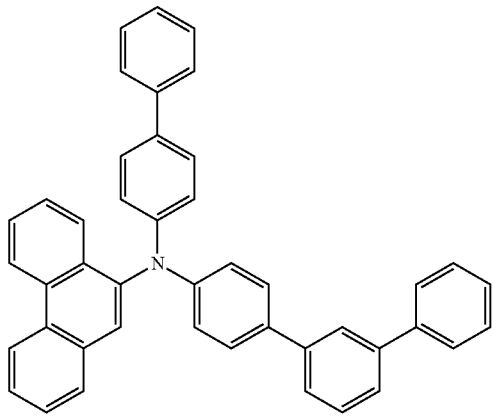

c7

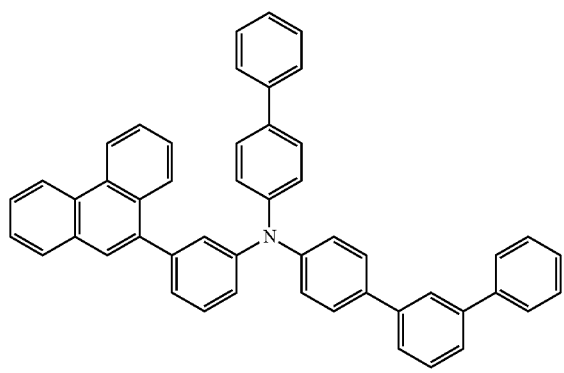

c8

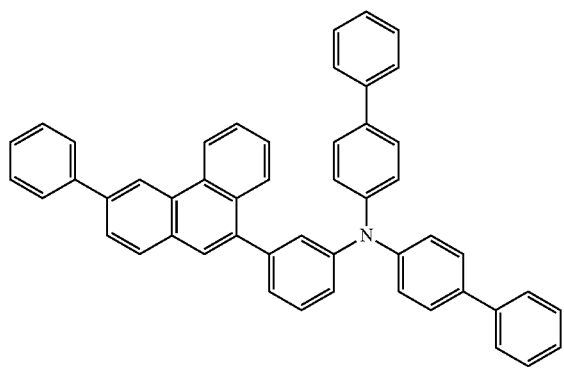

c9

Organic electroluminescence devices according to Examples 4 to 11 and Comparative Examples 7 to 15 were manufactured by forming a first electrode using ITO to a thickness of about 150 nm, a hole injection layer using dipyrazino[2,3-f:2',3'-h]quinoxaline-2,3,6,7,10,11-hexacarbonitrile (HAT-CN) to a thickness of about 10 nm, a first hole transport layer using N-([1,1'-biphenyl]-4-yl)-9,9-dimethyl-N-(4-(9-phenyl-9H-carbazol-3-yl)phenyl)-9H-fluoren-2-amine to a thickness of about 70 nm, a second hole transport layer using the example compounds or comparative compounds to a thickness of about 10 nm, an emission layer using (9-(4-(naphthalene-1-yl)phenyl)-10-perdeuterophenyl)anthracene doped with 3% $N^1,N^6$-di(naphthalene-1-yl)-$N^1,N^6$-diphenylpyrene-1,6-diamine to a thickness of about 25 nm, an electron transport layer using tris(8-hydroxyquinolinato)aluminum ($Alq_3$) to a thickness of about 25 nm, an electron injection layer using LiF to a thickness of about 1 nm, and a second electrode using Al to a thickness of about 100 nm. Each layer and the second electrode were formed by a vacuum deposition method.

Then, the emission efficiency of the organic electroluminescence device thus manufactured was evaluated. The emission efficiency was measured as a relative emission efficiency ratio of each example and comparative example when considering the emission efficiency of an organic electroluminescence device of Comparative Example 9 as 100%.

TABLE 2

| Device Manufacturing Example | Second Hole Transport Layer | Emission Efficiency (Relative Ratio To Comparative Example 9) |
|---|---|---|
| Example 4 | Example Compound 1 | 110% |
| Example 5 | Example Compound 11 | 110% |
| Example 6 | Example Compound 12 | 110% |
| Example 7 | Example Compound 16 | 113% |
| Example 8 | Example Compound 38 | 108% |
| Example 9 | Example Compound 73 | 119% |
| Example 10 | Example Compound 103 | 113% |
| Example 11 | Example Compound 104 | 121% |
| Example 12 | Example Compound 122 | 113% |
| Comparative Example 7 | Comparative Compound c1 | 80% |
| Comparative Example 8 | Comparative Compound c2 | 95% |
| Comparative Example 9 | Comparative Compound c3 | 100% |
| Comparative Example 10 | Comparative Compound c4 | 94% |
| Comparative Example 11 | Comparative Compound c5 | 60% |
| Comparative Example 12 | Comparative Compound c6 | 63% |
| Comparative Example 13 | Comparative Compound c7 | 95% |
| Comparative Example 14 | Comparative Compound c8 | 101% |
| Comparative Example 15 | Comparative Compound c9 | 99% |

Referring to the results of Table 2, it may be found that emission efficiency was improved for Examples 4 to 12 when compared to that of Comparative Examples 7 to 15. From the results in Table 2, it may be found that organic electroluminescence devices including the compounds according to example embodiments may attain high emission efficiency.

In Examples 4 to 12, a monoamine compound including a phenyl group as an adjacent group to a position where a phenanthryl group and an arylene linker are connected is included. Without being bound by theory, it is believed that a volume near a phenanthryl group in which a LUMO orbital which is related to electron transportation is distributed, is increased, while maintaining amine properties, and the transportation of electrons from an emission layer to a hole transport layer becomes difficult, and thus, the concentration of excitons in the emission layer is increased to increase the emission efficiency.

In Comparative Examples 9, 13, and 14, a compound in which a phenanthryl group and an amine group are connected via an arylene linker is included, but the phenanthryl group in the compounds included in Comparative Examples 9, 13, and 14 is not substituted with a phenyl group. Accordingly, without being bound by theory, it is believed that blocking effect of electrons transported from an emission layer to a hole transport layer is not attained, and emission efficiency is lower than that of the examples.

In Comparative Examples 10 and 15, a compound in which a phenyl group is substituted at a phenanthryl group is included, but the phenyl group is not substituted at an adjacent position to a position where the phenanthryl group and an arylene linker are connected, that is, not at the carbon of position 10 of the phenanthryl group, but at the carbon of position 3. Accordingly, without being bound by theory, it is believed that the volume increase at an active position, where a LUMO orbital which is related to electron transportation is distributed, is not attained, and emission efficiency is reduced when compared to that of the examples.

In Comparative Examples 11 and 12, the devices included a diamine compound having a low HOMO energy level, such that hole injection from a hole injection layer to a hole transport layer may be deteriorated. Accordingly, emission efficiency was lower when compared to that of the examples.

By way of summation and review, an organic electroluminescence device may be, for example, an organic device having a first electrode, a hole transport layer disposed on the first electrode, an emission layer disposed on the hole transport layer, an electron transport layer disposed on the emission layer, and a second electrode disposed on the electron transport layer. Holes are injected from the first electrode, and the injected holes move via the hole transport layer and injected into the emission layer. Meanwhile, electrons are injected from the second electrode, and the injected electrons move via the electron transport layer and injected into the emission layer. By recombining the injected holes and electrons into the emission layer, excitons are generated in the emission layer. An organic electroluminescence device emits light using light emitted during the transition of the excitons back to a ground state. The configuration of an organic electroluminescence device is not limited thereto, and various modifications may be possible.

As described above, a monoamine compound according to an example embodiment may be used as a material for an organic electroluminescence device. The organic electroluminescence device including the monoamine compound according to an example embodiment may attain high emission efficiency. The present disclosure provides a monoamine compound used in an organic electroluminescence device having high emission efficiency. The present disclosure also provides an organic electroluminescence device having high emission efficiency Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A monoamine compound represented by the following Formula 1:

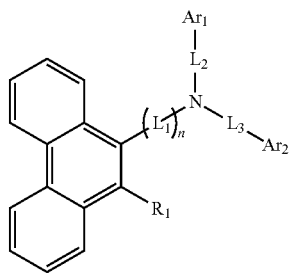

[Formula 1]

wherein $L_1$ is a substituted or unsubstituted arylene group having 6 to 30 carbon atoms for forming a ring, or a substituted or unsubstituted heteroarylene group having 2 to 30 carbon atoms for forming a ring, n is 1 or 2, $L_2$ and $L_3$ are each independently a direct linkage, a substituted or unsubstituted arylene group having 6 to 30 carbon atoms for forming a ring, or a substituted or unsubstituted heteroarylene group having 2 to 30 carbon atoms for forming a ring, $R_1$ is a substituted or unsubstituted alkyl group having 1 to 10 carbon atoms, a substituted or unsubstituted aryl group having 6 to 30 carbon atoms for forming a ring, a substituted or unsubstituted heteroaryl group having 2 to 30 carbon atoms for forming a ring, or a substituted or unsubstituted aryl silyl group, when R1 is substituted, the substituent is a deuterium atom, a cyano group, a substituted or unsubstituted alkyl group having 1 to 10 carbon atoms, or a substituted or unsubstituted aryl group having 6 to 30 carbon atoms for forming a ring, Ar1 and Ar2 are each independently a substituted or unsubstituted aryl group having 6 to 30 carbon atoms for forming a ring, a substituted or unsubstituted dibenzofuranyl group, a substituted or unsubstituted dibenzothiophenyl group, a substituted or unsubstituted benzonaphthofuranyl group, or a substituted or unsubstituted benzonaphthothiophenyl group, and wherein when at least one of $L_2$, $L_3$, $Ar_1$ and $Ar_2$ is substituted with a heterocycle, the heterocycle does not include N as a heteroatom.

2. The monoamine compound as claimed in claim 1, wherein the monoamine compound represented by Formula 1 is represented by the following Formula 2-1:

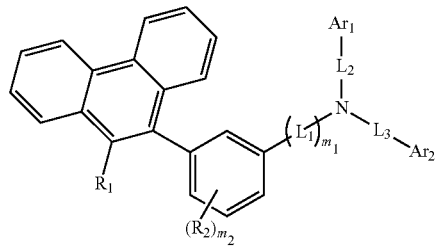

[Formula 2-1]

in Formula 2-1, $m_1$ is 0 or 1, $m_2$ is an integer of 0 to 2, $R_2$ is a hydrogen atom, a deuterium atom, a substituted or unsubstituted alkyl group having 1 to 10 carbon atoms, a substituted or unsubstituted aryl group having 6 to 30 carbon atoms for forming a ring, a substituted or unsubstituted heteroaryl group having 2 to 30 carbon atoms for forming a ring, or a substituted or unsubstituted aryl silyl group, or combines with an adjacent group to form a ring, and $Ar_1$, $Ar_2$, $L_1$, $L_2$, $L_3$, and $R_1$ are the same as defined for Formula 1.

3. The monoamine compound as claimed in claim 2, wherein the monoamine compound represented by Formula 2-1 is represented by one of the following Formulae 2-1-1 to 2-1-3:

[Formula 2-1-1]

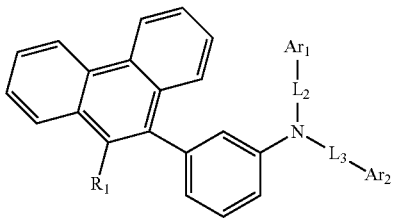

[Formula 2-1-2]

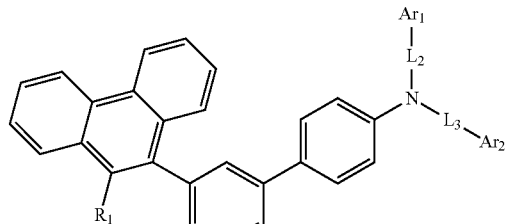

[Formula 2-1-3]

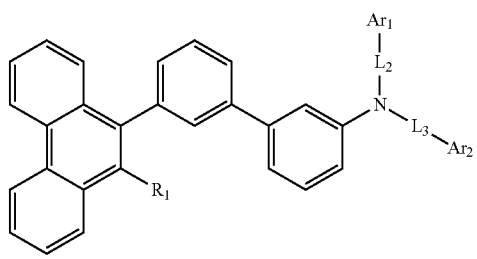

in Formulae 2-1-1 to 2-1-3, $Ar_1$ and $Ar_2$, $L_2$ and $L_3$, and $R_1$ are the same as defined for Formula 1.

4. The monoamine compound of claim 3, wherein $R_1$ is a substituted or unsubstituted phenyl group, $L_3$ is a substituted or unsubstituted phenylene group, and $Ar_2$ is a substituted or unsubstituted naphthyl group.

5. The monoamine compound of claim 4, wherein $L_2$ is a substituted or unsubstituted phenylene group, and $Ar_1$ is a substituted or unsubstituted phenyl group.

6. The monoamine compound of claim 4, wherein $L_2$ is a direct linkage, and $Ar_1$ is a substituted or unsubstituted dibenzofuranyl group.

7. The monoamine compound as claimed in claim 1, wherein the monoamine compound represented by Formula 1 is represented by the following Formula 2-2:

[Formula 2-2]

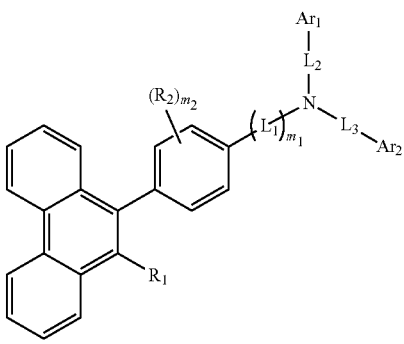

in Formula 2-2, $m_1$ is 0 or 1, $m_2$ is an integer of 0 to 2, $R_2$ is a hydrogen atom, a deuterium atom, a substituted or unsubstituted alkyl group having 1 to 10 carbon atoms, a substituted or unsubstituted aryl group having 6 to 30 carbon atoms for forming a ring, a substituted or unsubstituted heteroaryl group having 2 to 30 carbon atoms for forming a ring, or a substituted or unsubstituted aryl silyl group, or combines with an adjacent group to form a ring, and $Ar_1$, $Ar_2$, $L_1$, $L_2$, $L_3$, and $R_1$ are the same as defined for Formula 1.

8. The monoamine compound as claimed in claim 4, wherein the monoamine compound represented by Formula 2-2 is represented by one of the following Formulae 2-2-1 to 2-2-3:

[Formula 2-2-1]

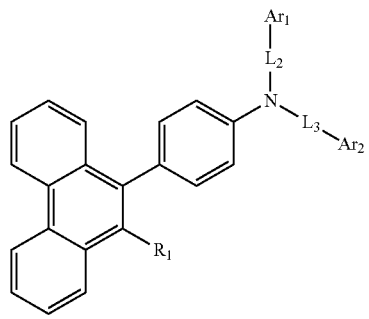

[Formula 2-2-2]

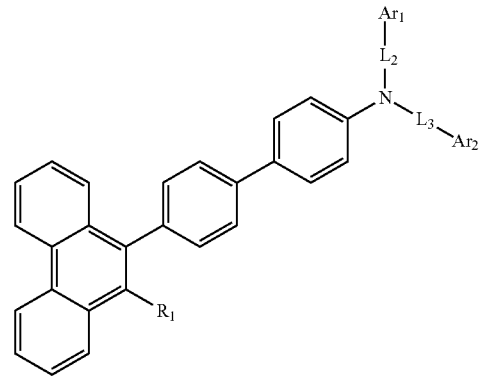

-continued

[Formula 2-2-3]

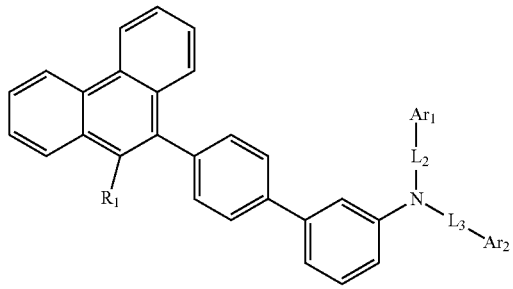

in Formulae 2-2-1 to 2-2-3, $Ar_1$ and $Ar_2$, $L_2$ and $L_3$ and $R_1$ are the same as defined for Formula 1.

9. The monoamine compound as claimed in claim 1, wherein $L_1$ is a substituted or unsubstituted phenylene group, a substituted or unsubstituted divalent biphenyl group, or a substituted or unsubstituted naphthylene group.

10. The monoamine compound as claimed in claim 1, wherein $R_1$ is a substituted or unsubstituted phenyl group, a substituted or unsubstituted naphthyl group, a substituted or unsubstituted biphenyl group, or a substituted or unsubstituted nitrogen-containing heteroaryl group.

11. The monoamine compound as claimed in claim 1, wherein $Ar_1$ and $Ar_2$ are each independently a substituted or unsubstituted phenyl group, a substituted or unsubstituted biphenyl group, a substituted or unsubstituted terphenyl group, a substituted or unsubstituted naphthyl group, a substituted or unsubstituted phenanthryl group, or a substituted or unsubstituted fluorenyl group.

12. The monoamine compound as claimed in claim 1, wherein $Ar_1$ and $Ar_2$ are each independently represented by the following Formula 3:

[Formula 3]

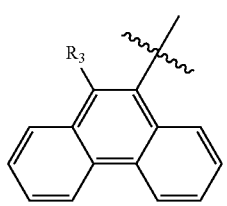

in case $Ar_1$ and $Ar_2$ are each independently represented by Formula 3, in Formula 1, $L_2$ and $L_3$ are each independently a substituted or unsubstituted arylene group having 6 to 30 carbon atoms for forming a ring, or a substituted or unsubstituted heteroarylene group having 2 to 30 carbon atoms for forming a ring, in Formula 3, $R_3$ is a substituted or unsubstituted alkyl group having 1 to 10 carbon atoms, a substituted or unsubstituted aryl group having 6 to 30 carbon atoms for forming a ring, a substituted or unsubstituted heteroaryl group having 2 to 30 carbon atoms for forming a ring, or a substituted or unsubstituted aryl silyl group.

13. The monoamine compound as claimed in claim 1, wherein $Ar_1$ and $Ar_2$ are each independently represented by the following Formula 4:

[Formula 4]

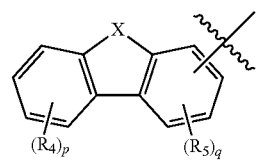

in Formula 4,

X is O or S, $R_4$ and $R_5$ are each independently a hydrogen atom, a deuterium atom, a substituted or unsubstituted alkyl group having 1 to 10 carbon atoms, a substituted or unsubstituted aryl group having 6 to 30 carbon atoms for forming a ring, a substituted or unsubstituted heteroaryl group having 2 to 30 carbon atoms for forming a ring, or a substituted or unsubstituted aryl silyl group, p is an integer of 0 to 4, and q is an integer of 0 to 3.

14. The monoamine compound as claimed in claim 1, wherein $L_2$ and $L_3$ are each independently a direct linkage, a substituted or unsubstituted phenylene group, a substituted or unsubstituted divalent biphenyl group, or a substituted or unsubstituted naphthylene group.

15. A monoamine compound selected from the following Compound Group 1:

[Compound Group 1]

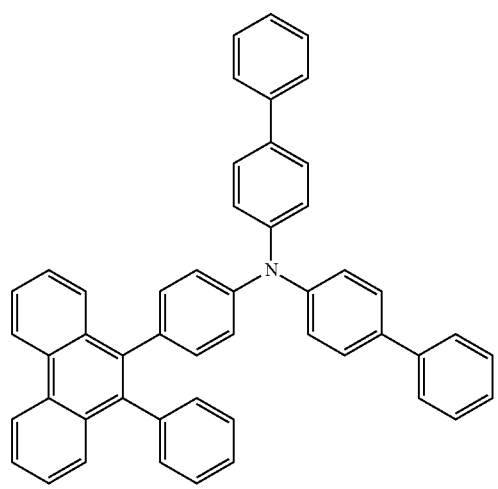

1

-continued
2
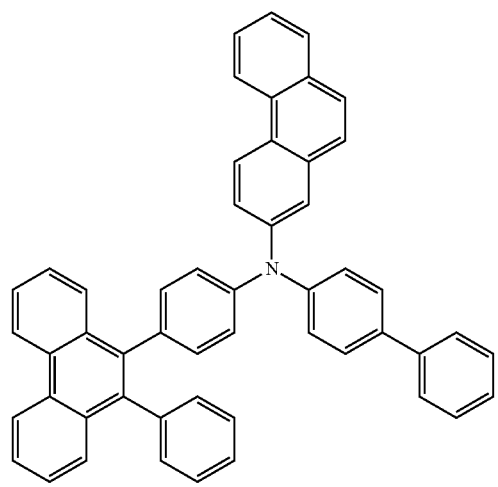
3
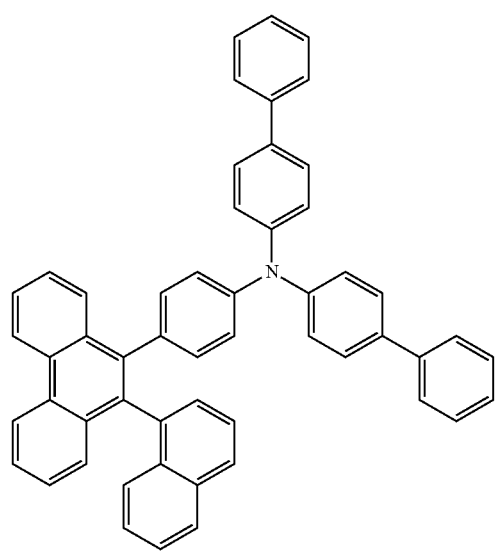
4
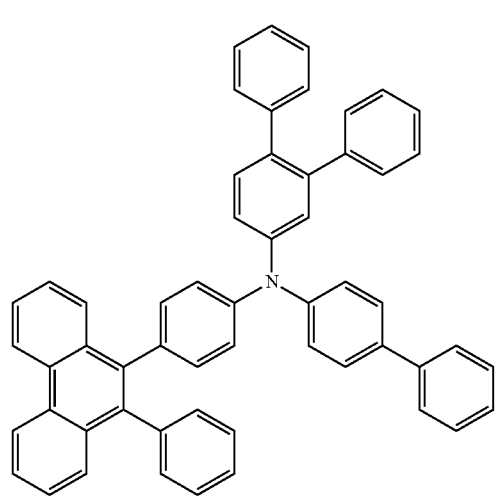
-continued
5
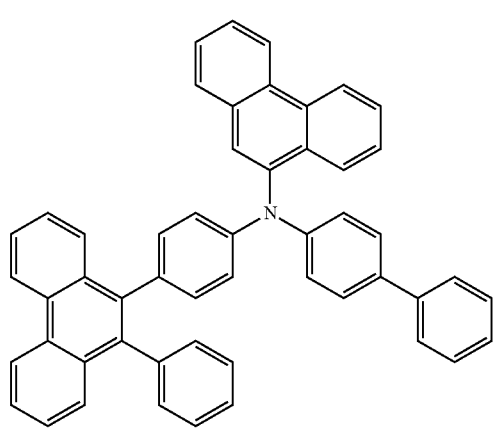
6
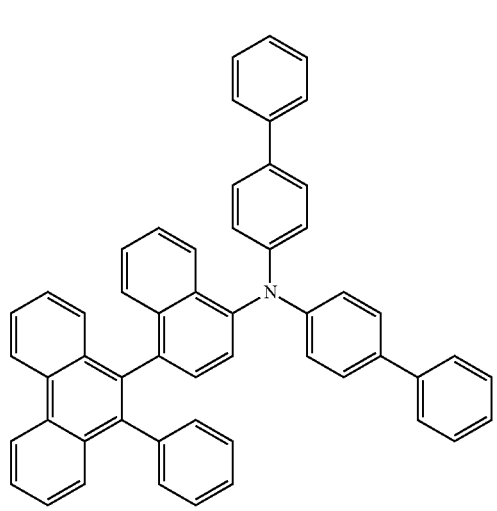
7
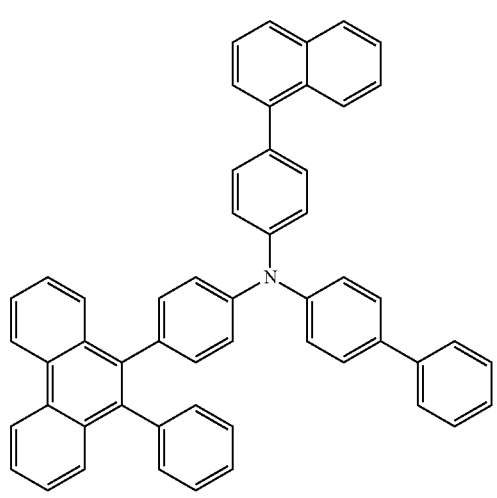

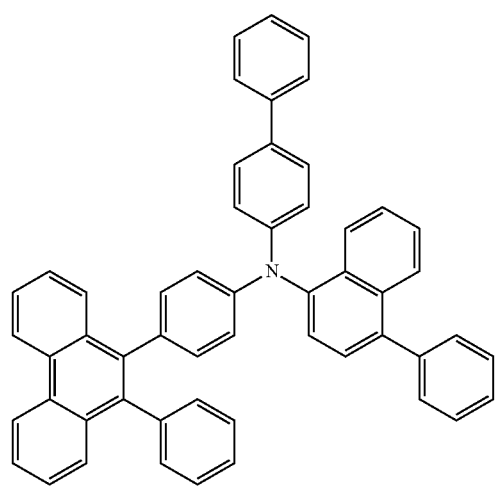
8
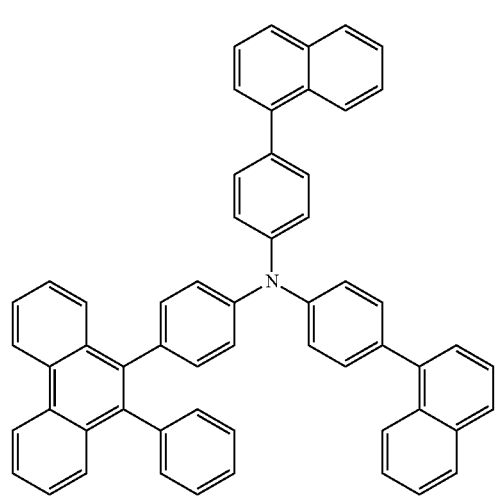
9
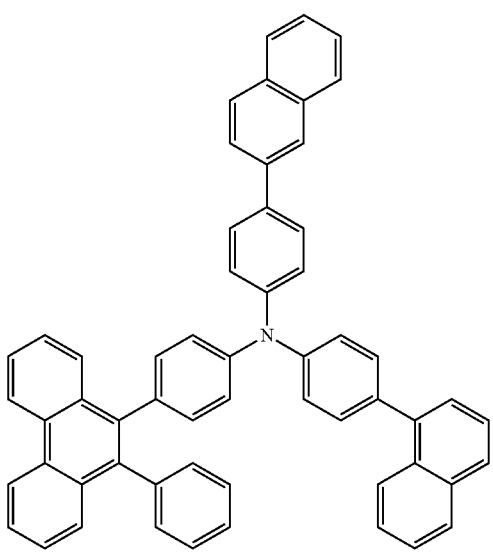
10
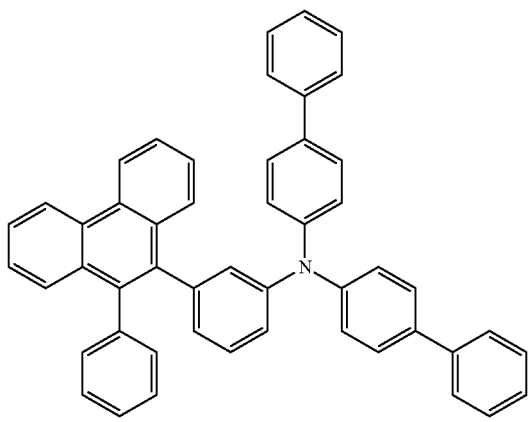
11
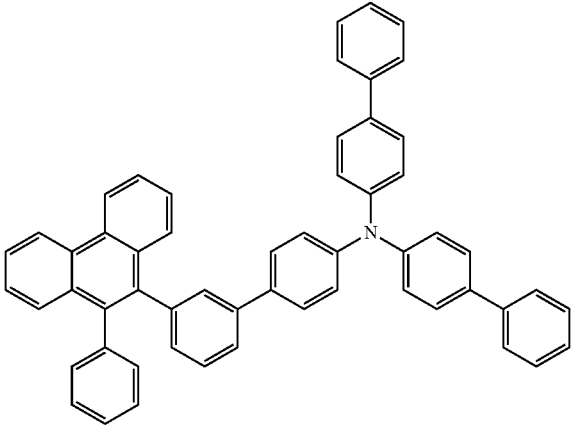
12
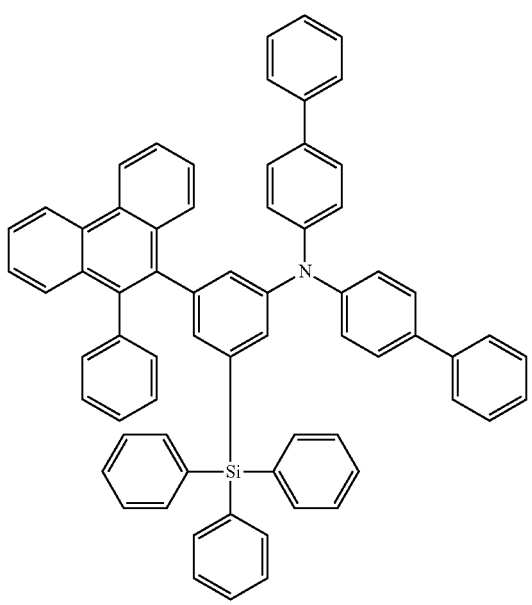
13

14
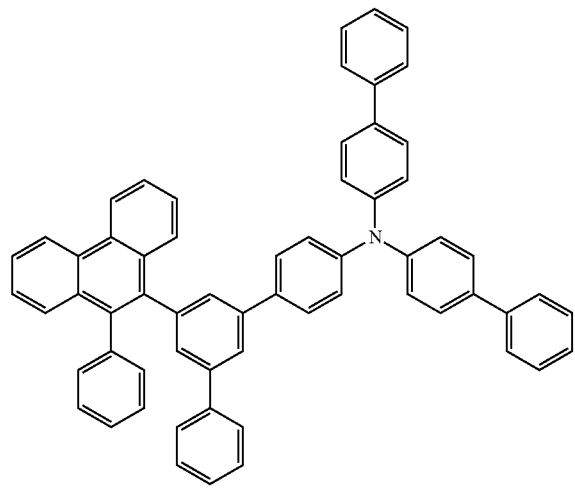
15
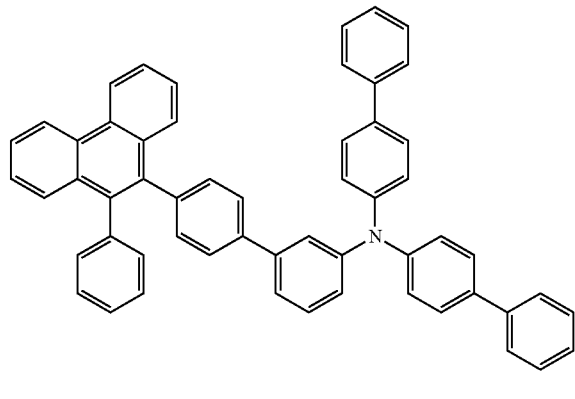
16
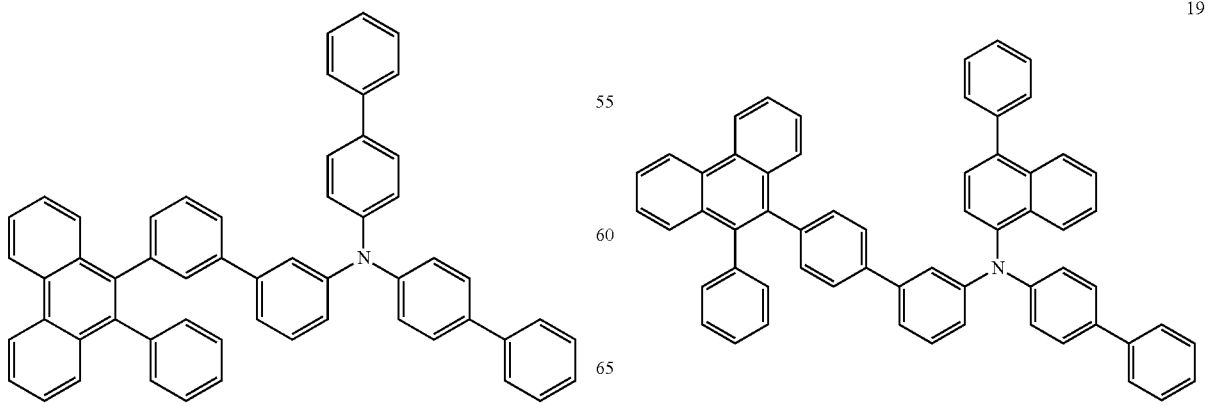
17
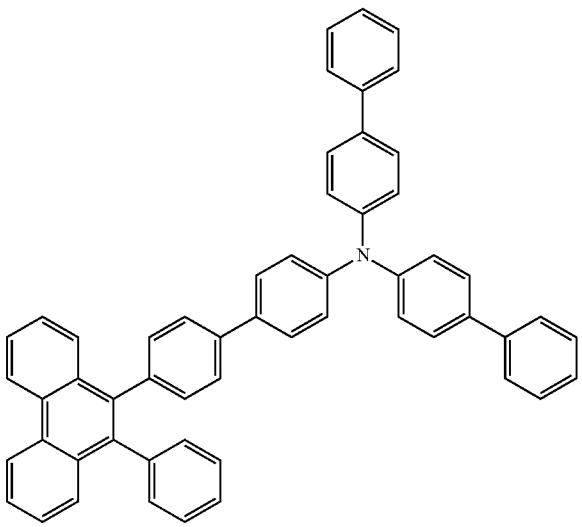
18
19

101
-continued
20
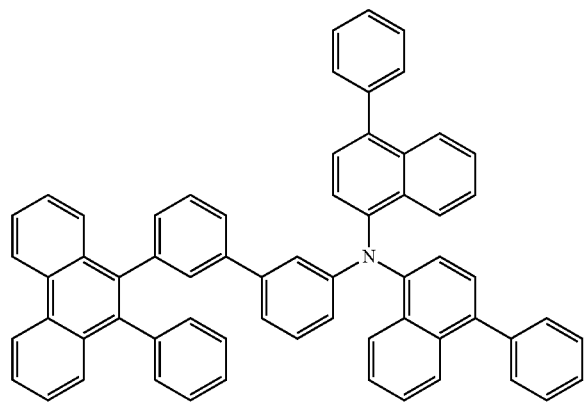
21
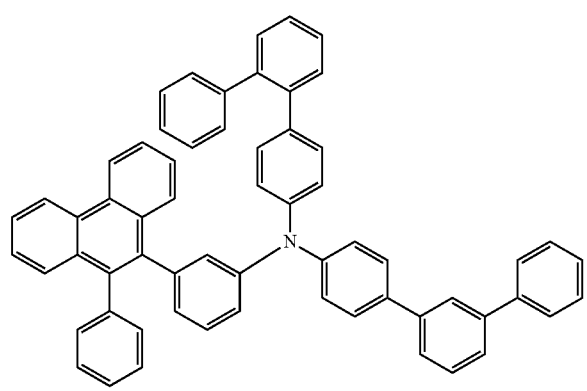
22
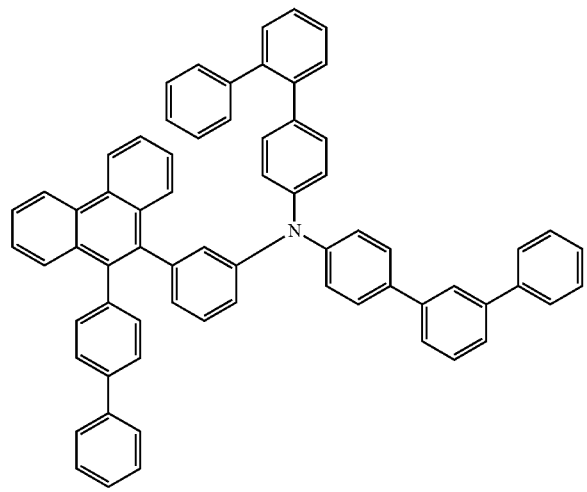
102
-continued
23
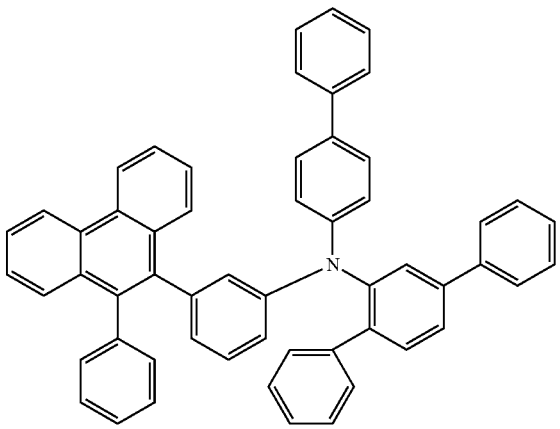
24
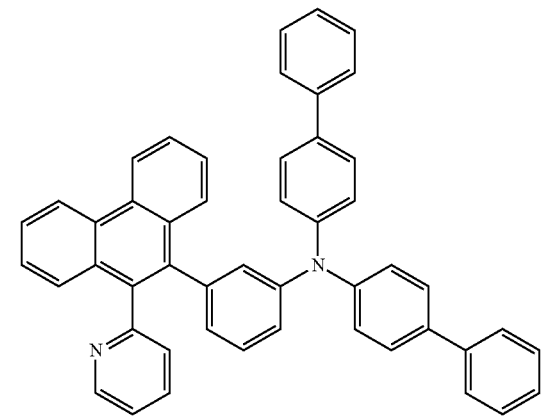
25
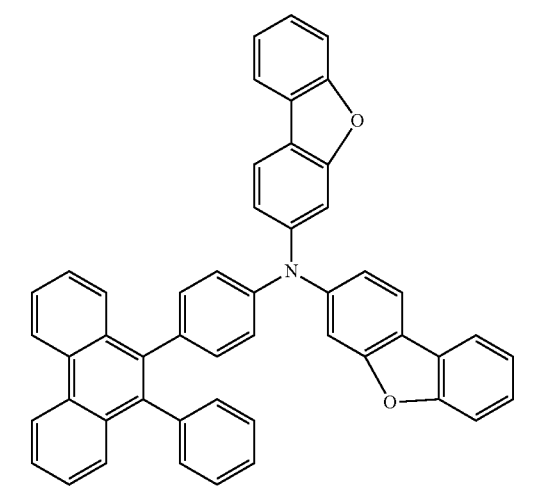

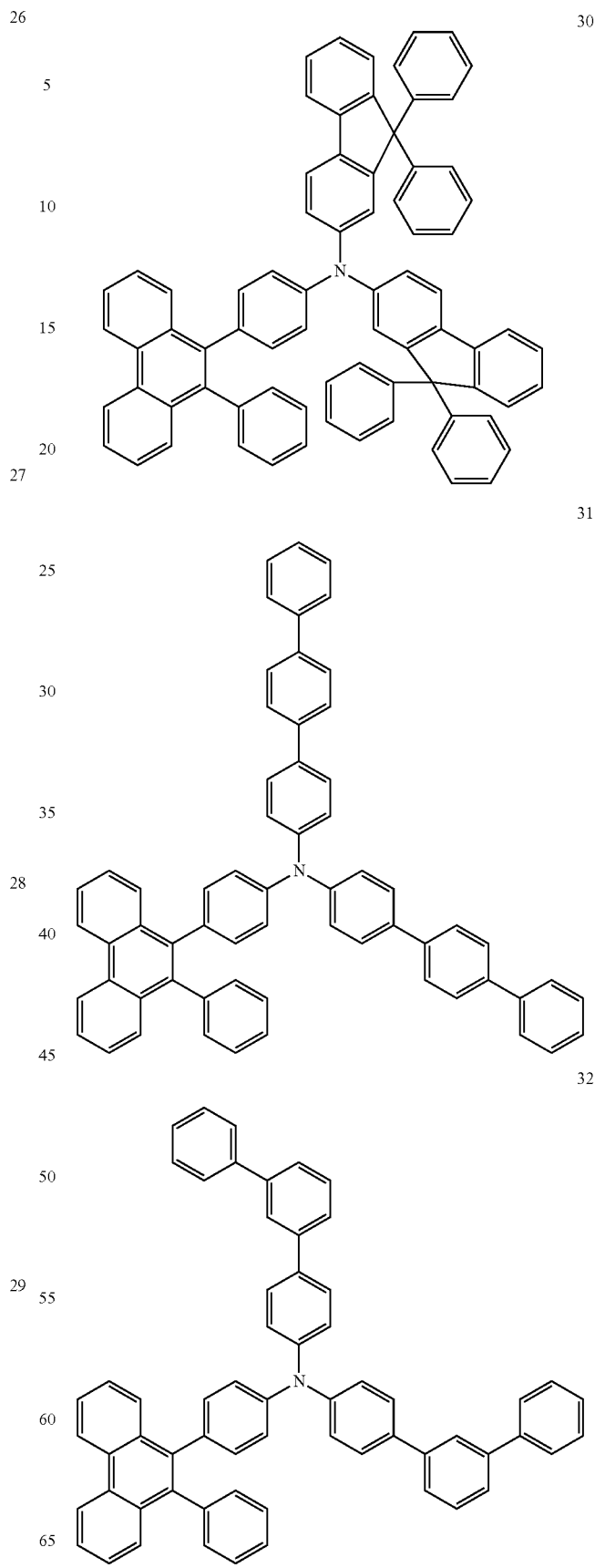

33
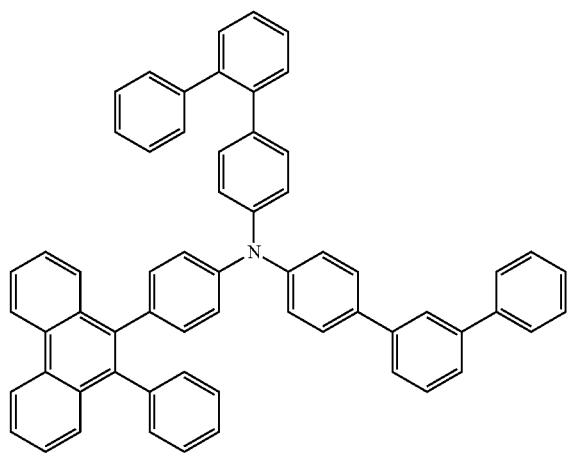
34
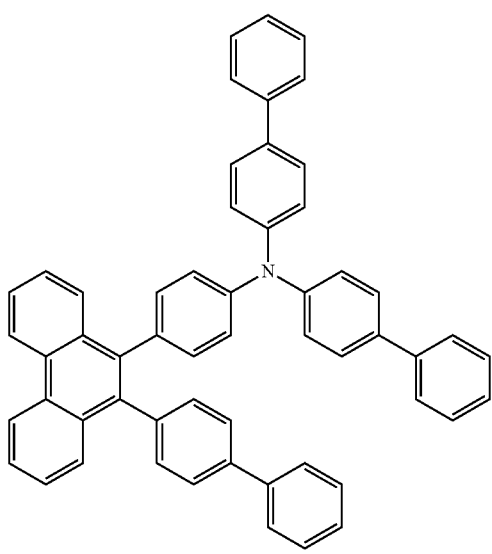
35
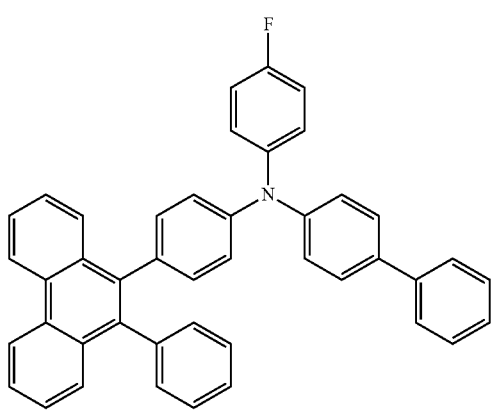
36
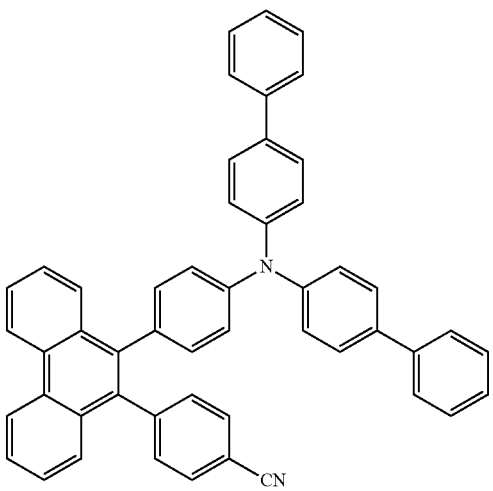
37
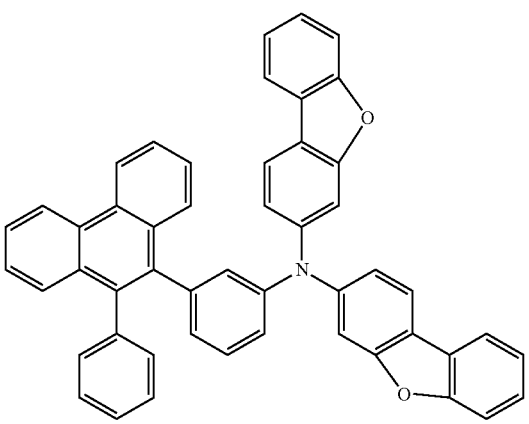
38
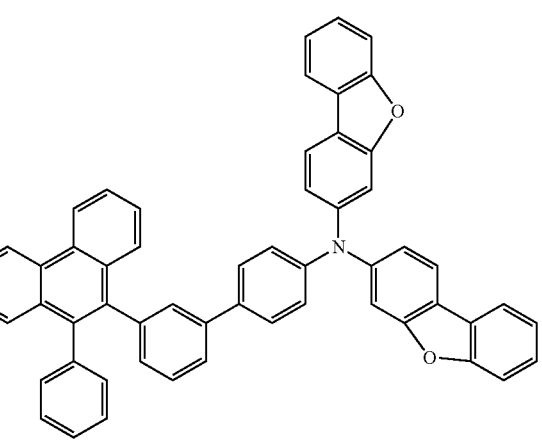

107
-continued
39
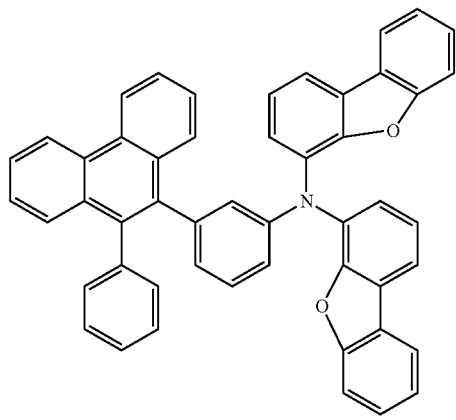
40
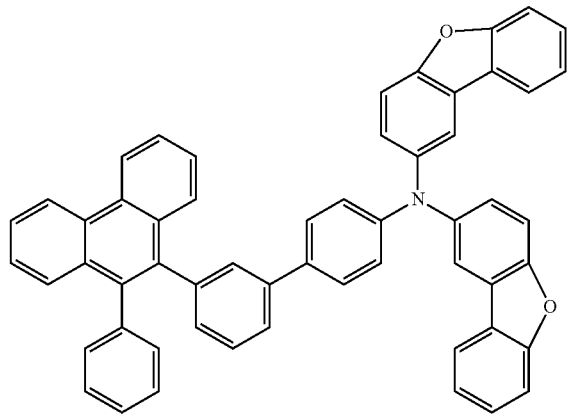
41
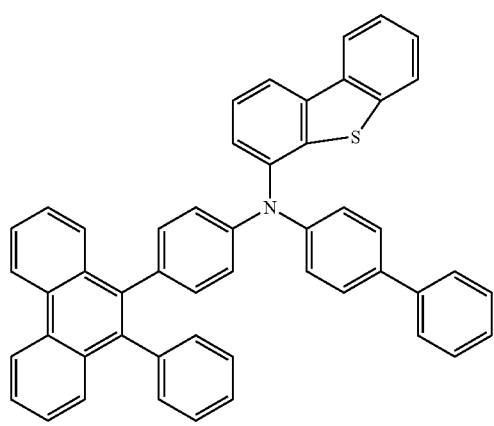
108
-continued
42
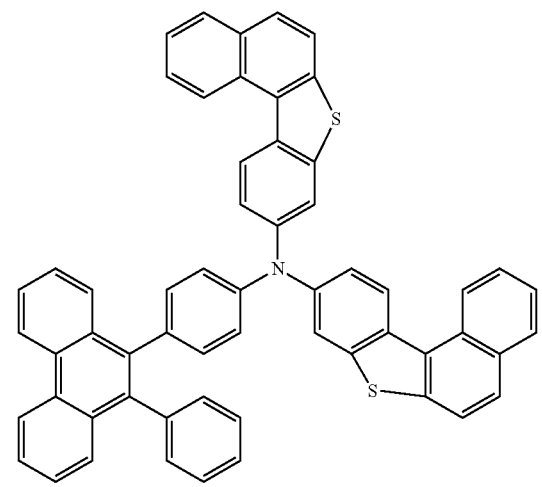
43
44
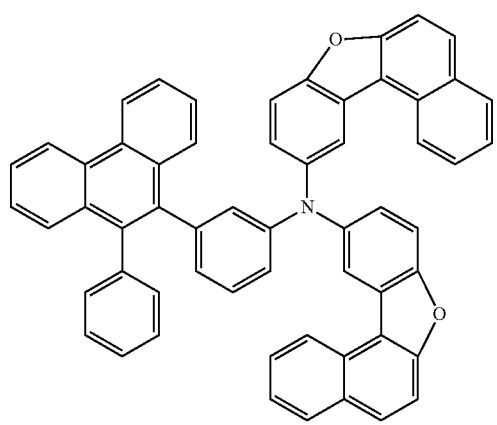

45
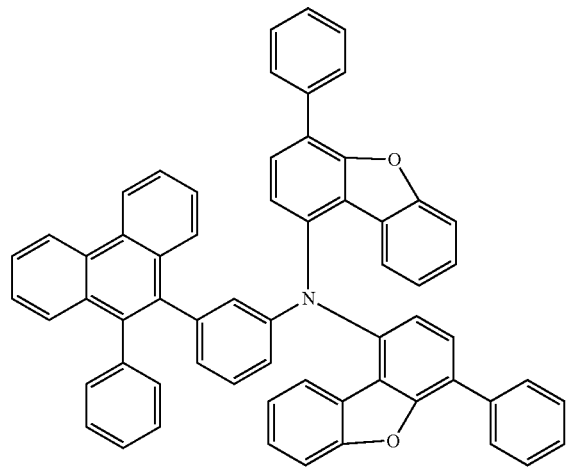
46
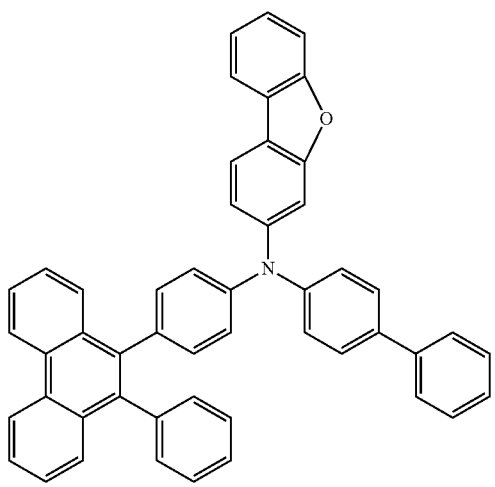
47
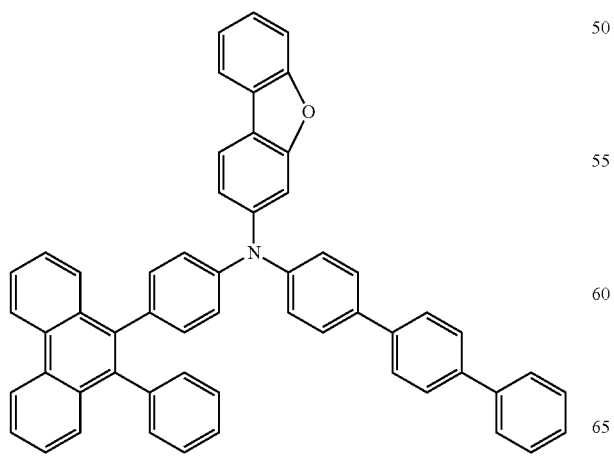
48
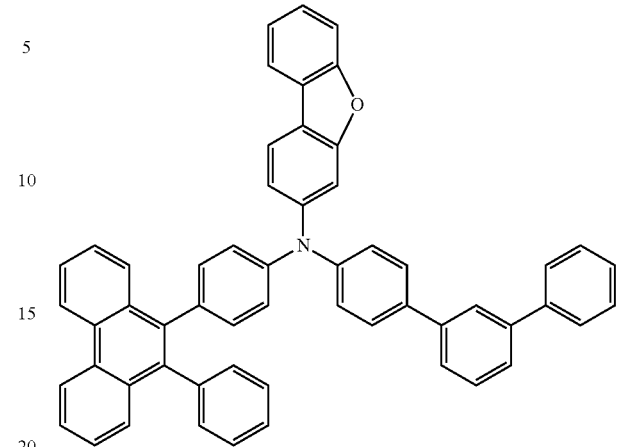
49
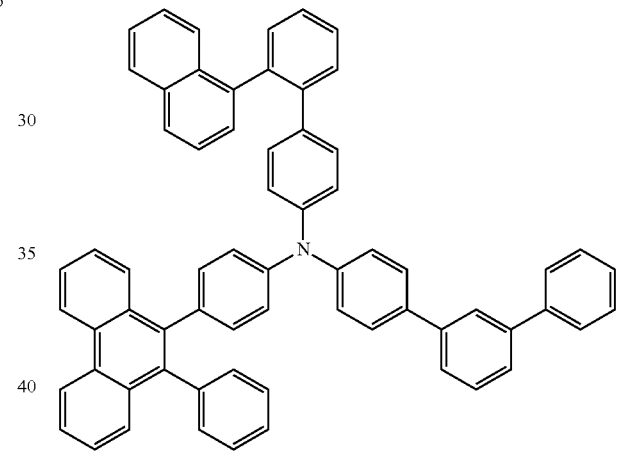
50
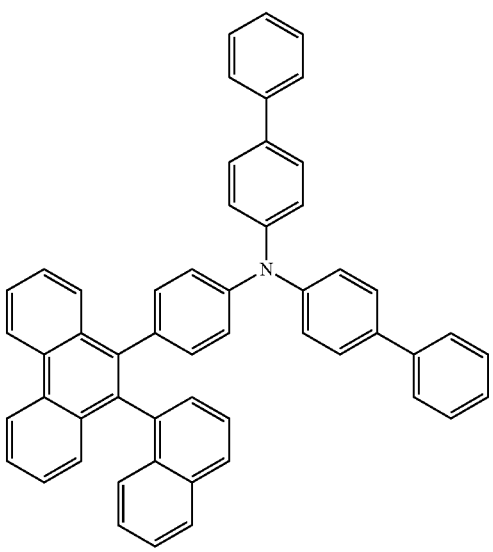

51
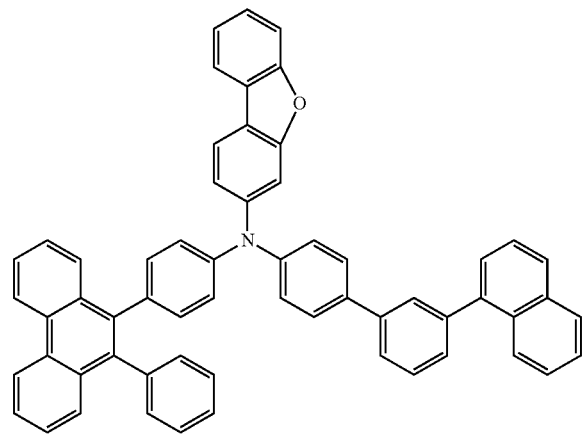
52
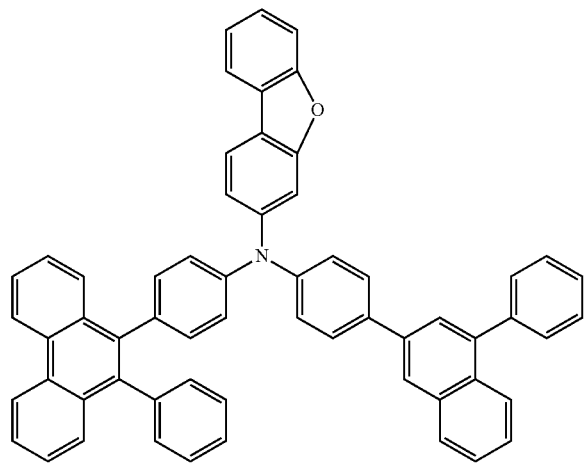
53
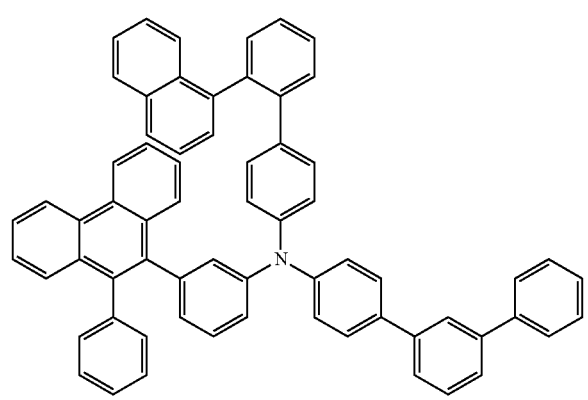
54
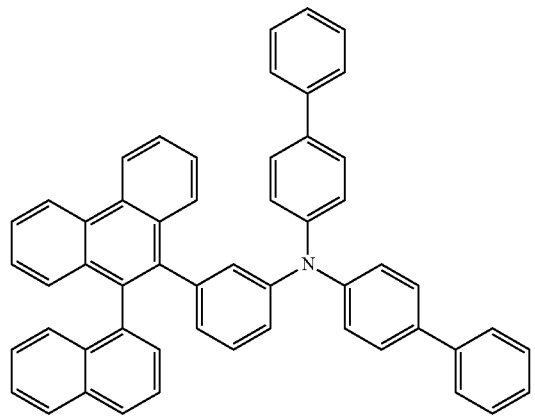
55
56
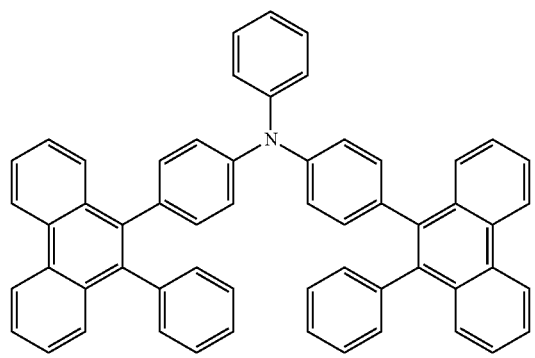

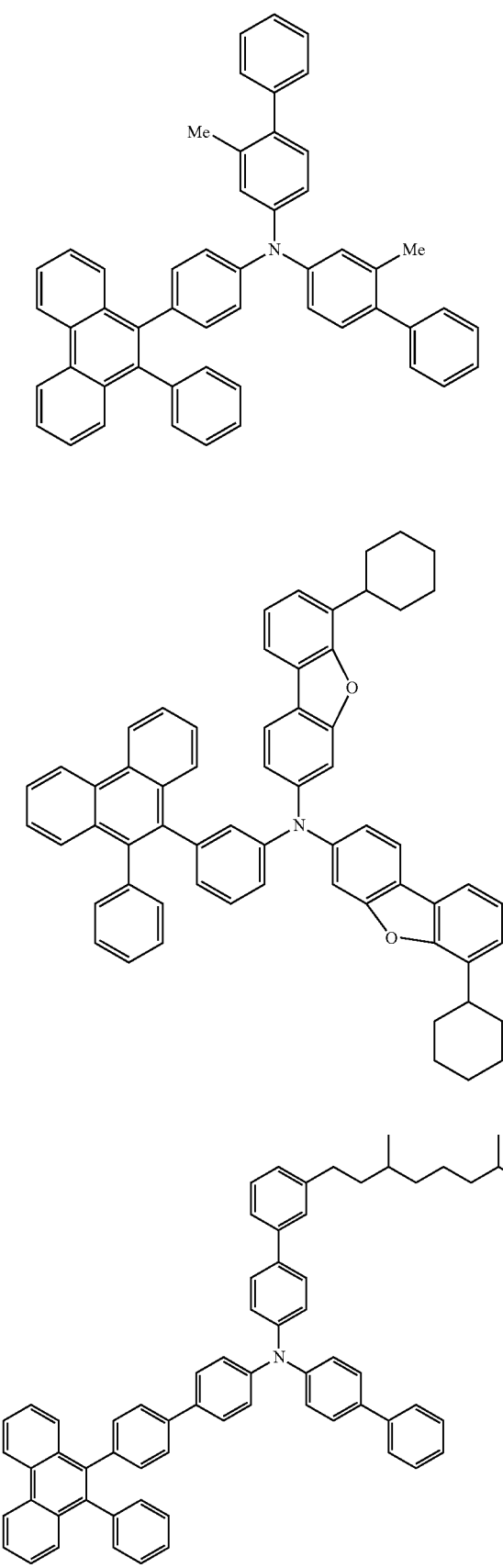
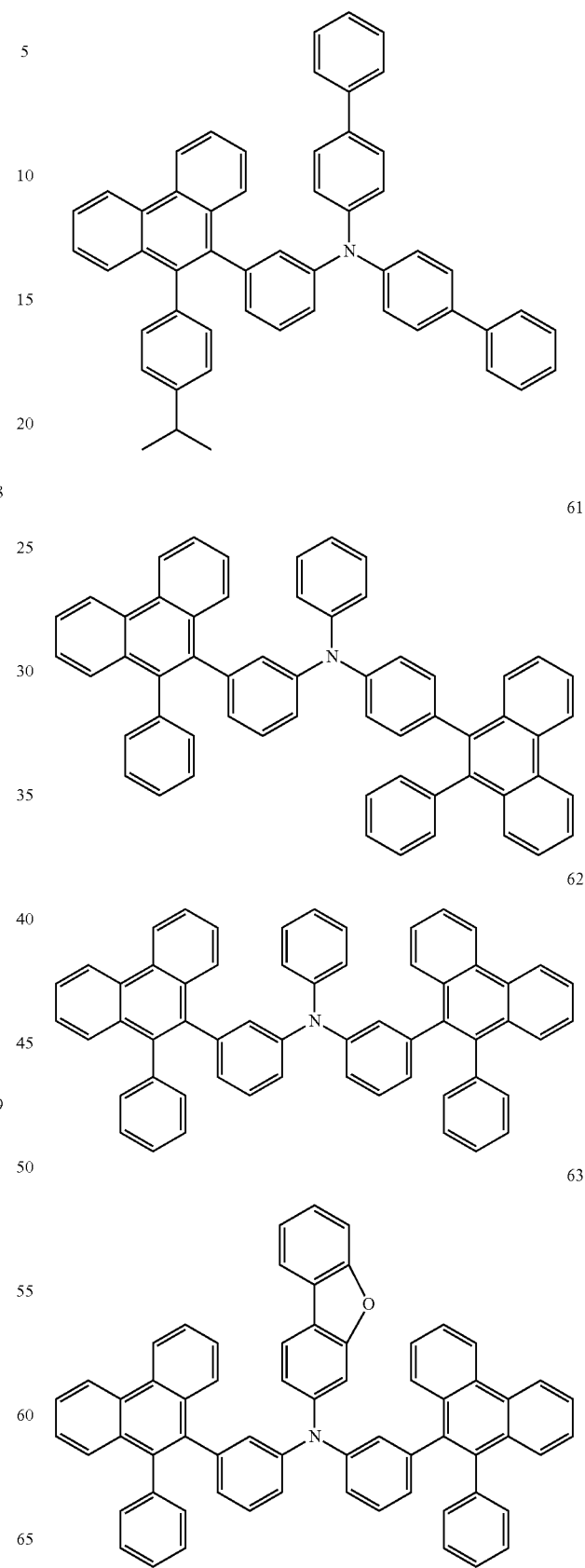

64
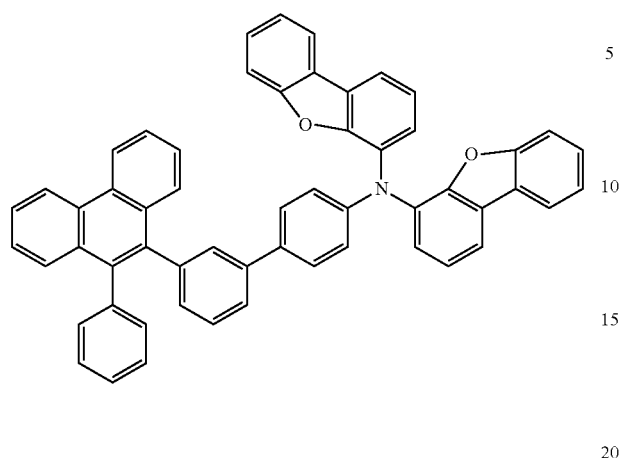
65
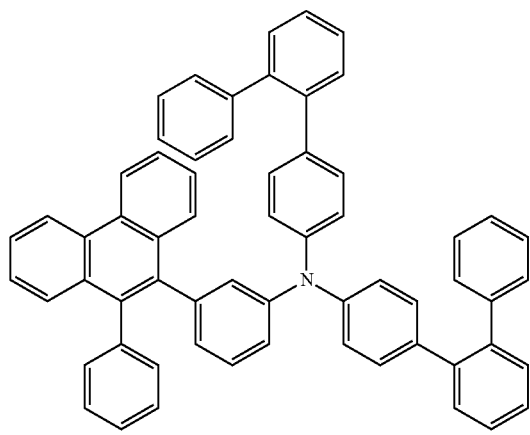
66
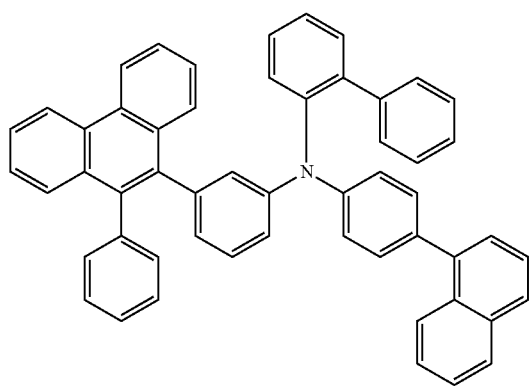
67
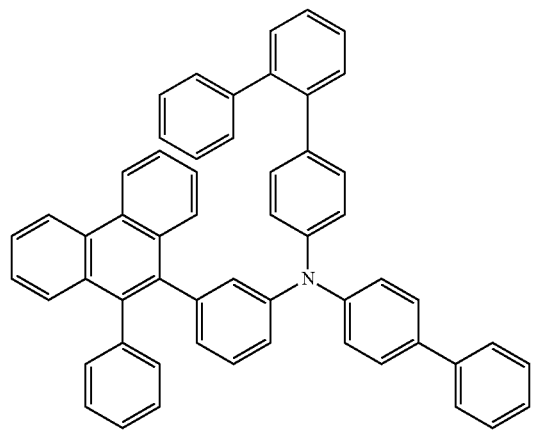
68
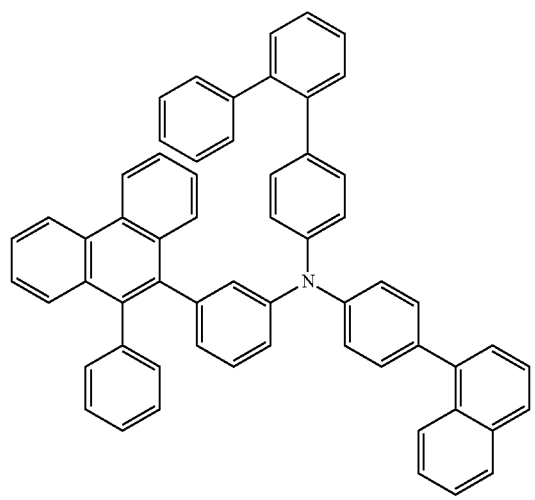
69
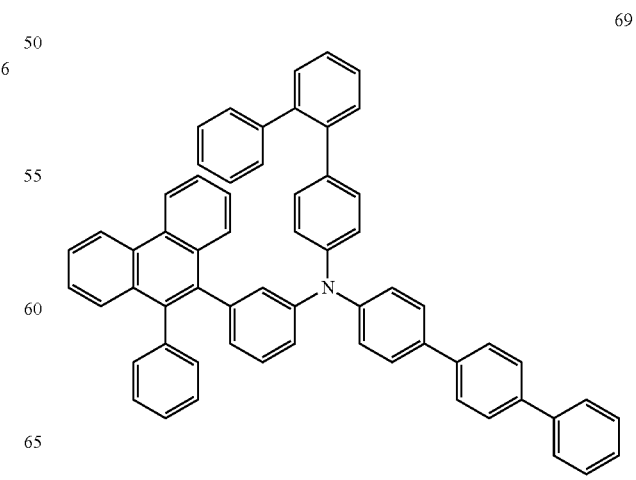

117
-continued
70
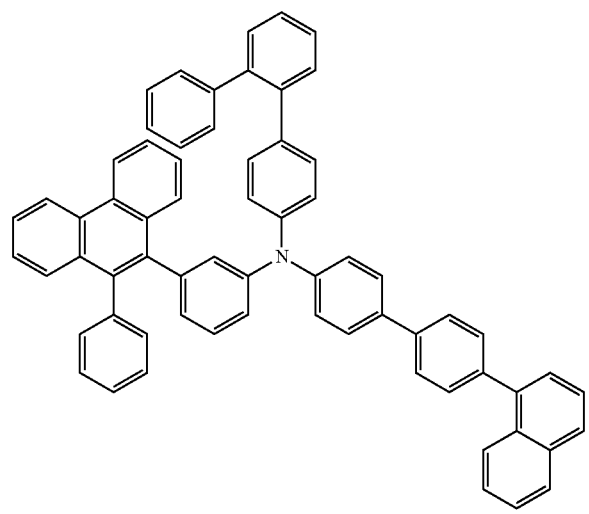
71
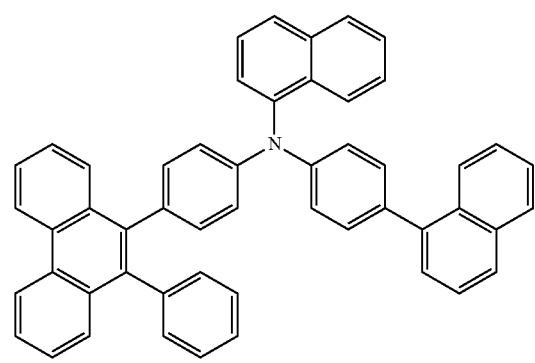
72
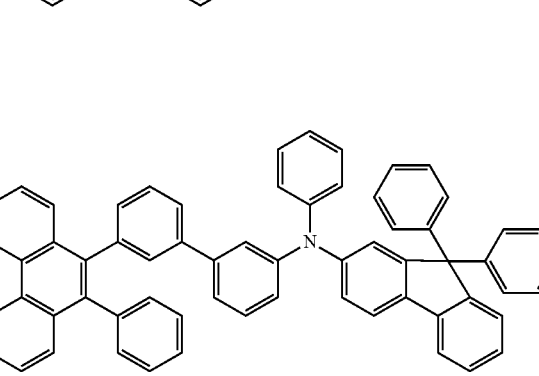
73
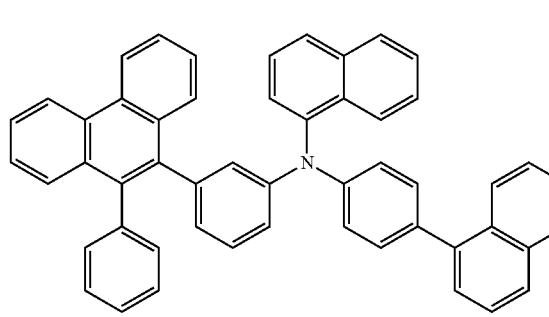
118
-continued
74
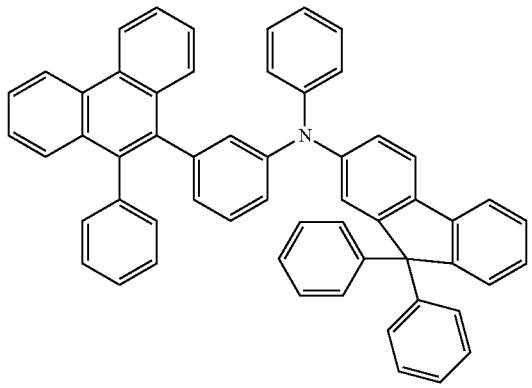
75
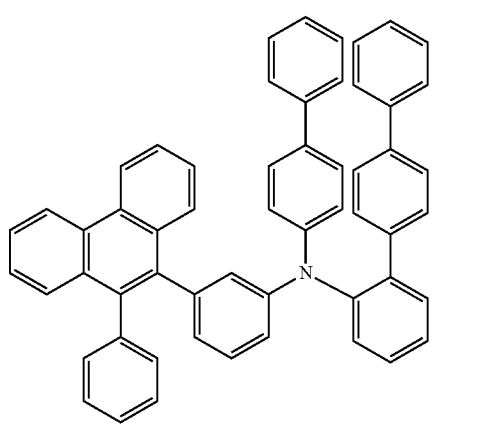
76
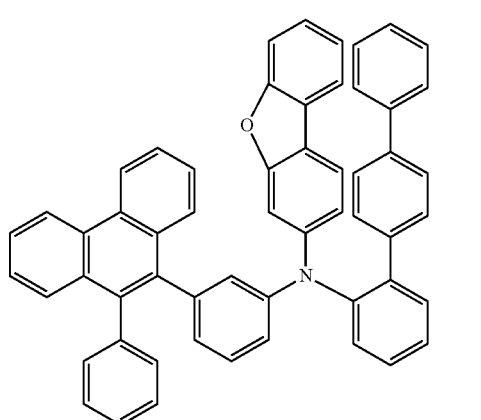
77
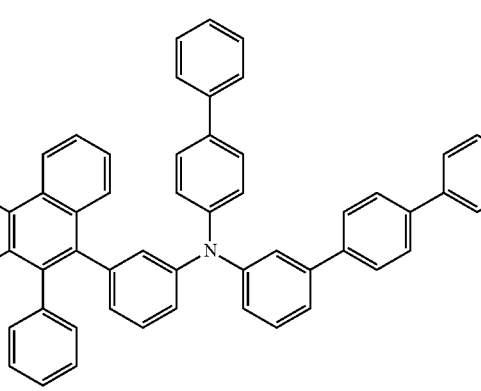

78
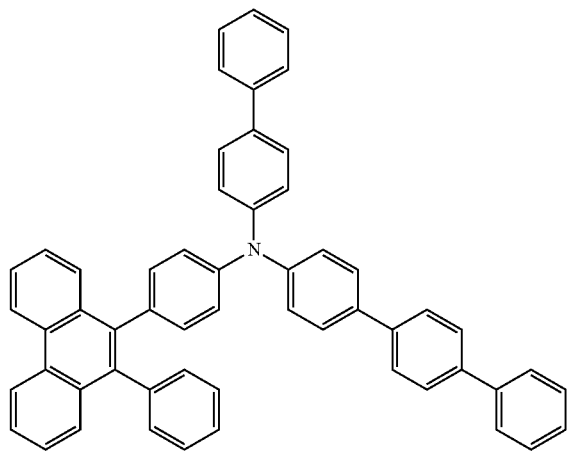
79
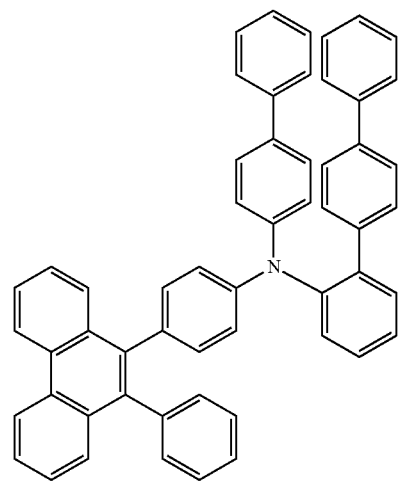
80
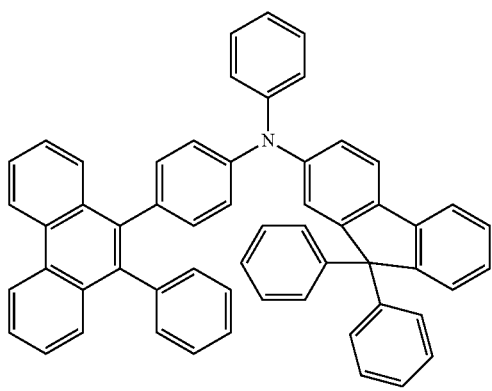
81
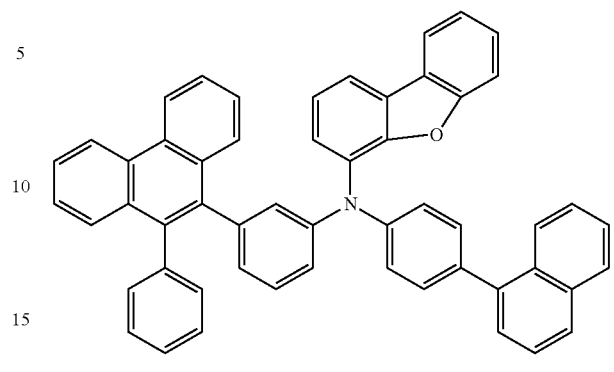
82
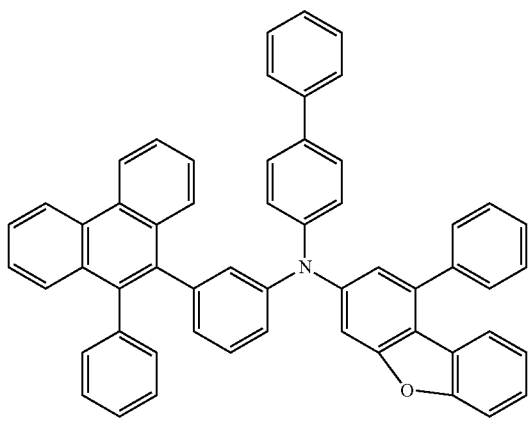
83

84
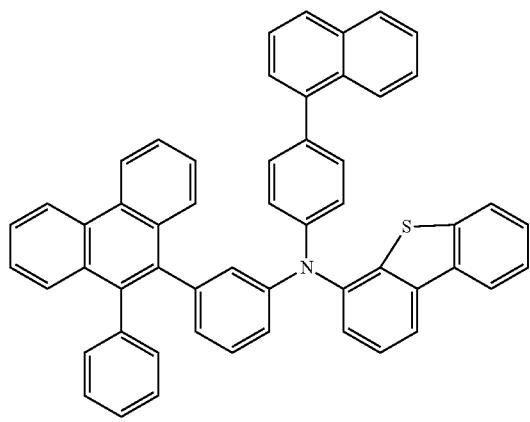
85
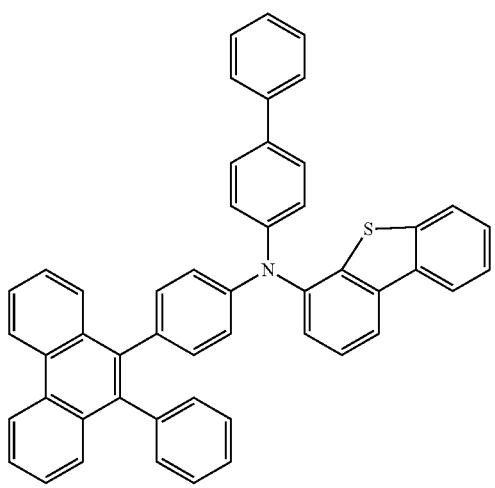
86
88
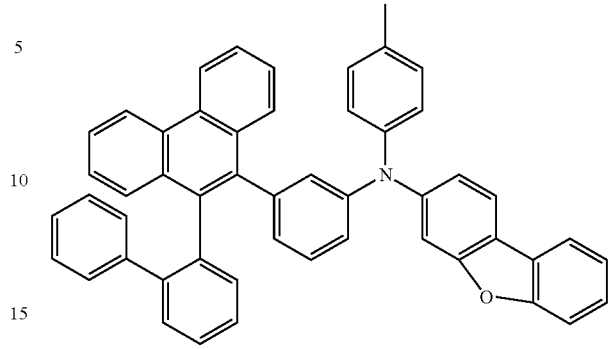
89
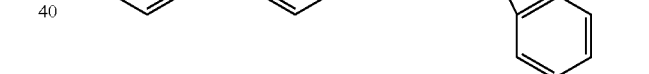
87
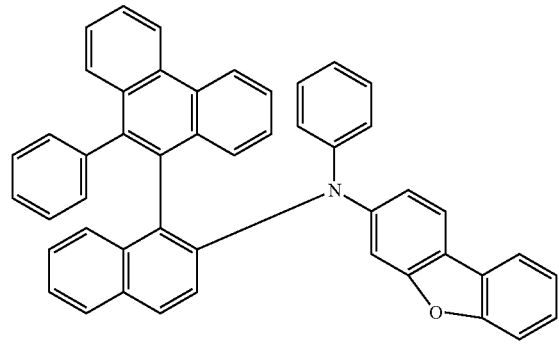
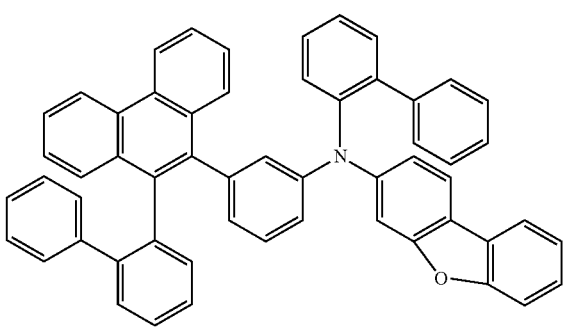
90
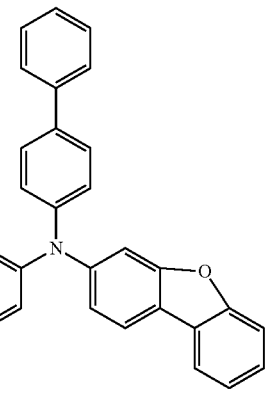

91
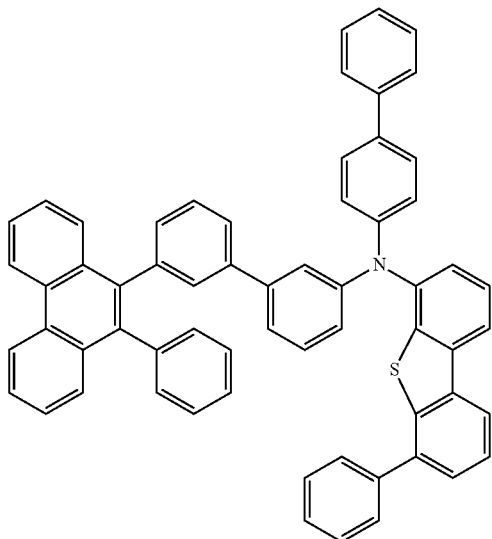
94
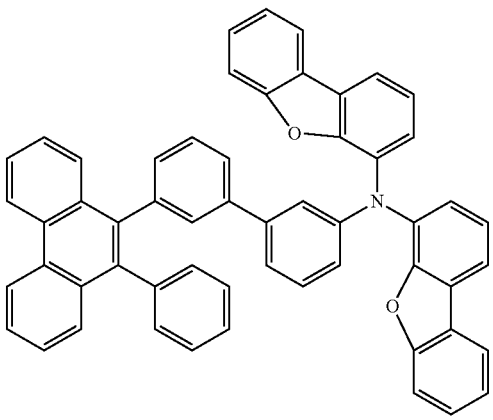
92
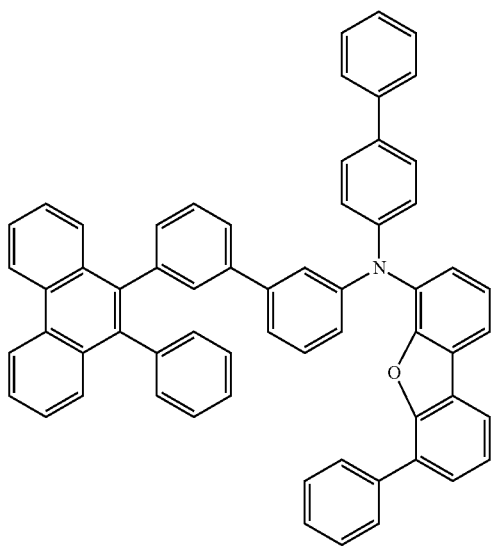
95
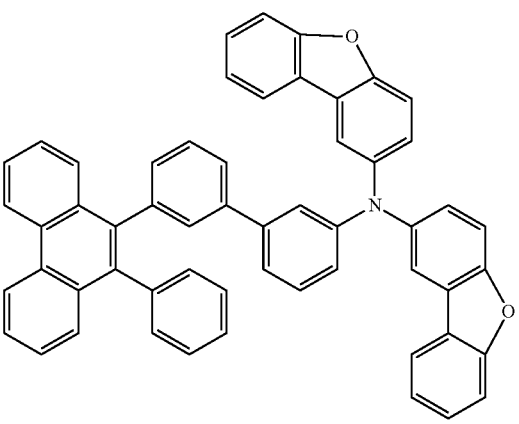
93
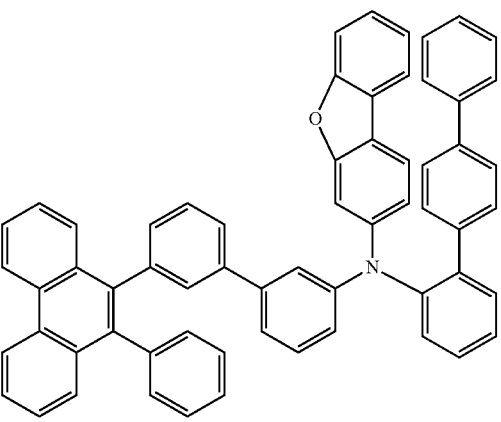
96
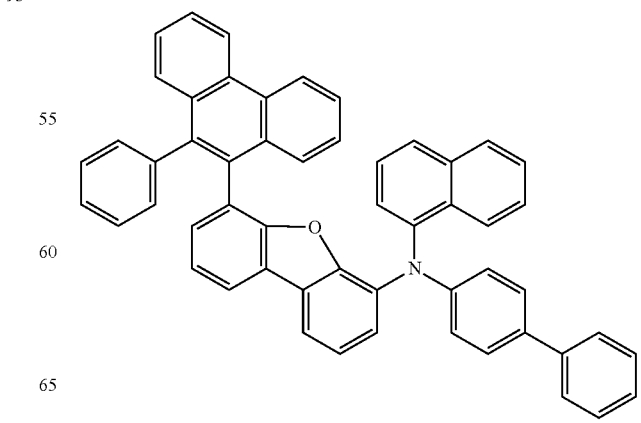

125 126
-continued -continued
97 100
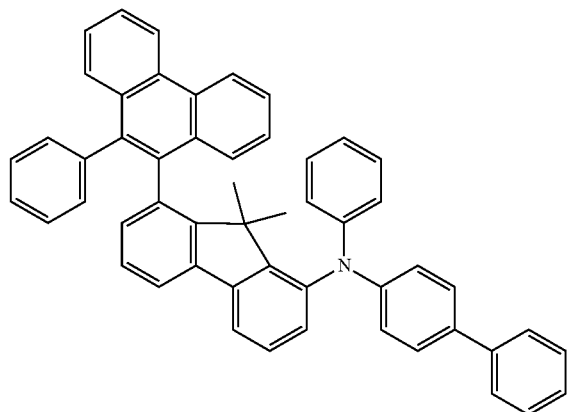 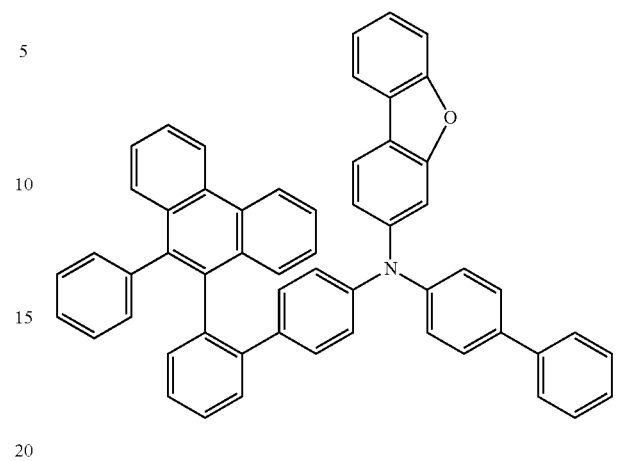
98 101
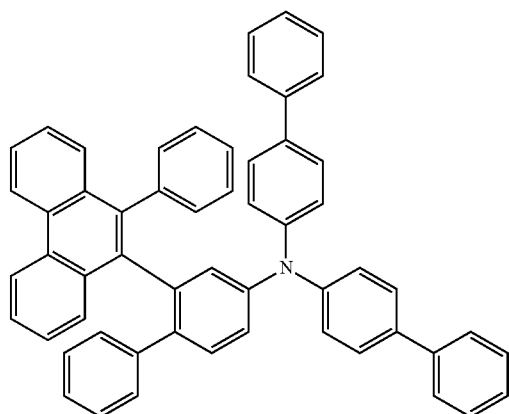
99 102
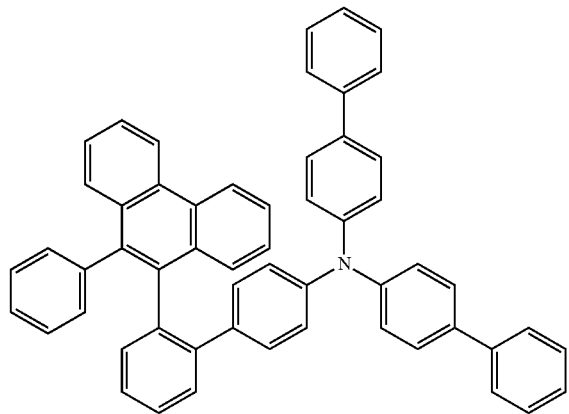

103
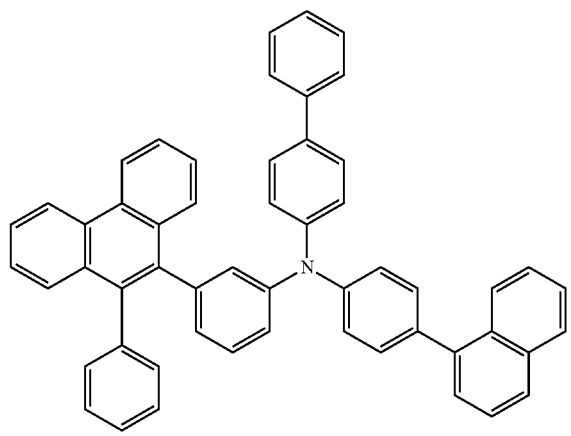
104
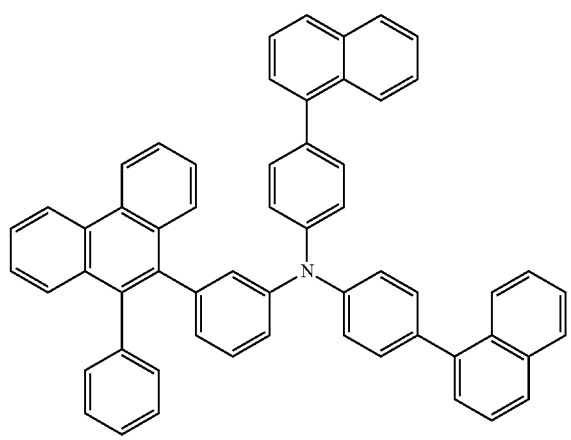
105
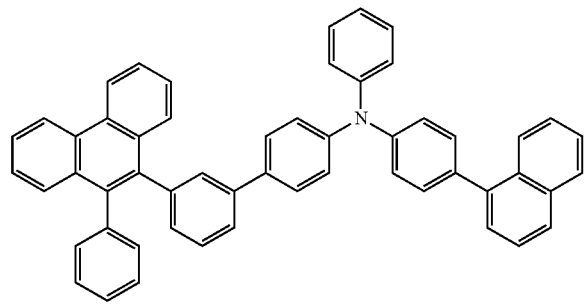
106
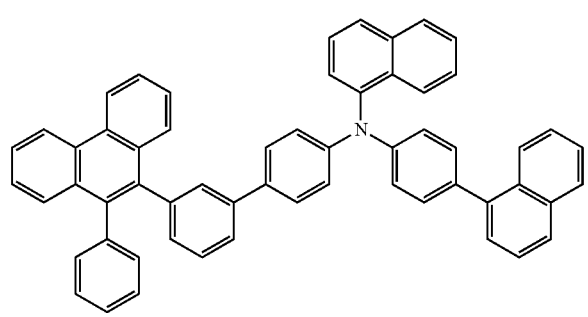
107
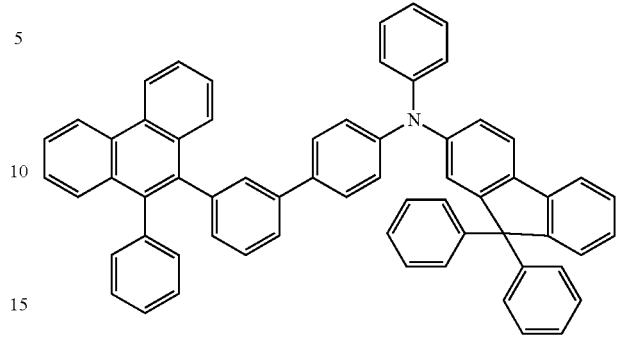
108
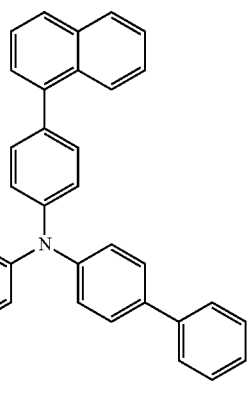
109
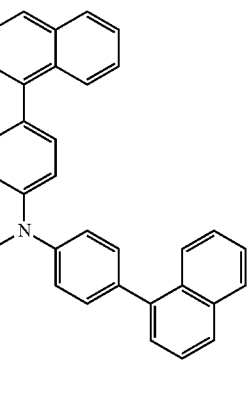

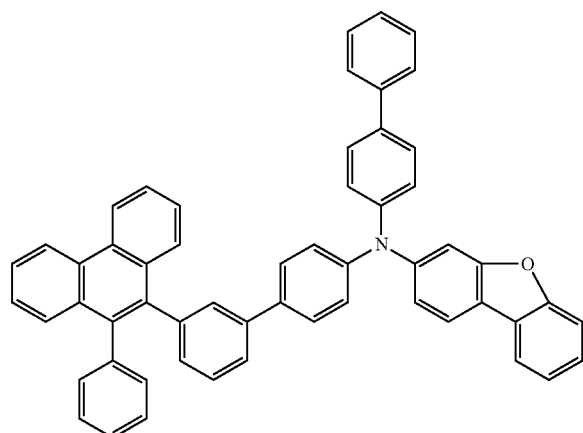
110
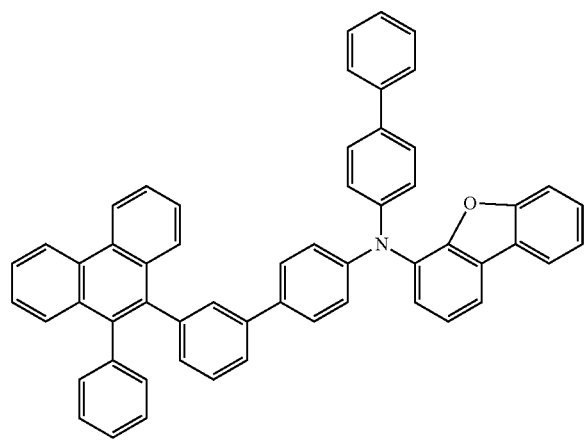
111
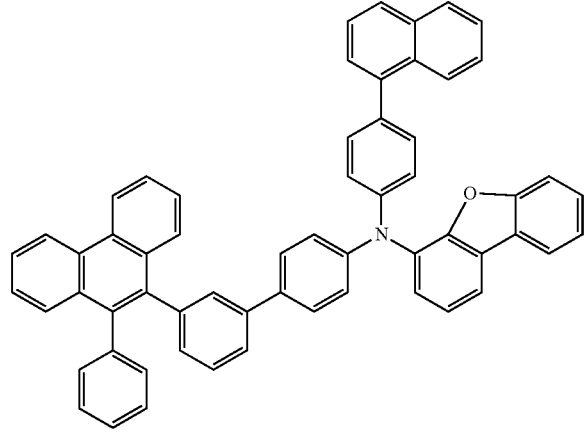
112
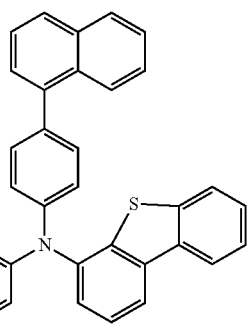
113
114
115
116

117
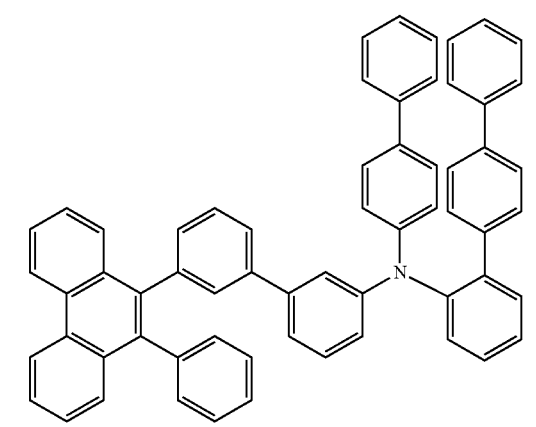
118
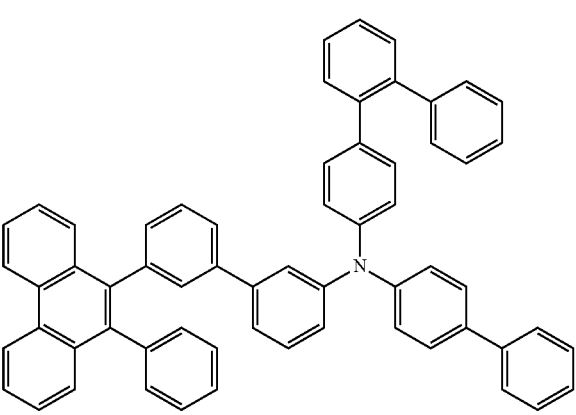
119
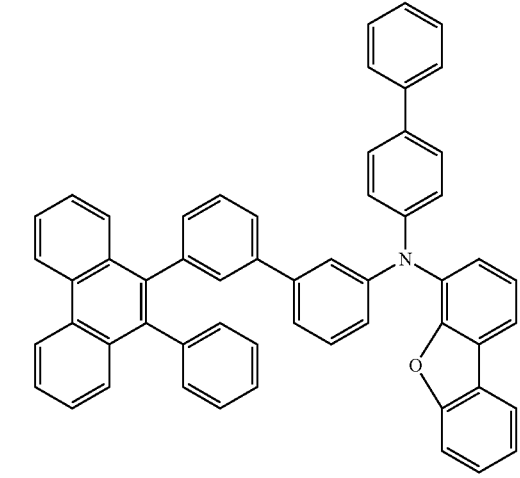
120
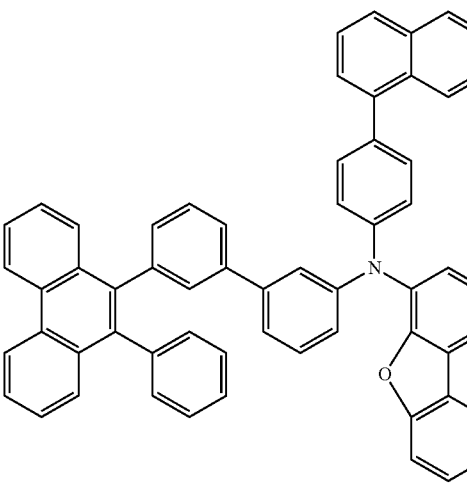
121
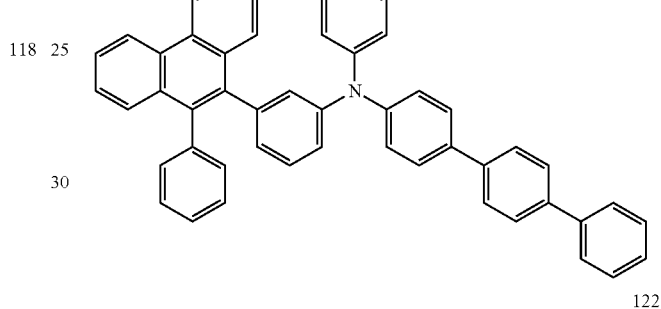
122
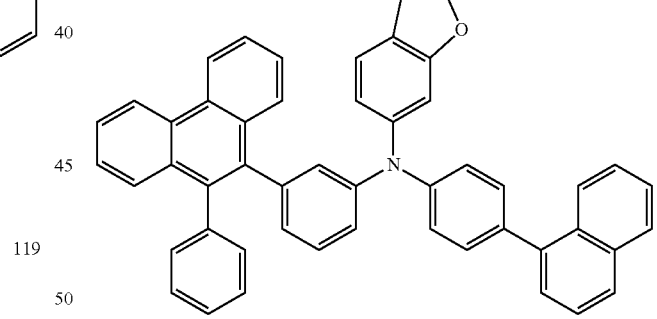
123
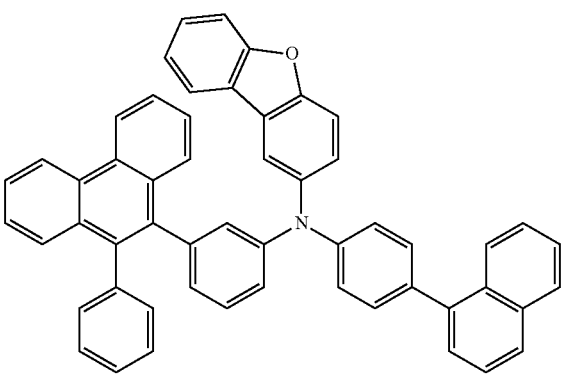

133
-continued
124
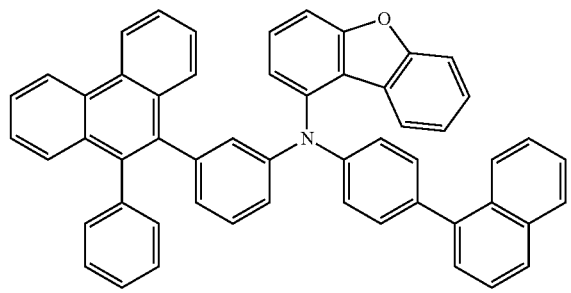
125
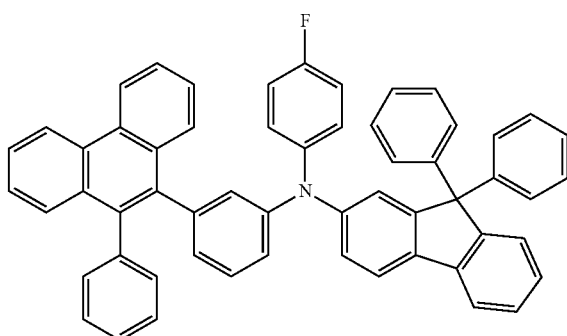
126
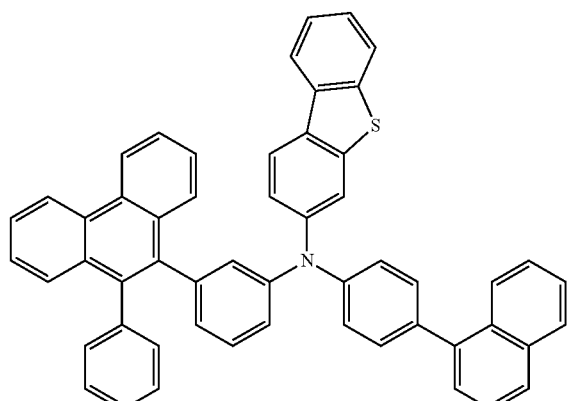
127
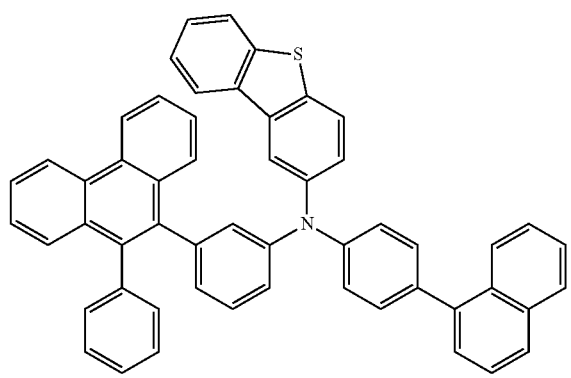
134
-continued
128
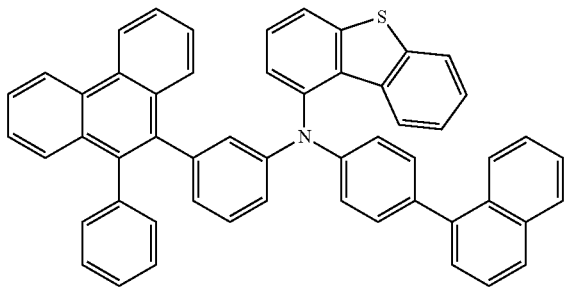
129
130
131

132

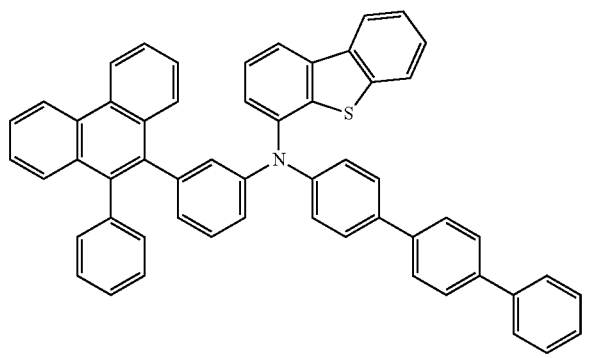

133

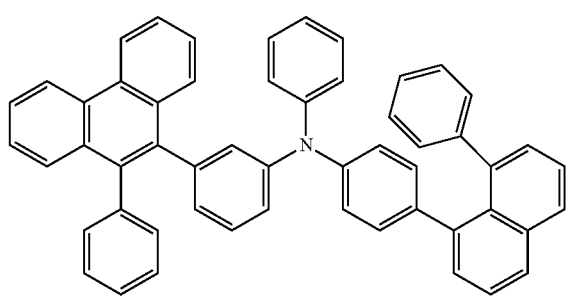

134

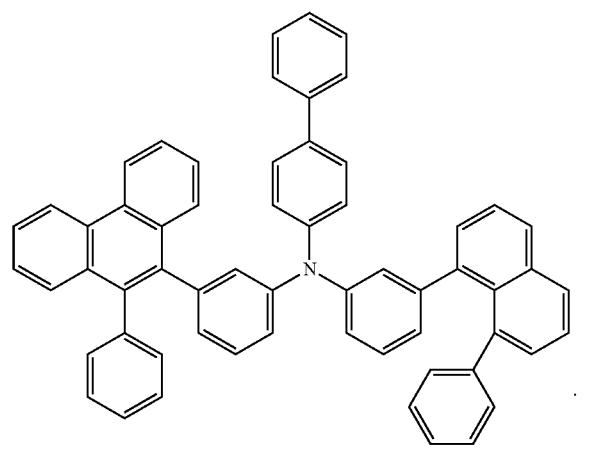

16. An organic electroluminescence device, comprising:
a first electrode;
a hole transport region provided on the first electrode;
an emission layer provided on the hole transport region;
an electron transport region provided on the emission layer; and
a second electrode provided on the electron transport region,
wherein at least one of the hole transport region, the emission region, and the electron transport region includes a monoamine compound represented by the following Formula 1:

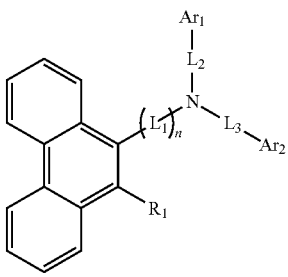

[Formula 1]

where $L_1$ is a substituted or unsubstituted arylene group having 6 to 30 carbon atoms for forming a ring, or a substituted or unsubstituted heteroarylene group having 2 to 30 carbon atoms for forming a ring, n is 1 or 2, $L_2$ and $L_3$ are each independently a direct linkage, a substituted or unsubstituted arylene group having 6 to 30 carbon atoms for forming a ring, or a substituted or unsubstituted heteroarylene group having 2 to 30 carbon atoms for forming a ring, $R_1$ is a substituted or unsubstituted alkyl group having 1 to 10 carbon atoms, a substituted or unsubstituted aryl group having 6 to 30 carbon atoms for forming a ring, a substituted or unsubstituted heteroaryl group having 2 to 30 carbon atoms for forming a ring, or a substituted or unsubstituted aryl silyl group, when R1 is substituted, the substituent is a deuterium atom, a cyano group, a substituted or unsubstituted alkyl group having 1 to 10 carbon atoms, or a substituted or unsubstituted aryl group having 6 to 30 carbon atoms for forming a ring, $Ar_1$ and $Ar_2$ are each independently a substituted or unsubstituted aryl group having 6 to 30 carbon atoms for forming a ring, or a substituted or unsubstituted dibenzofuranyl group, a substituted or unsubstituted dibenzothiophenyl group, a substituted or unsubstituted benzonaphthofuranyl group, or a substituted or unsubstituted benzonaphthothiophenyl group, and wherein when at least one of $L_2$, $L_3$, $Ar_1$ and $Ar_2$ is substituted with a heterocycle, the heterocycle does not include N as a heteroatom.

17. The organic electroluminescence device as claimed in claim 16, wherein the hole transport region includes the monoamine compound represented by Formula 1.

18. The organic electroluminescence device as claimed in claim 17, wherein the hole transport region includes:
a hole injection layer disposed on the first electrode; and
a hole transport layer disposed on the hole injection layer, and
wherein the hole transport layer includes the monoamine compound represented by Formula 1.

19. The organic electroluminescence device as claimed in claim 18, wherein the hole transport layer makes contact with the emission layer.

20. The organic electroluminescence device as claimed in claim 17, wherein the hole transport region includes:
a hole injection layer disposed on the first electrode;
a first hole transport layer disposed on the hole injection layer; and
a second hole transport layer disposed on the first hole transport layer, the second hole transport layer being adjacent to the emission layer, wherein the second hole transport layer includes the monoamine compound represented by Formula 1.

21. The organic electroluminescence device as claimed in claim 16, wherein the monoamine compound represented by Formula 1 is represented by the following Formula 2-1 or 2-2:

[Formula 2-1]

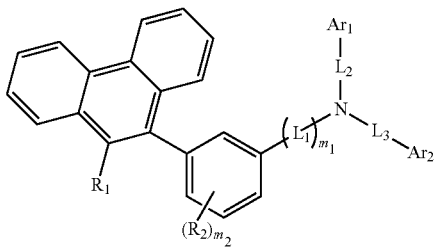

[Formula 2-2]

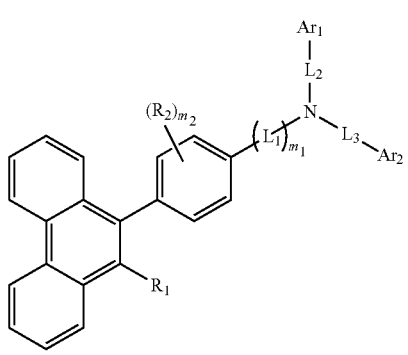

where $m_1$ is 0 or 1, $m_2$ is an integer of 0 to 2, $R_2$ is a hydrogen atom, a deuterium atom, a substituted or unsubstituted alkyl group having 1 to 10 carbon atoms, a substituted or unsubstituted aryl group having 6 to 30 carbon atoms for forming a ring, a substituted or unsubstituted heteroaryl group having 2 to 30 carbon atoms for forming a ring, or a substituted or unsubstituted aryl silyl group, or combines with an adjacent group to form a ring, and $Ar_1$, $Ar_2$, $L_1$, $L_2$, $L_3$, and $R_1$ are the same as defined for Formula 1.

22. The organic electroluminescence device as claimed in claim 21, wherein the monoamine compound represented by Formula 2-1 or 2-2 is represented by one of the following Formulae 2-1-1 to 2-2-3:

[Formula 2-1-1]

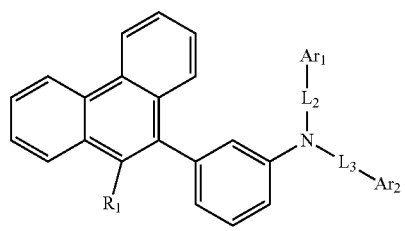

[Formula 2-1-2]

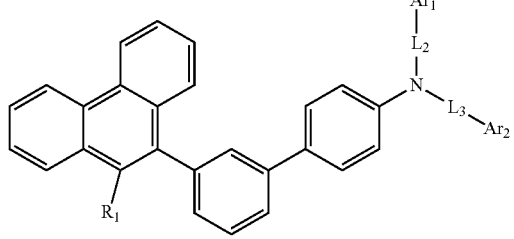

[Formula 2-1-3]

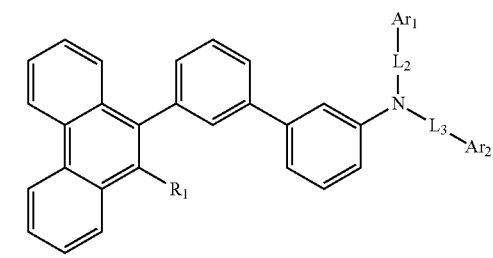

[Formula 2-2-1]

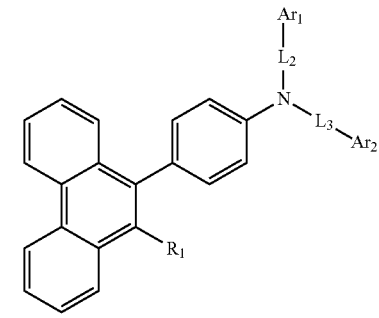

[Formula 2-2-2]

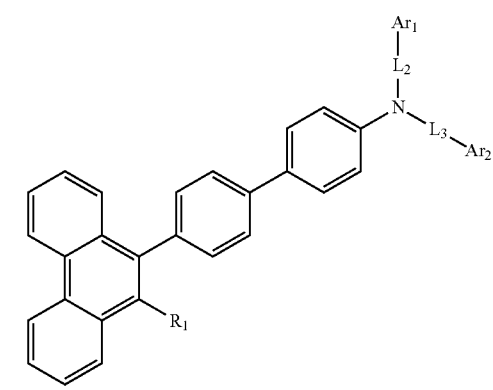

[Formula 2-2-3]

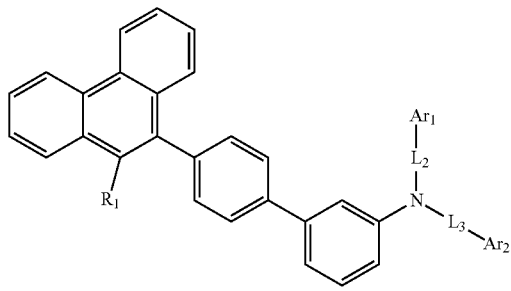

in Formulae 2-1-1 to 2-2-3,

Ar$_1$ and Ar$_2$, L$_2$ and L$_3$, and R$_1$ are the same as defined for Formula 1.

23. The organic electroluminescence device of claim 22, wherein

R$_1$ is a substituted or unsubstituted phenyl group,

L$_3$ is a substituted or unsubstituted phenylene group, and

Ar$_2$ is a substituted or unsubstituted naphthyl group.

24. The organic electroluminescence device of claim 23, wherein

L$_2$ is a substituted or unsubstituted phenylene group, and

Ar$_1$ is a substituted or unsubstituted phenyl group.

25. The organic electroluminescence device of claim 23, wherein

L$_2$ is a direct linkage, and

Ar$_1$ is a substituted or unsubstituted dibenzofuranyl group.

26. The organic electroluminescence device as claimed in claim 16, wherein Ar$_1$ and Ar$_2$ are each independently represented by the following Formula 3:

[Formula 3]

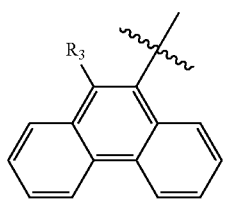

in case Ar$_1$ and Ar$_2$ are each independently represented by Formula 3, in Formula 1, where L$_2$ and L$_3$ are each independently a substituted or unsubstituted arylene group having 6 to 30 carbon atoms for forming a ring, or a substituted or unsubstituted heteroarylene group having 2 to 30 carbon atoms for forming a ring, in Formula 3, R$_3$ is a substituted or unsubstituted alkyl group having 1 to 10 carbon atoms, a substituted or unsubstituted aryl group having 6 to 30 carbon atoms for forming a ring, a substituted or unsubstituted heteroaryl group having 2 to 30 carbon atoms for forming a ring, or a substituted or unsubstituted aryl silyl group.

27. The organic electroluminescence device of claim 16, wherein Ar$_1$ and Ar$_2$ are each independently represented by the following Formula 4:

[Formula 4]

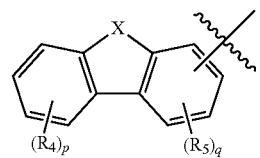

in Formula 4,

X is O or S,

R$_4$ and R$_5$ are each independently a hydrogen atom, a deuterium atom, a substituted or unsubstituted alkyl group having 1 to 10 carbon atoms, a substituted or unsubstituted aryl group having 6 to 30 carbon atoms for forming a ring, a substituted or unsubstituted heteroaryl group having 2 to 30 carbon atoms for forming a ring, or a substituted or unsubstituted aryl silyl group, p is an integer of 0 to 4, and q is an integer of 0 to 3.

28. The organic electroluminescence device as claimed in claim 16, wherein the monoamine compound represented by Formula 1 is at least one of compounds in the following Compound Group 1:

[Compound Group 1]

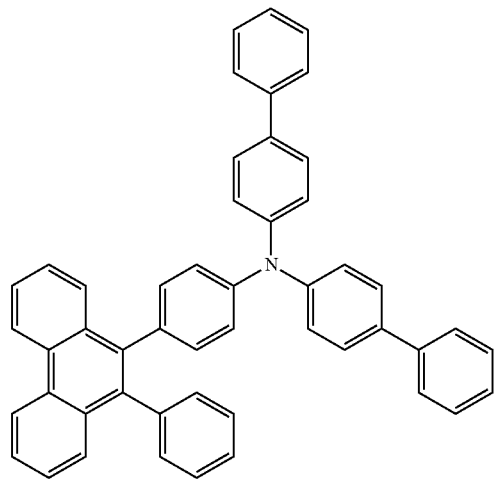

1

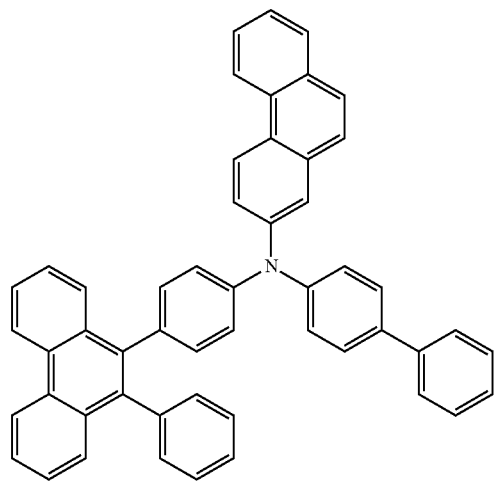

2

3
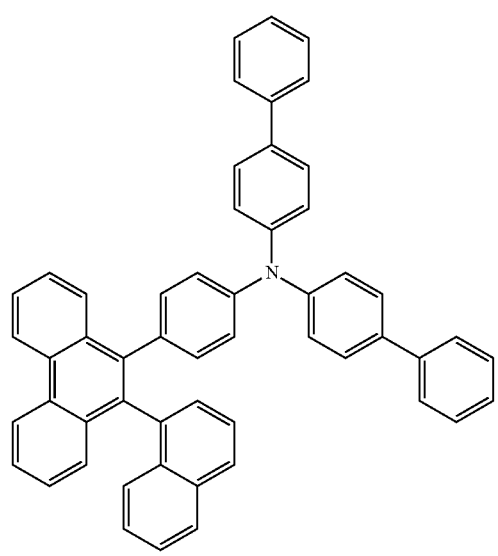
4
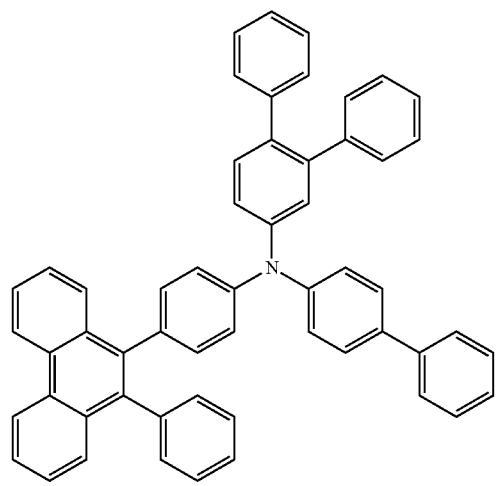
5
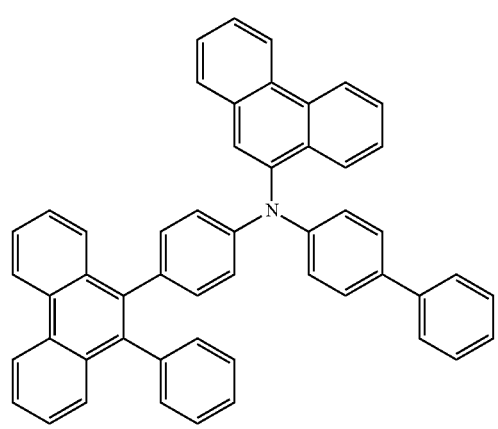
6
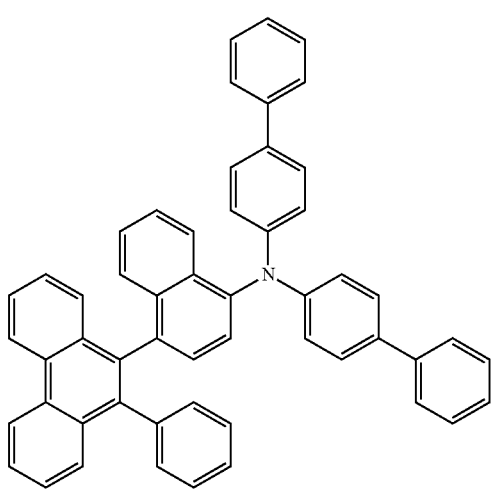
7
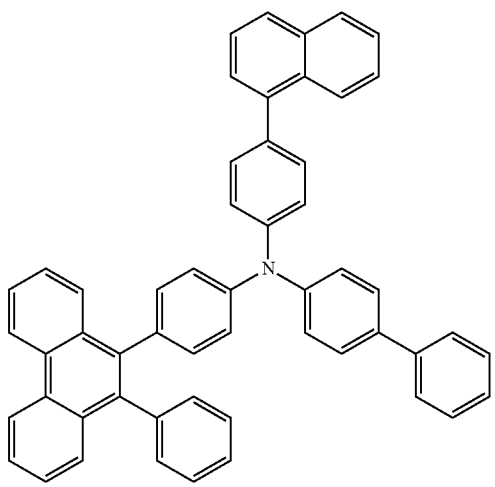
8
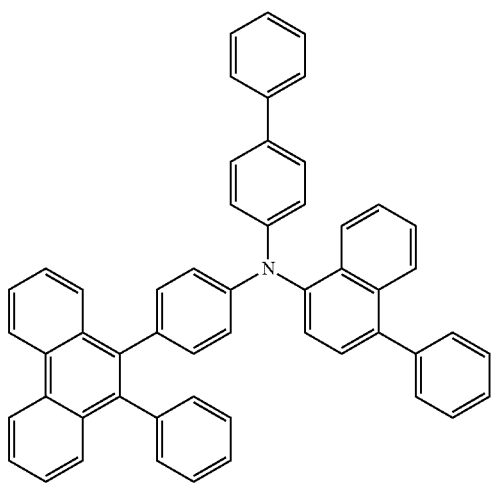

9
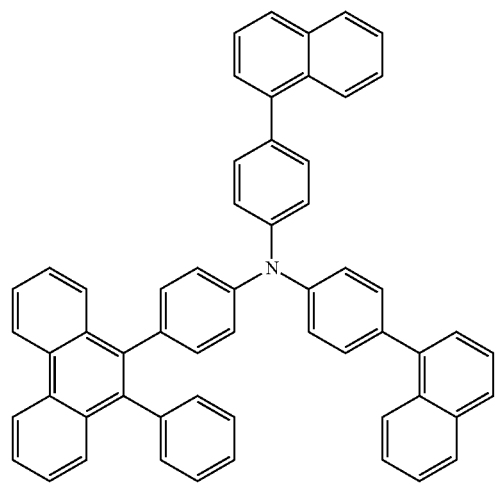
10
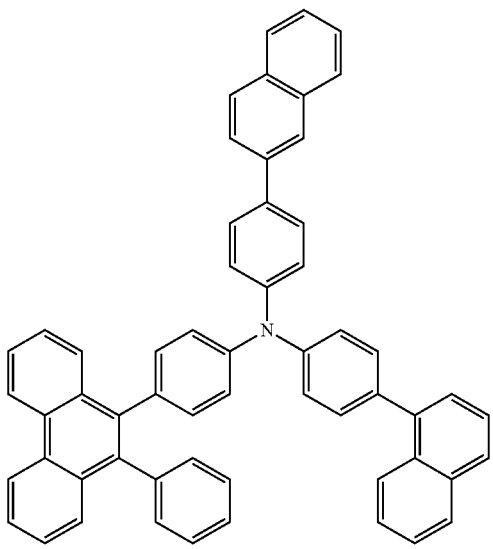
11
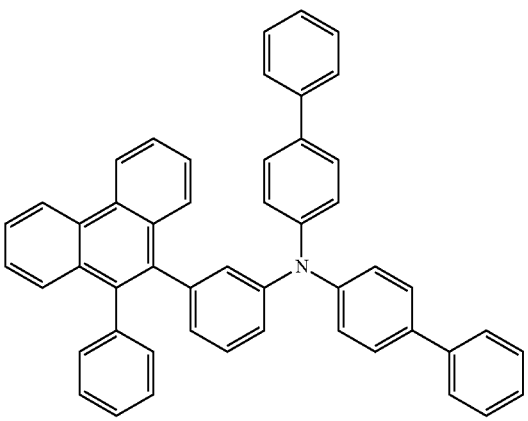
12
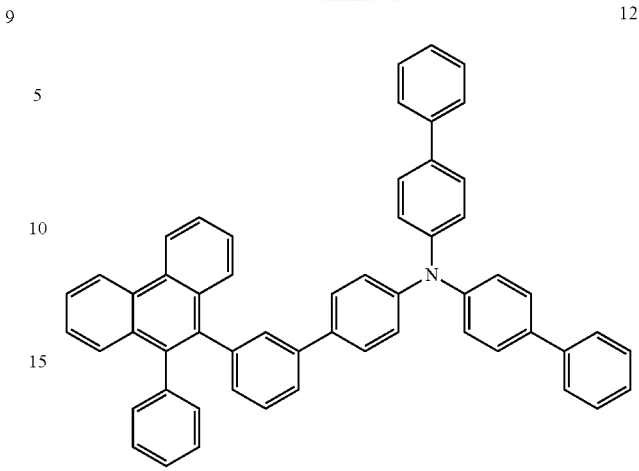
13
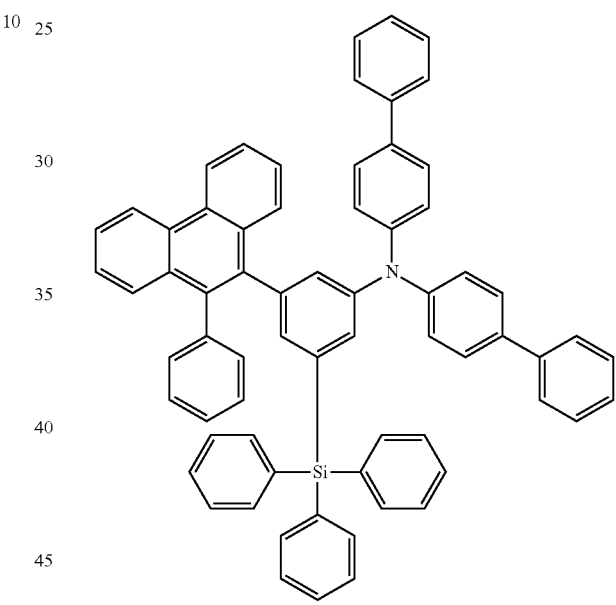
14
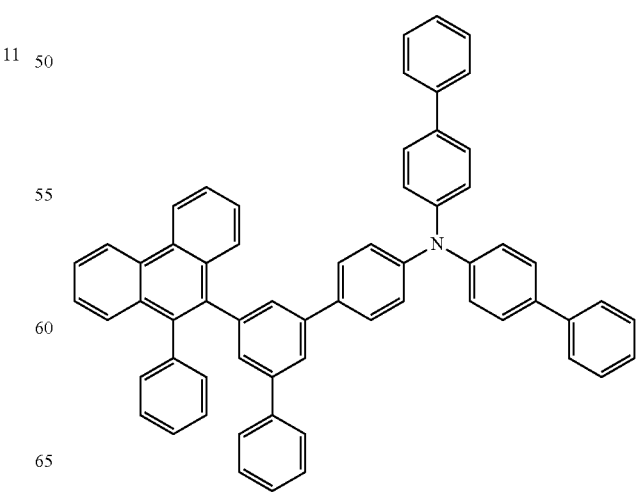

15
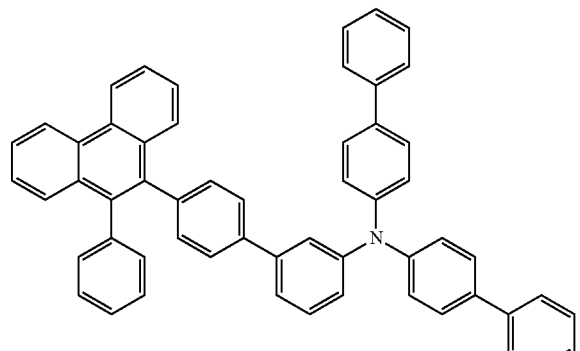
16
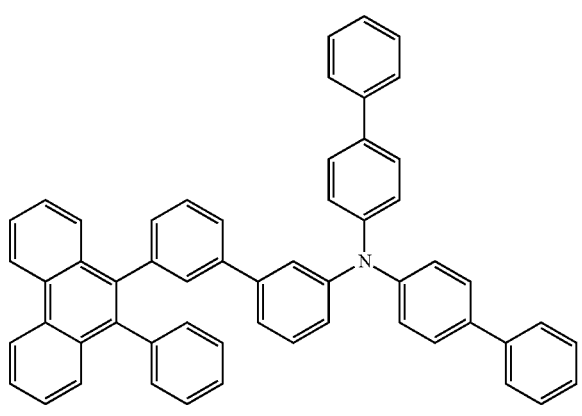
17
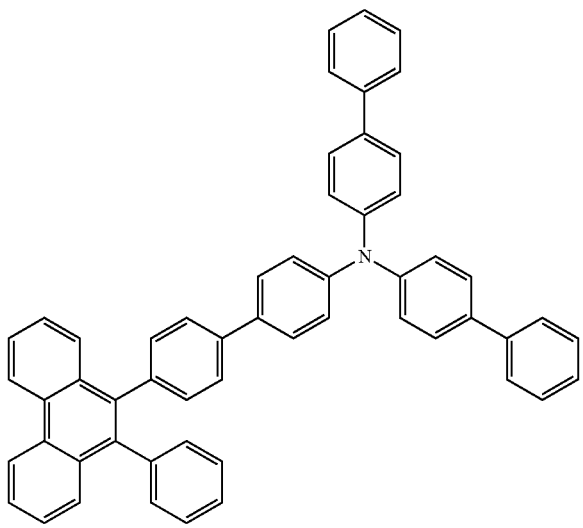
18
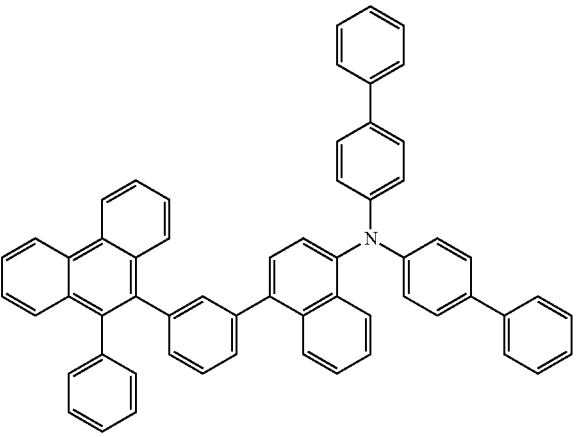
19
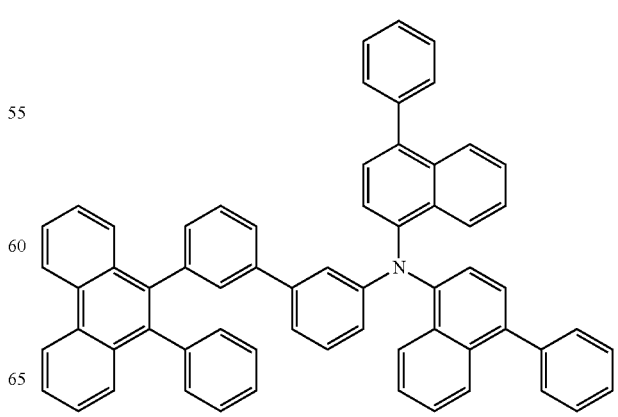
20

21
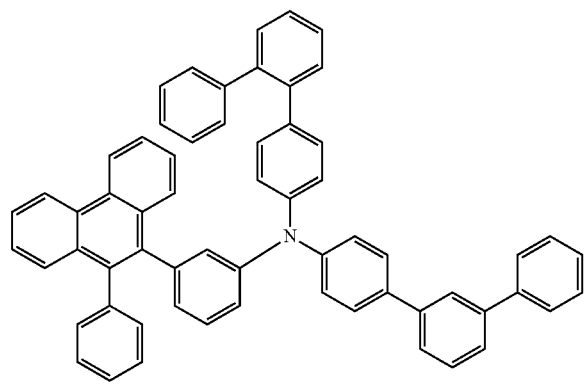
22
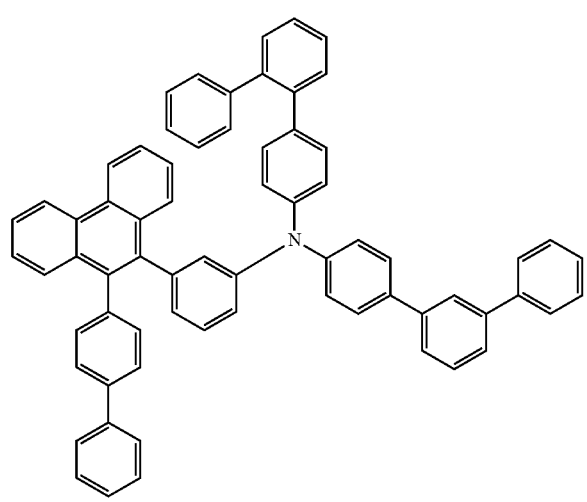
23
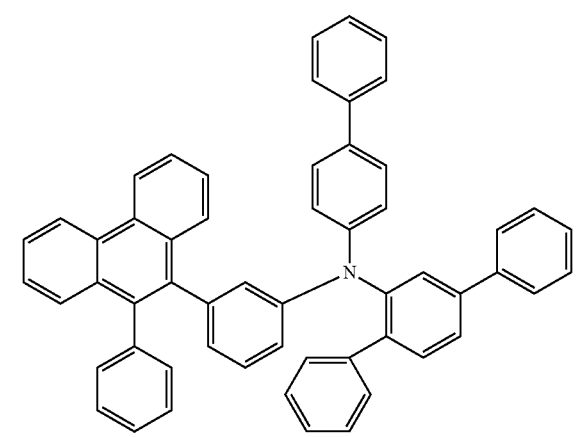
24
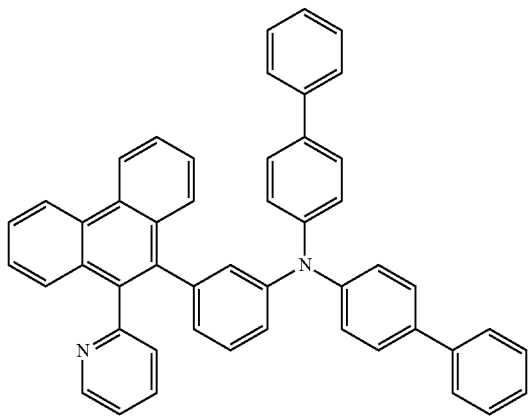
25
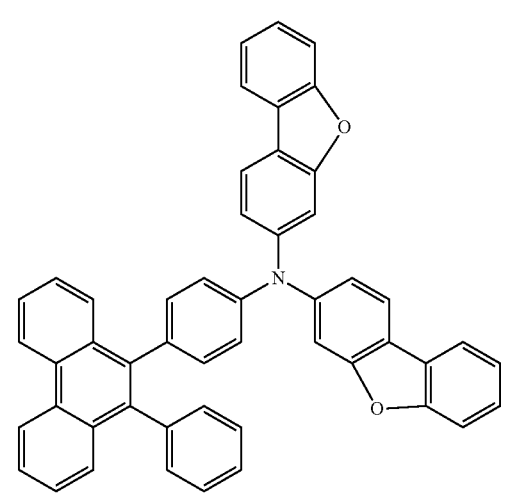
26
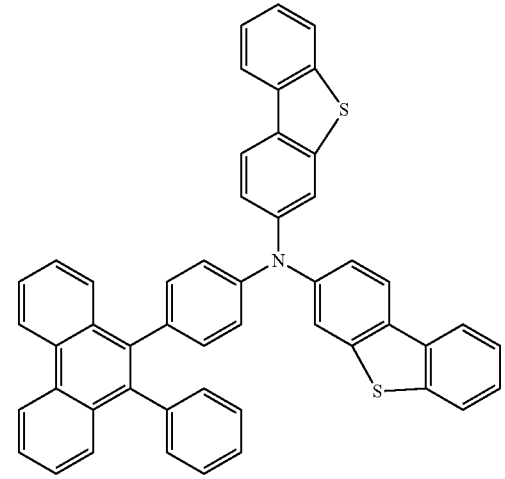

27
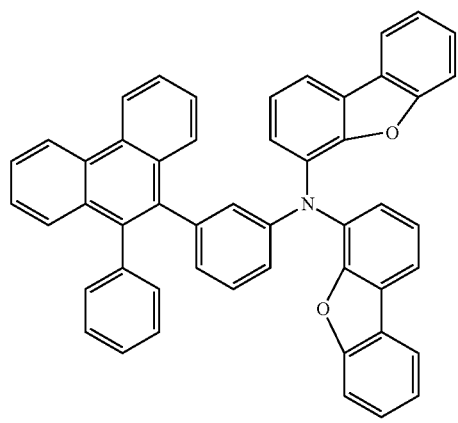
28
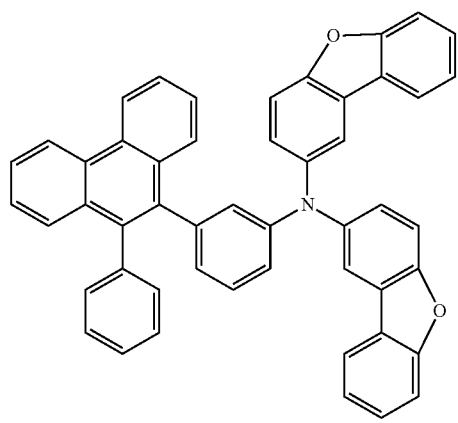
29
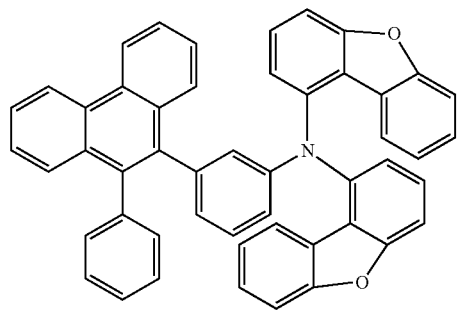
30
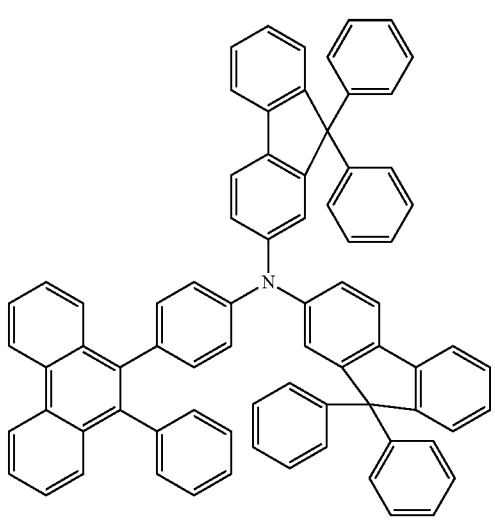
31
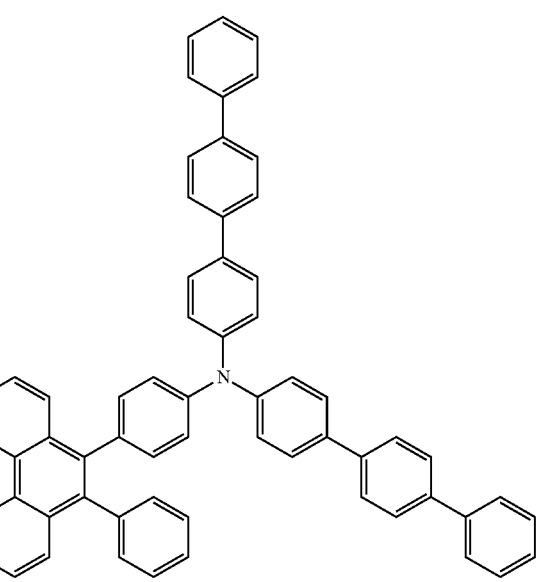
32
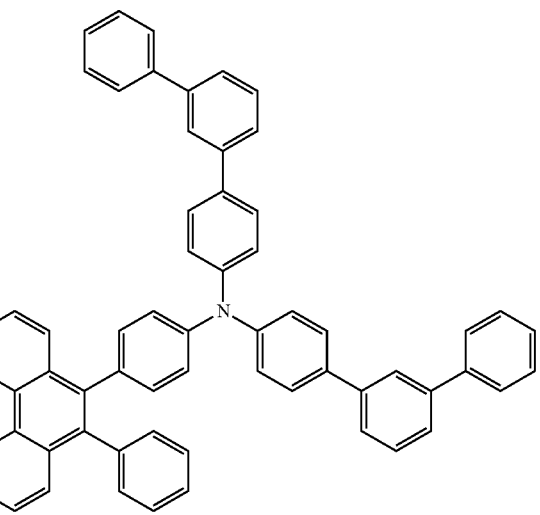

33
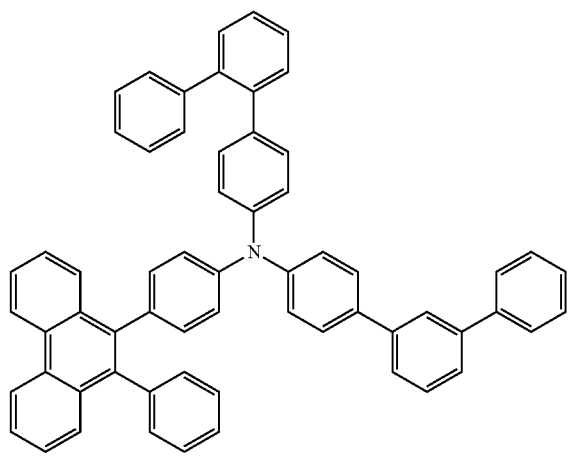
34
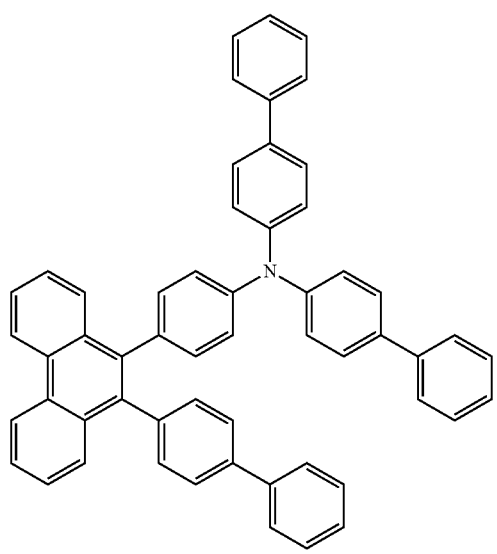
35
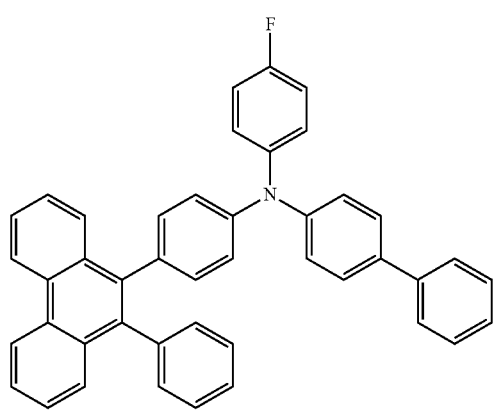
36
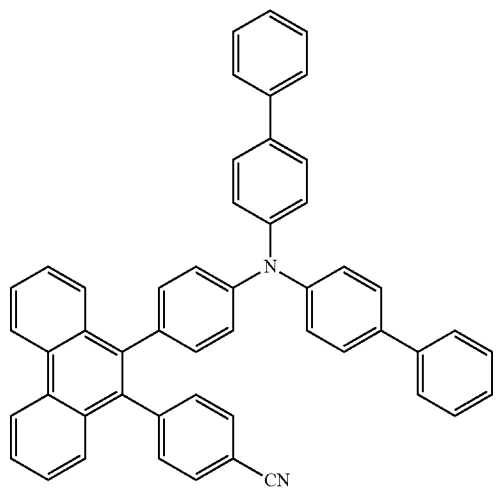
37
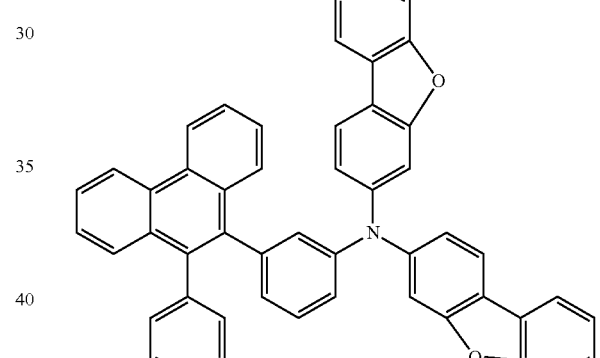
38
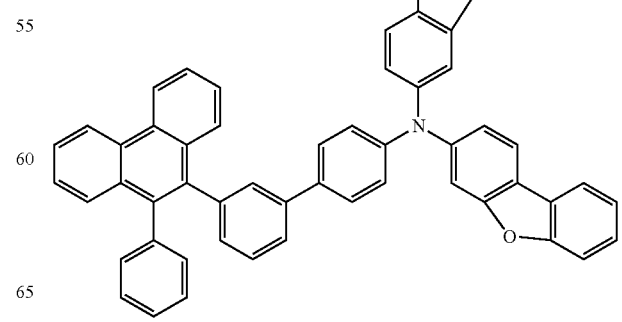

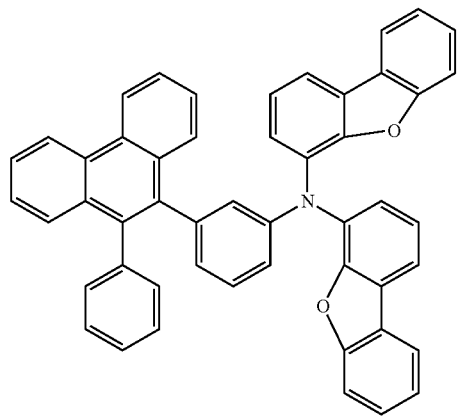
39
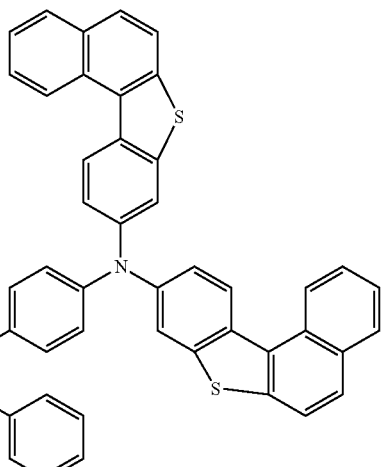
42
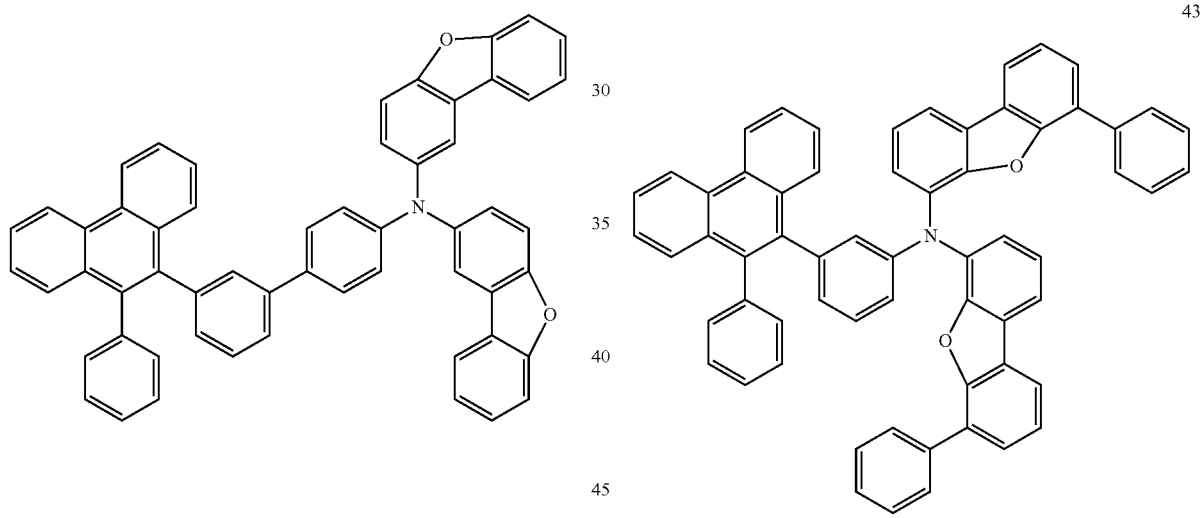
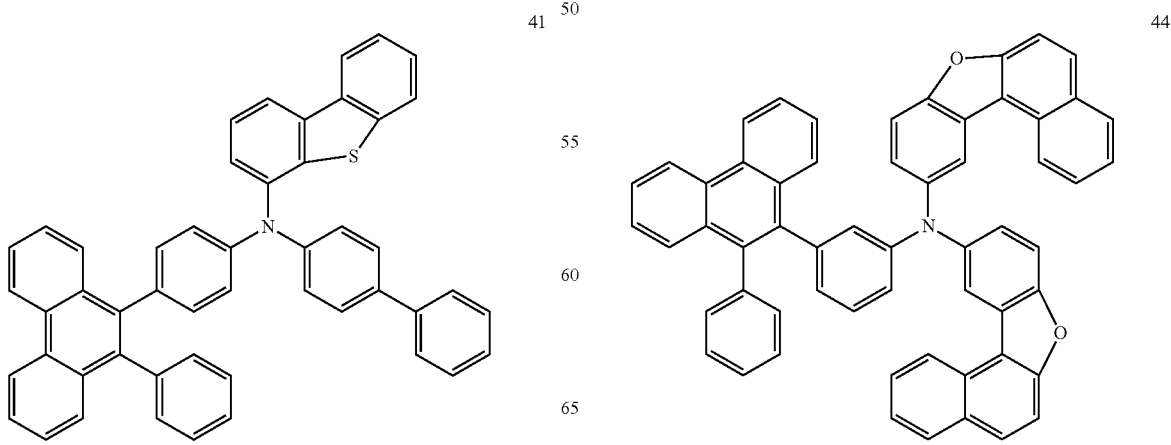

45
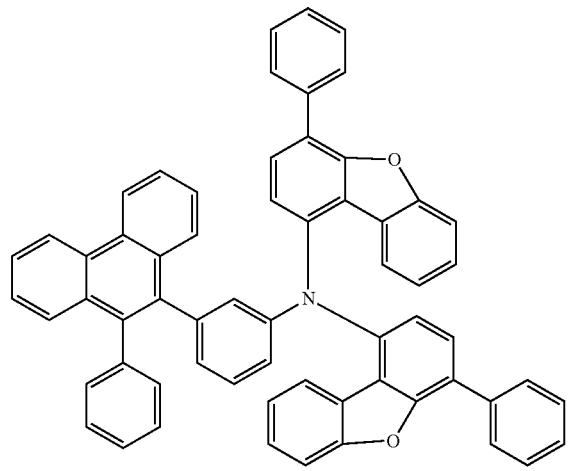
46
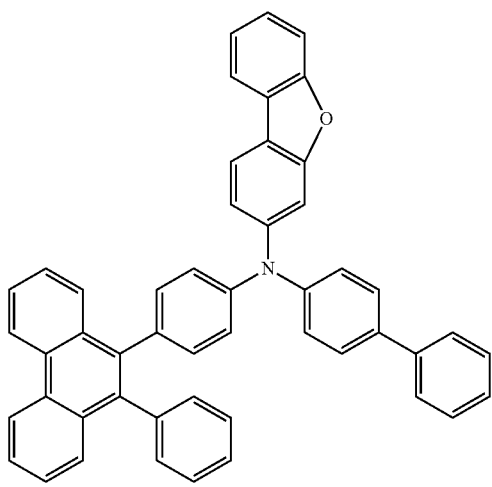
47
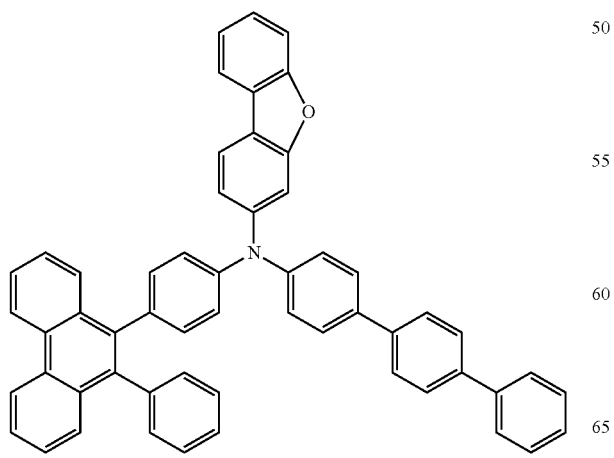
48
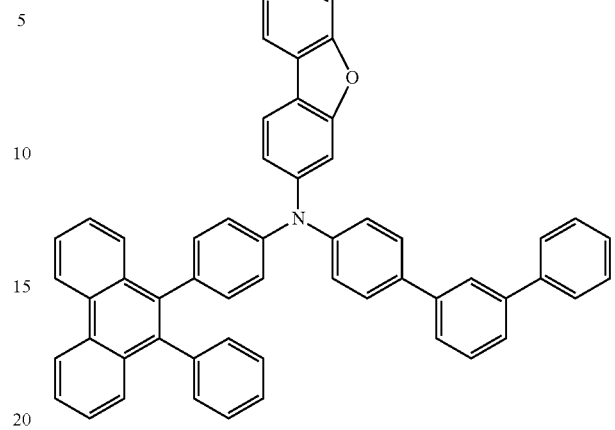
49
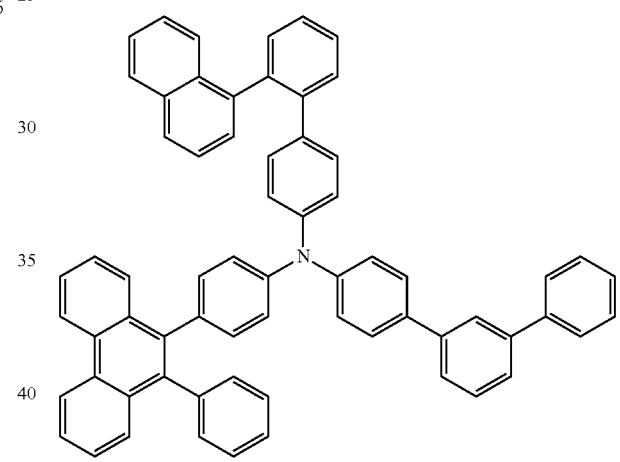
50
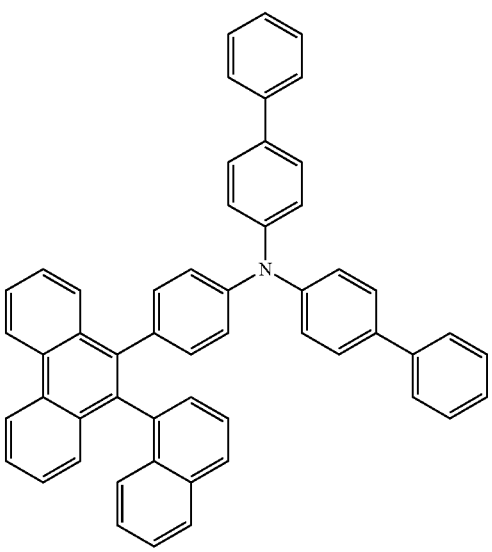

51
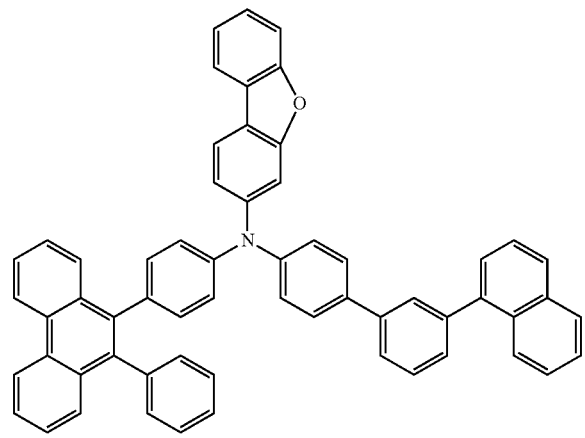
52
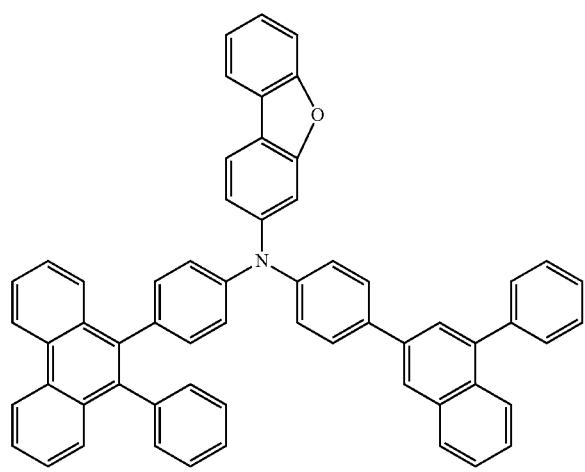
53
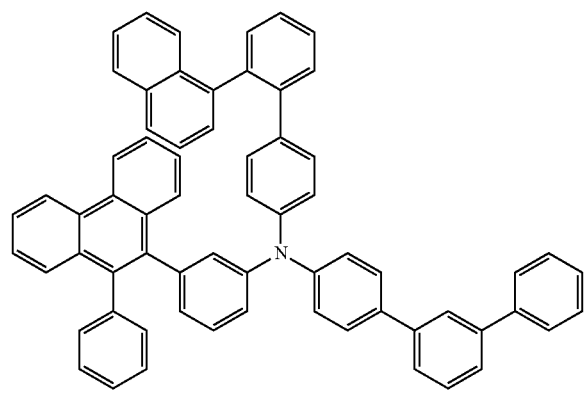
54
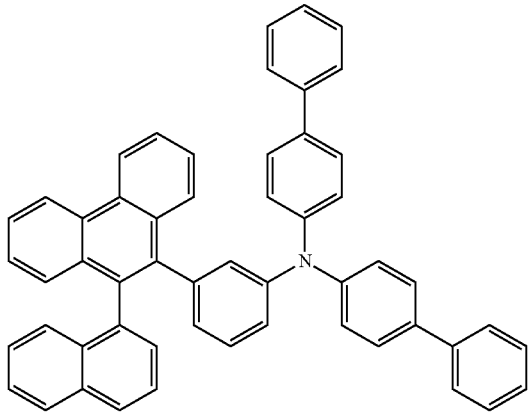
55
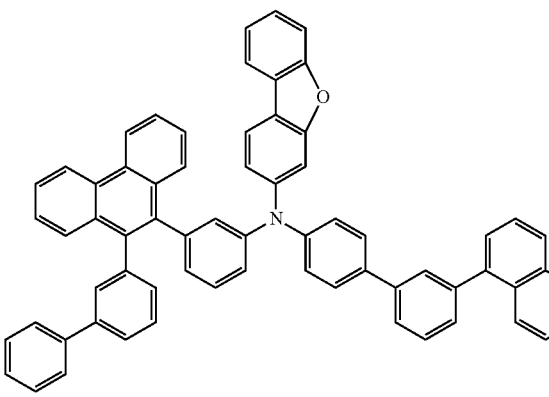
56
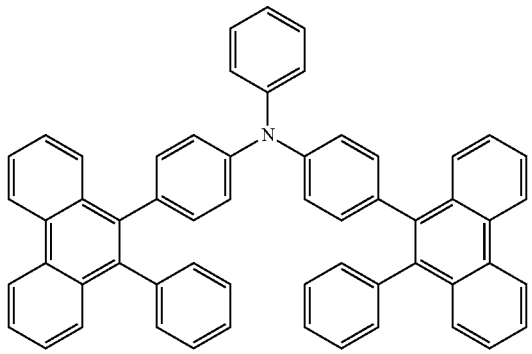

57
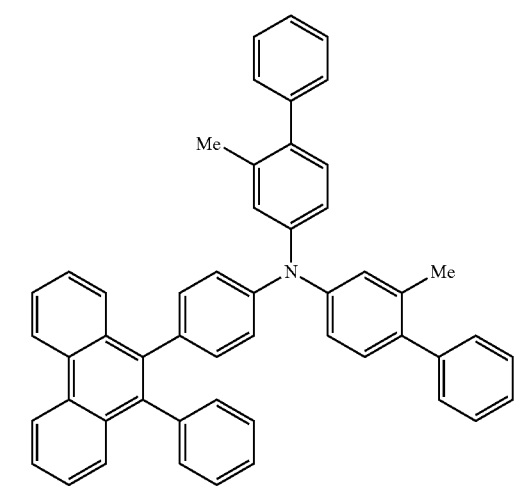
58
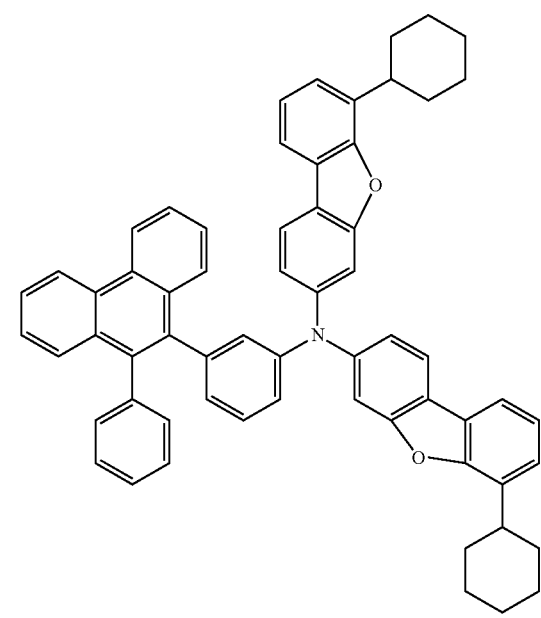
59
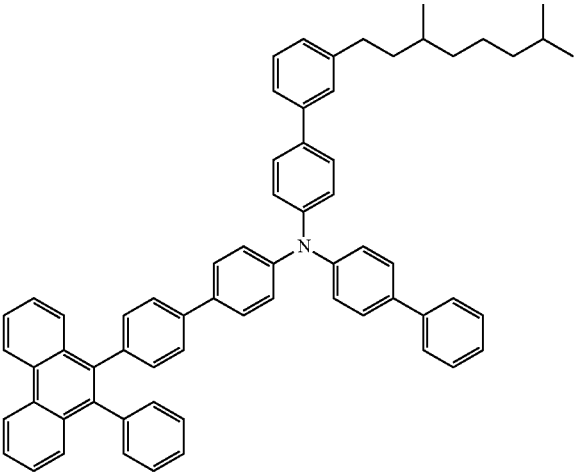
60
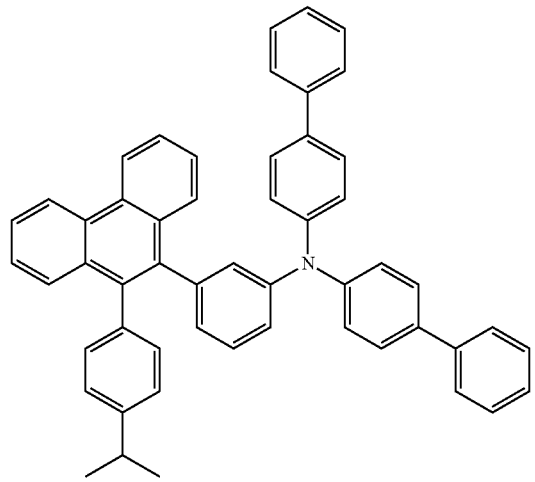
61
62
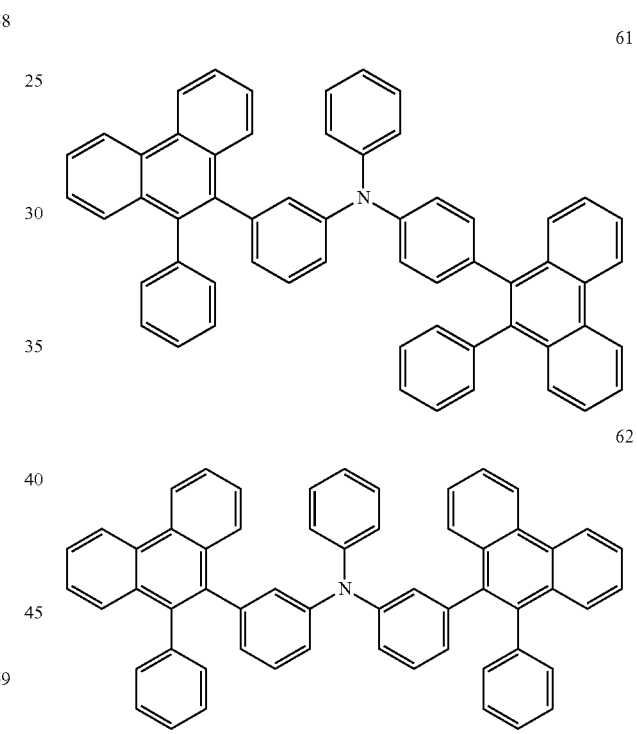
63
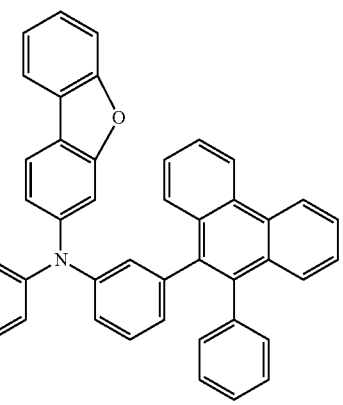

64
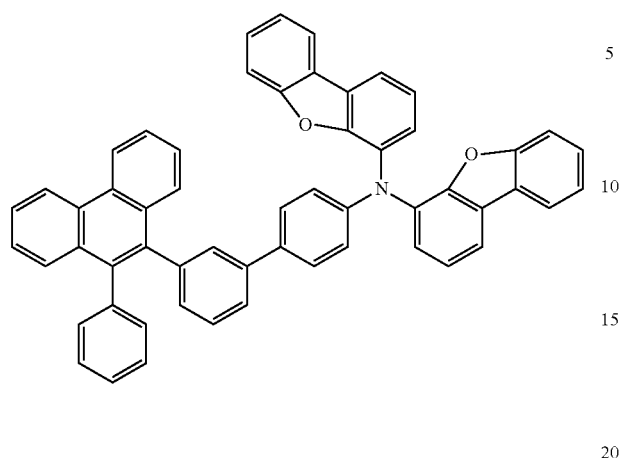
65
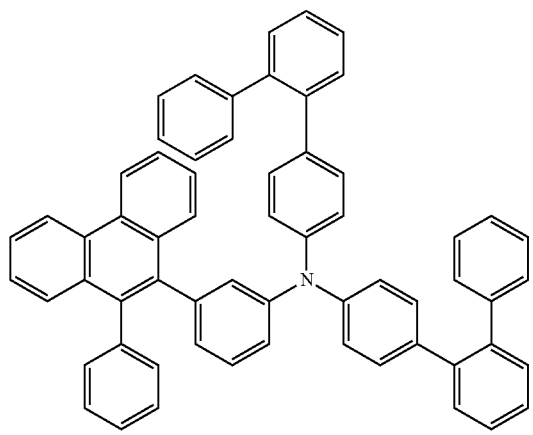
66
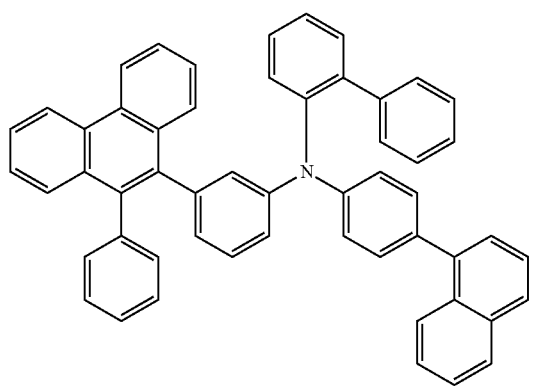
67
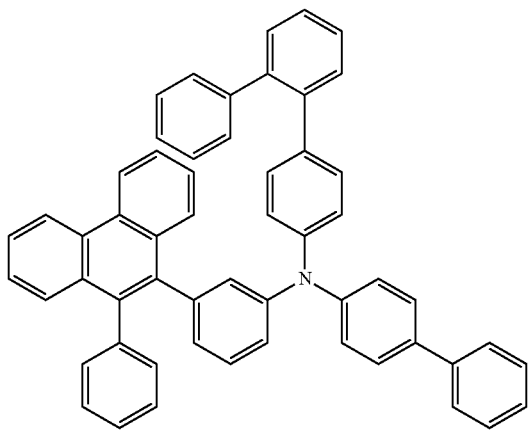
68
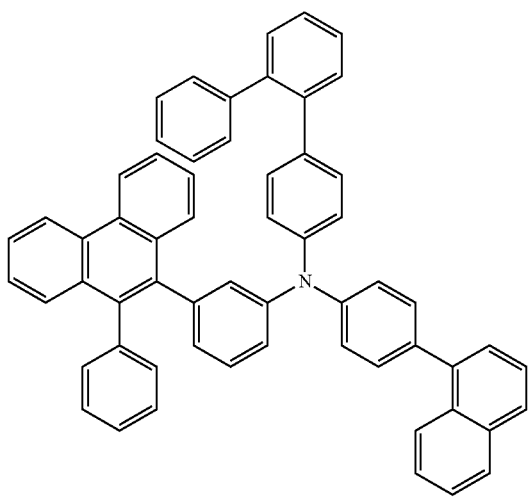
69
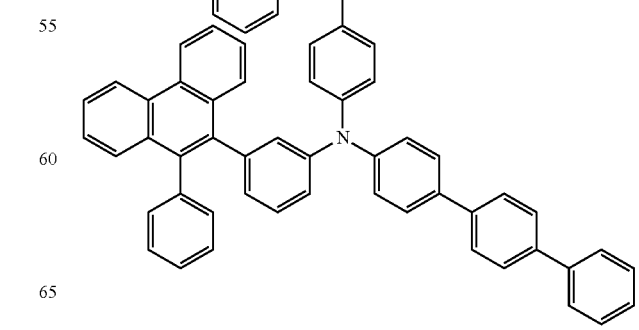

-continued
70
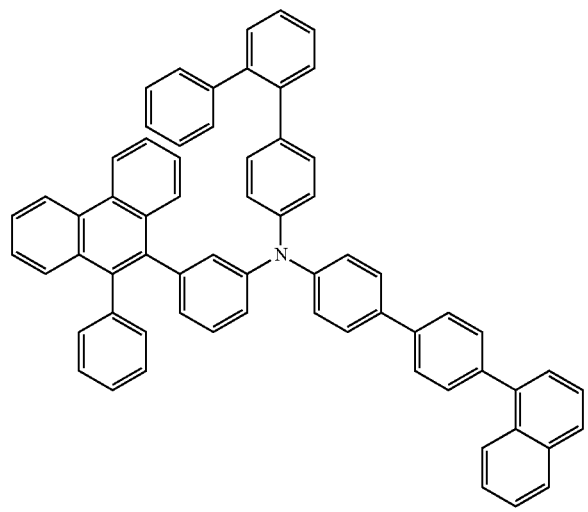
71
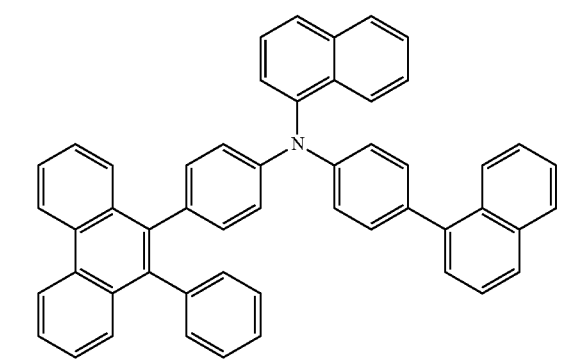
72
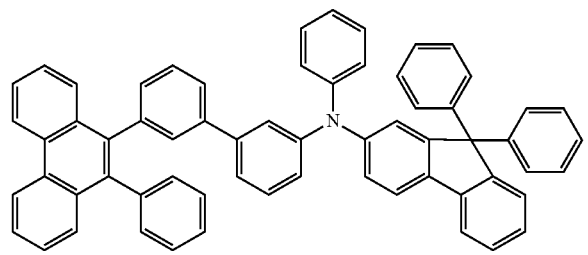
73
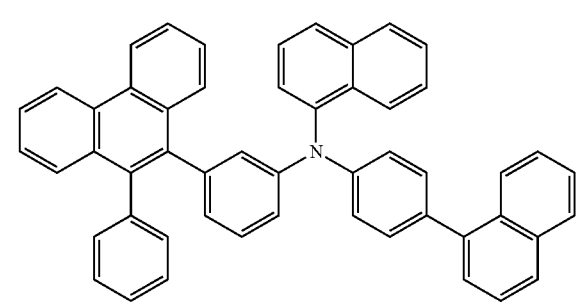
-continued
74
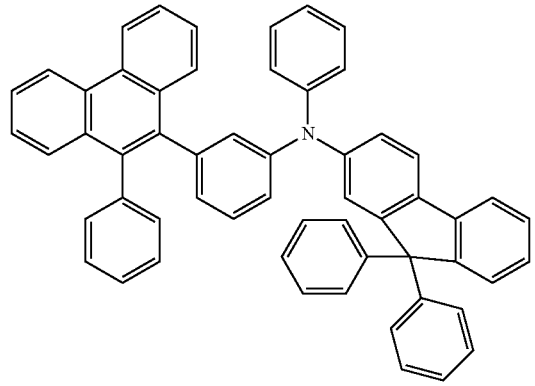
75
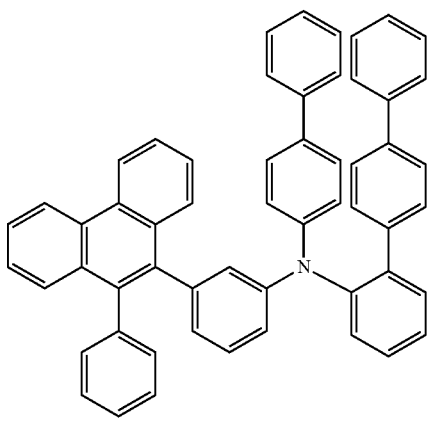
76
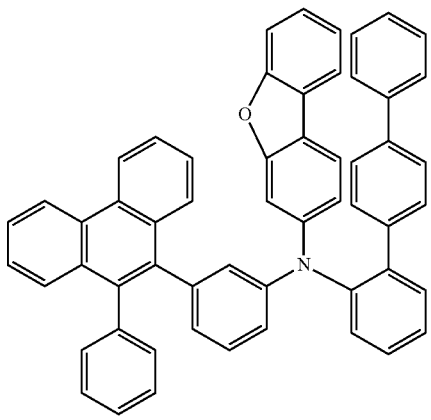
77
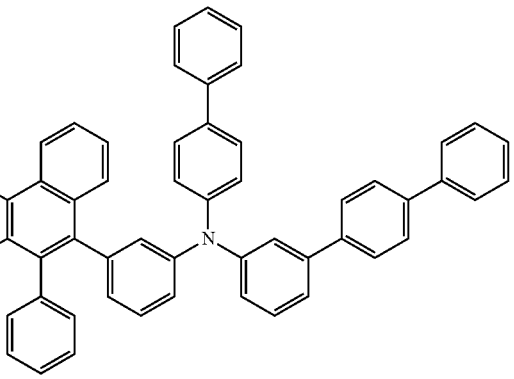

78
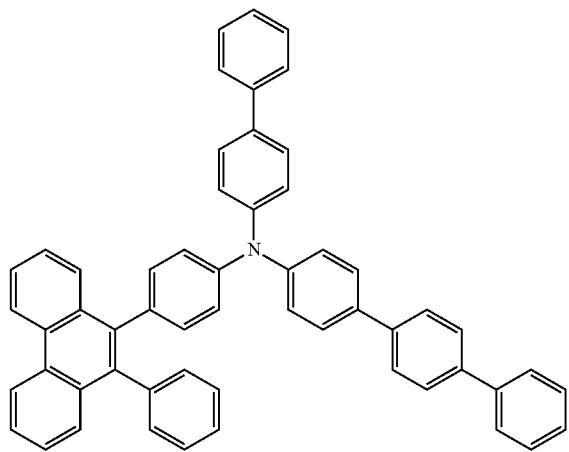
81
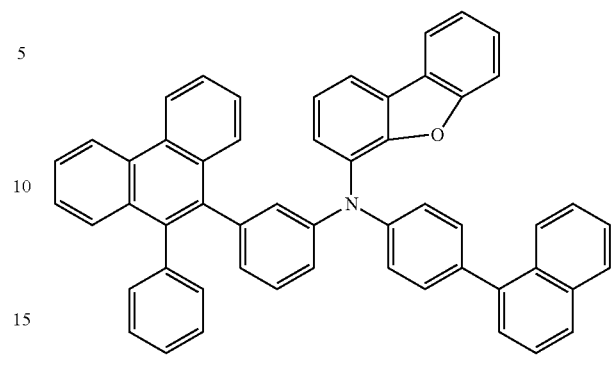
79
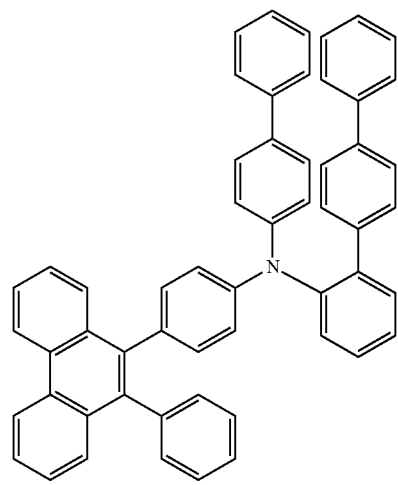
82
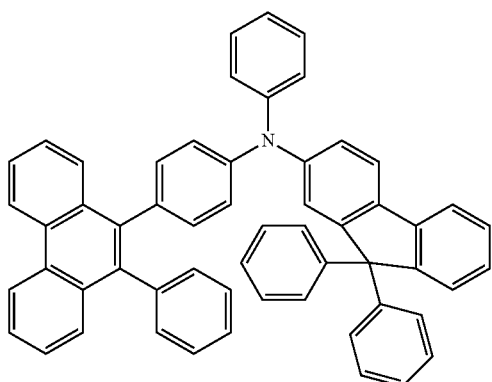
80
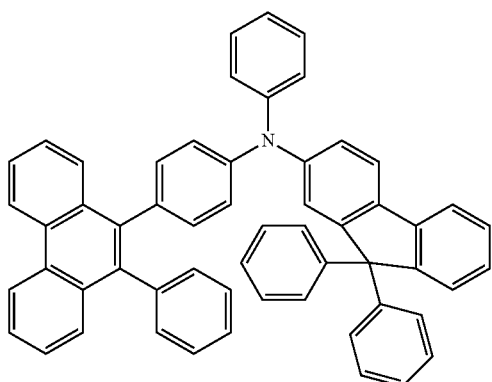
83
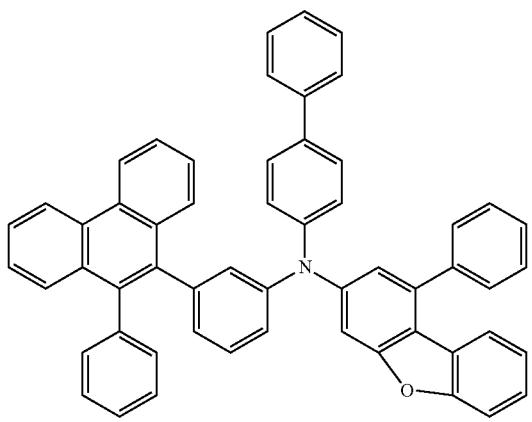

84
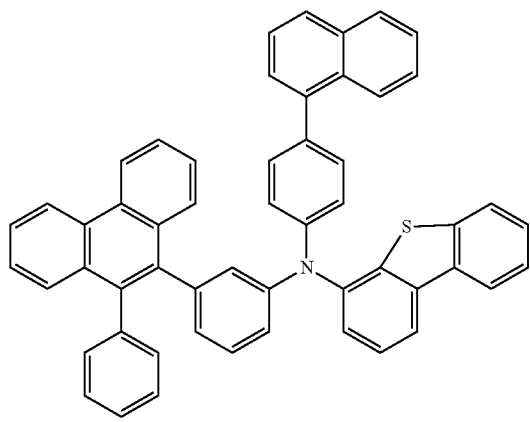
85
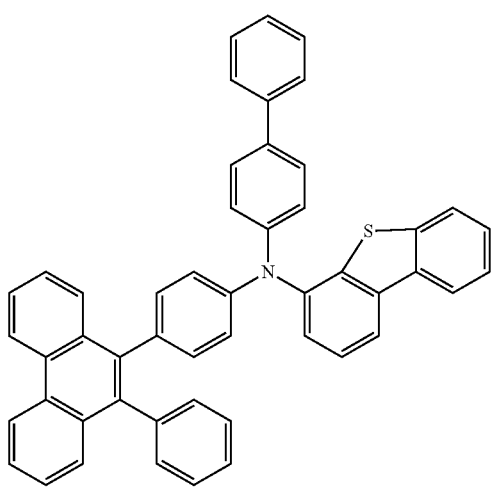
86
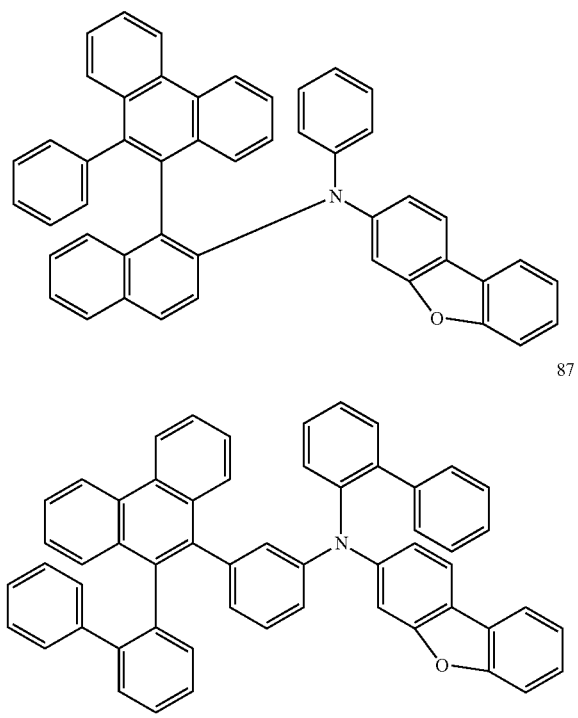
87
88
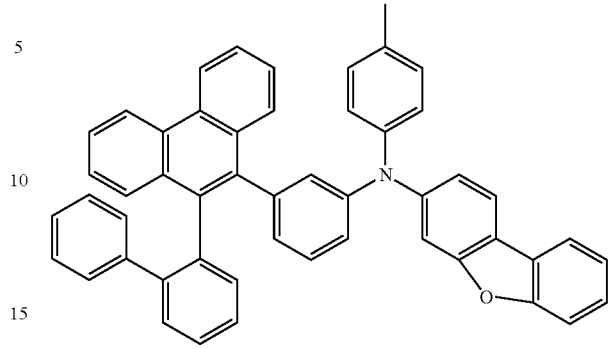
89
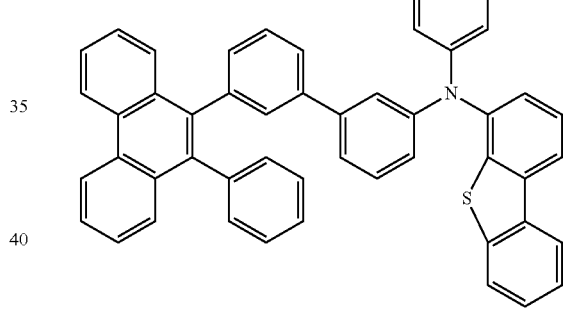
90
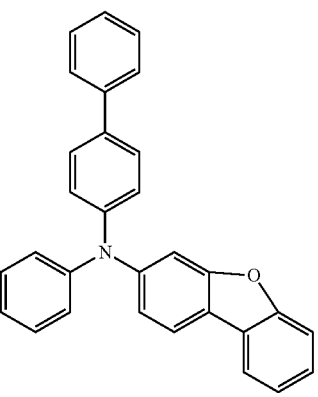

91
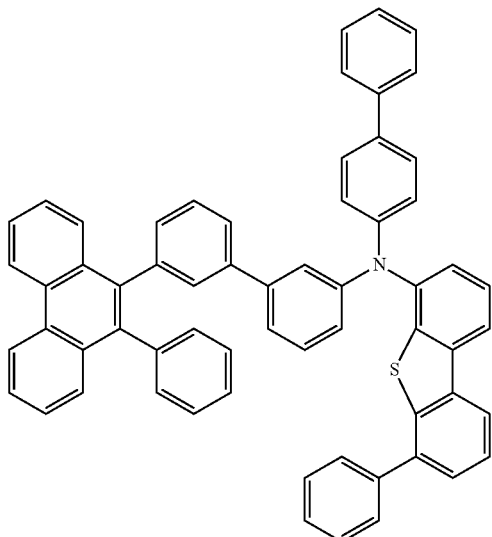
92
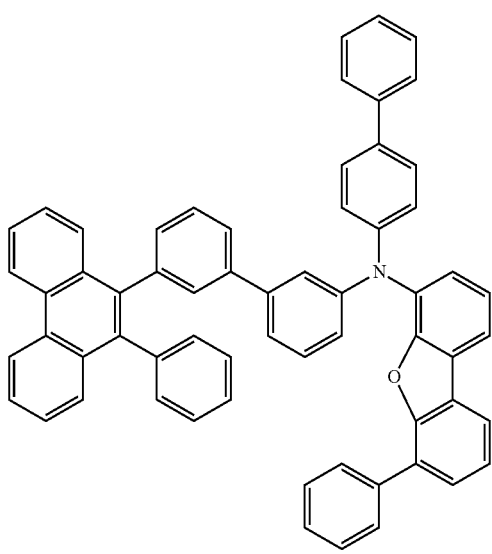
93
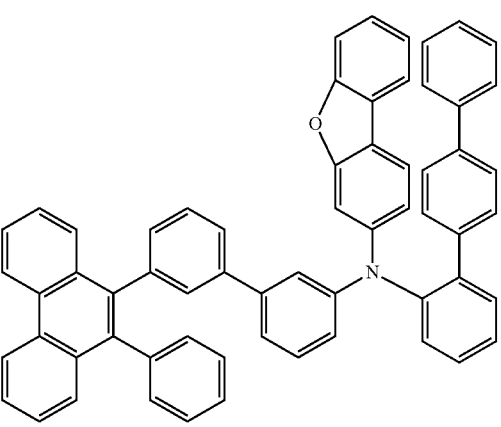
94
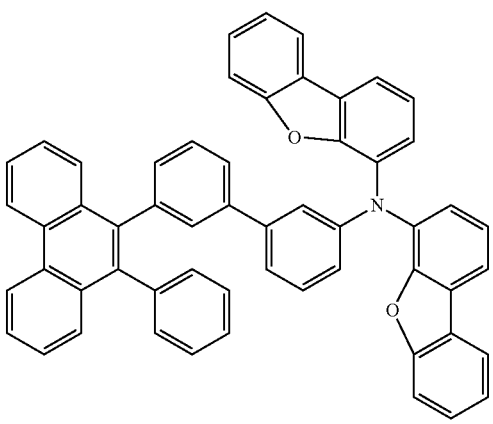
95
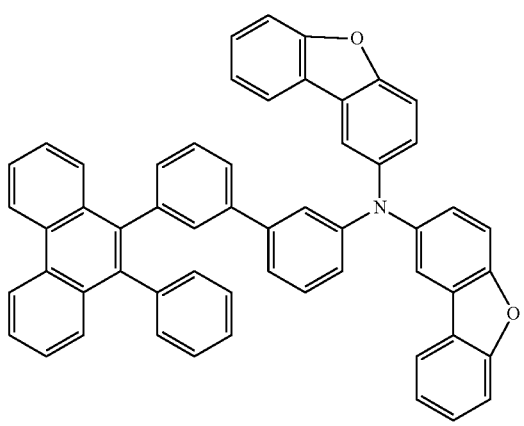
96
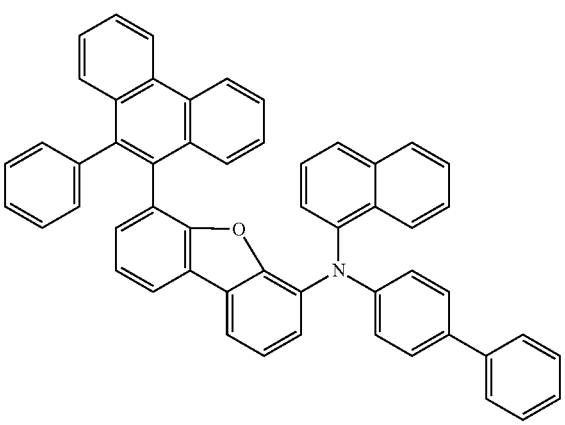

97
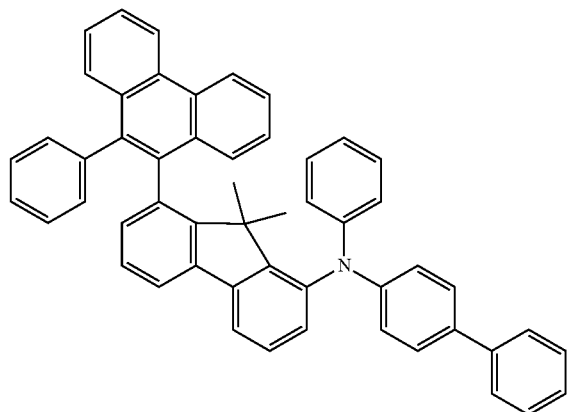
98
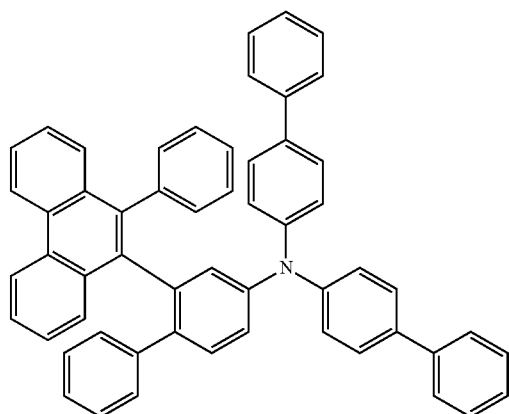
99
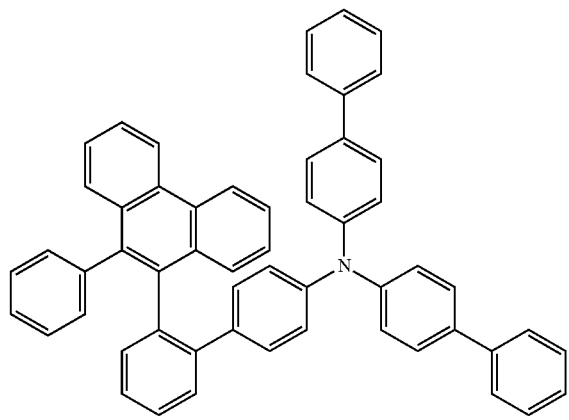
100
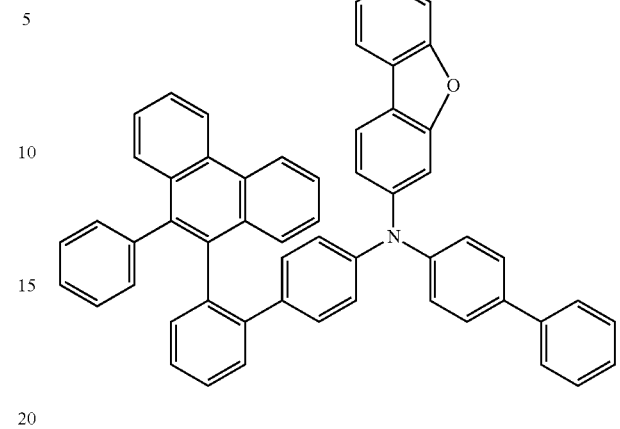
101
102

103
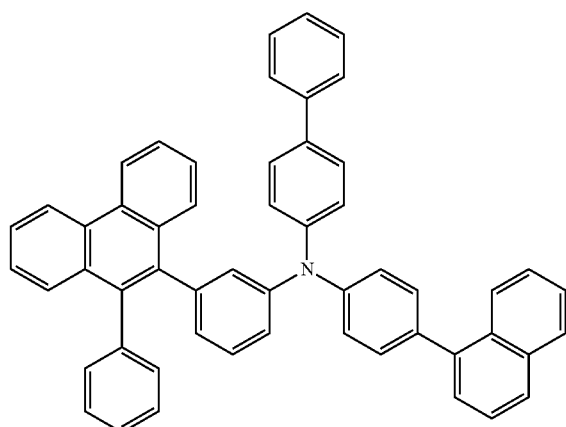
104
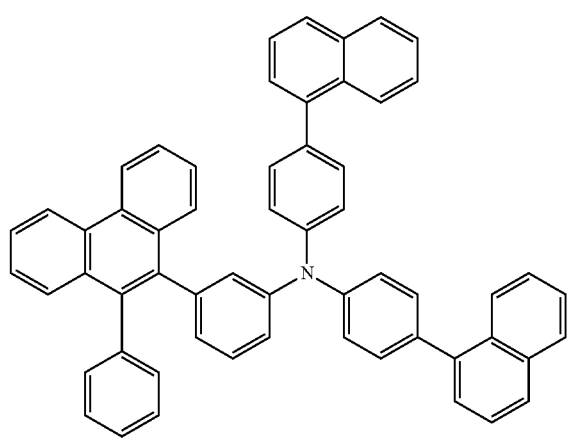
105
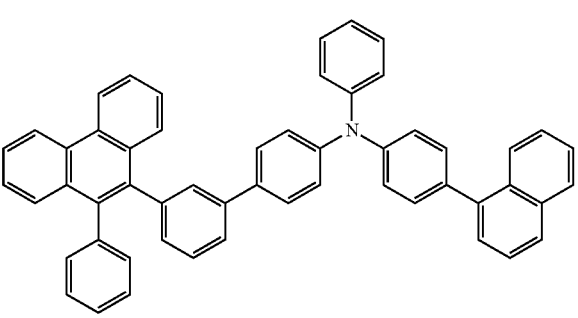
106
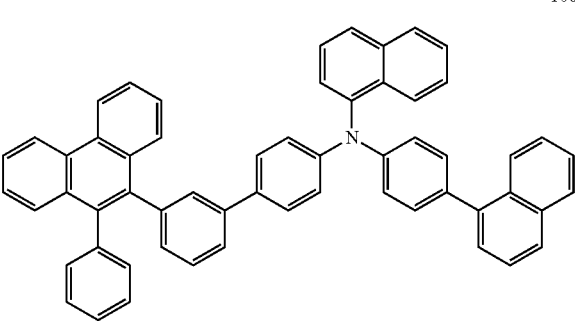
107
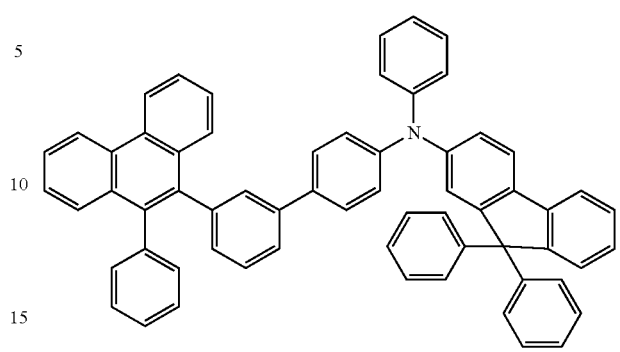
108
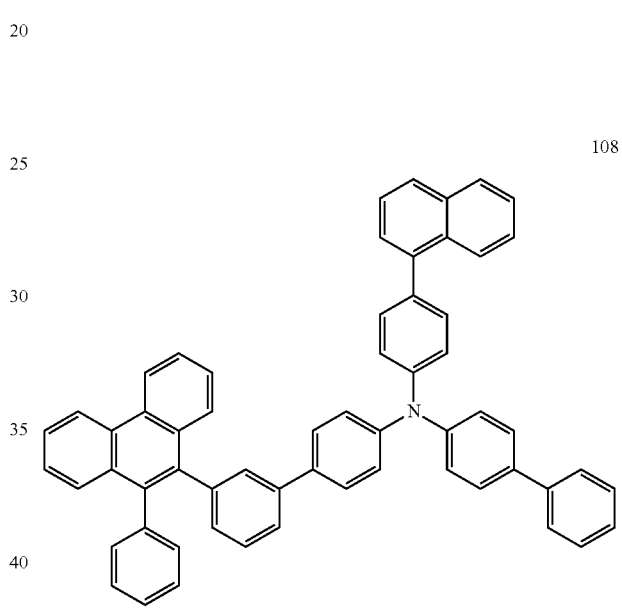
109
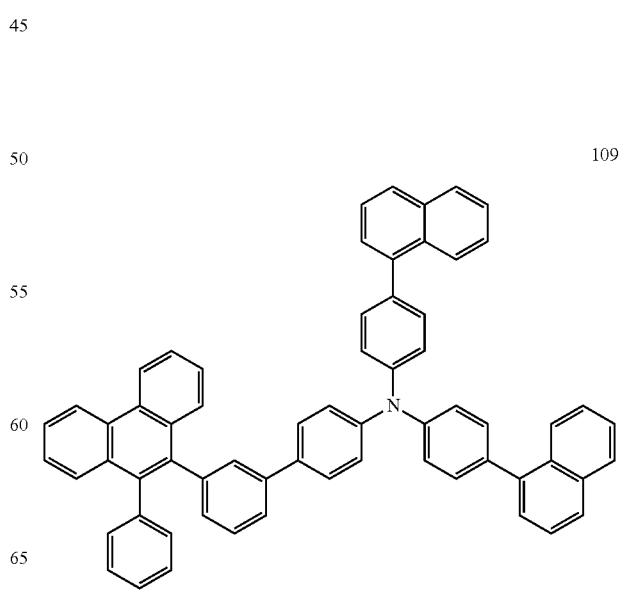

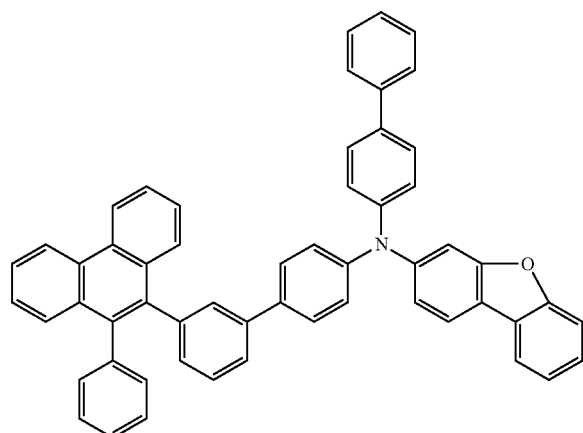
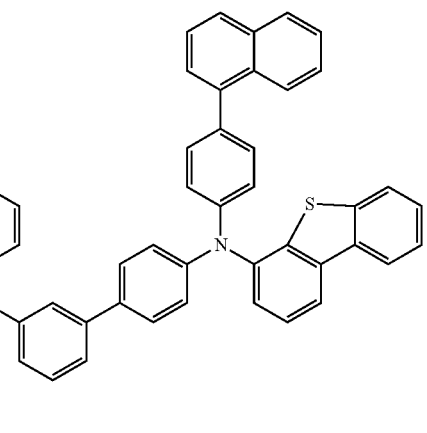

-continued
117
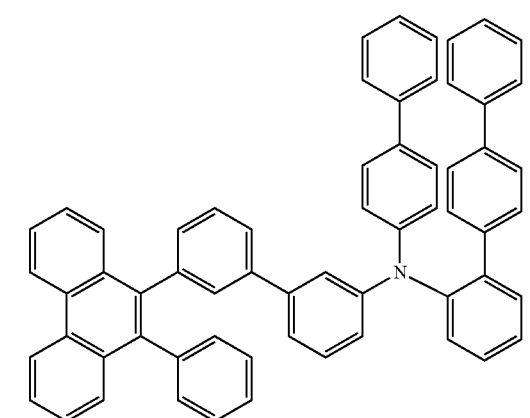
118
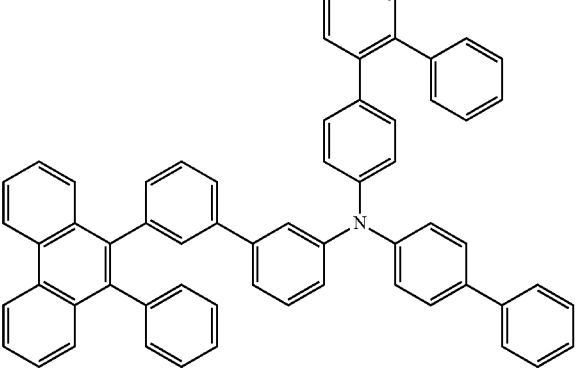
119
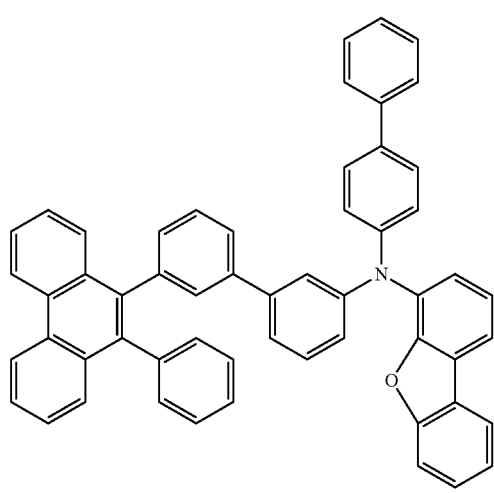
-continued
120
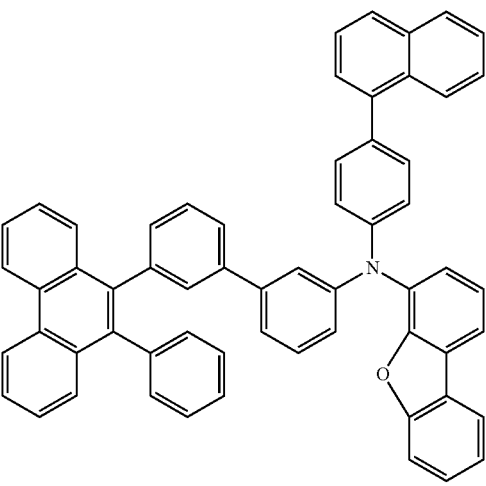
121
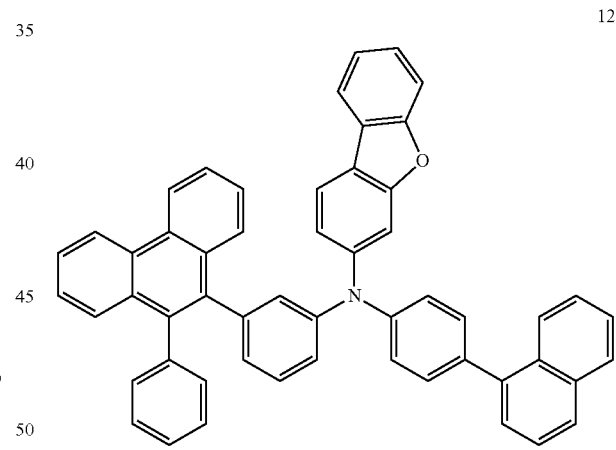
122
123
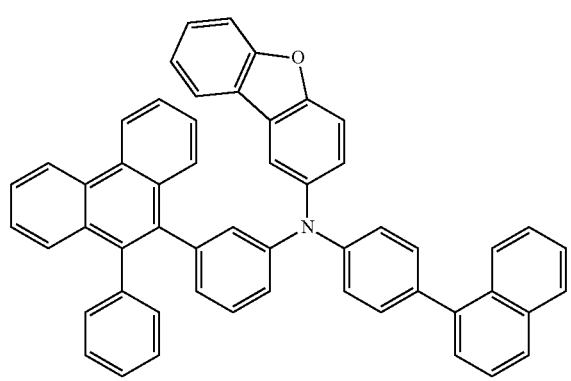

124
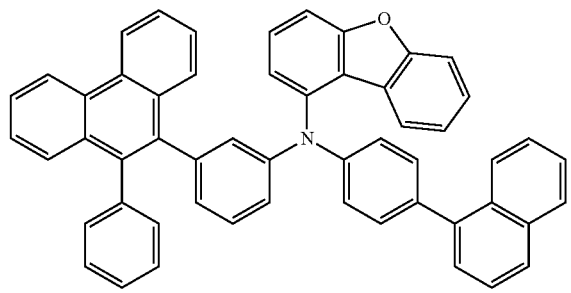
125
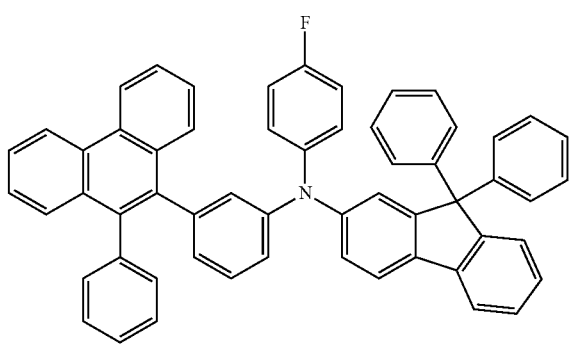
126
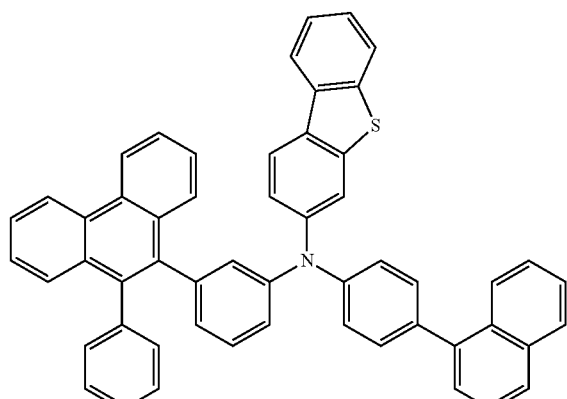
127
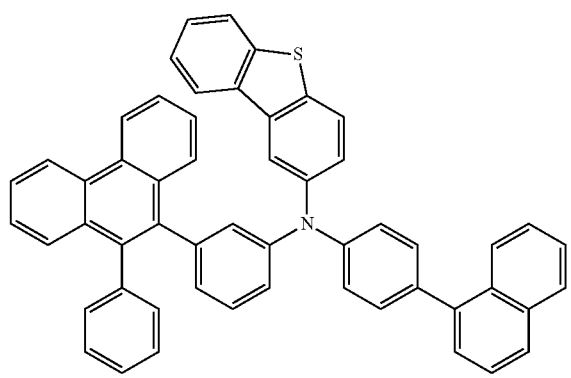
128
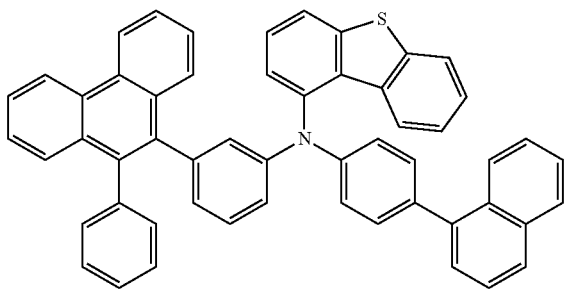
129
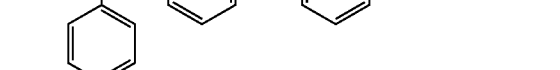
130

131
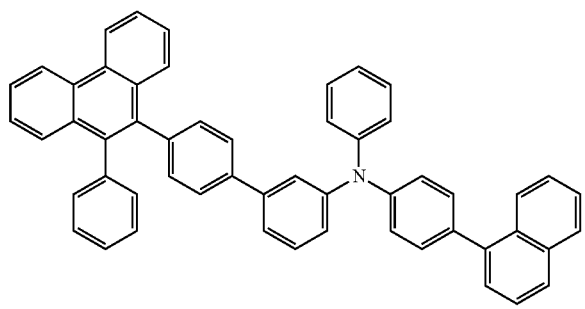
132
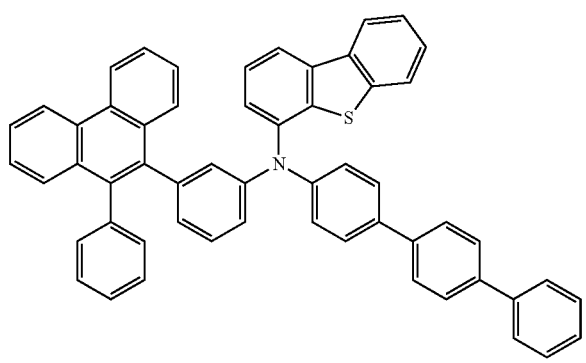
133
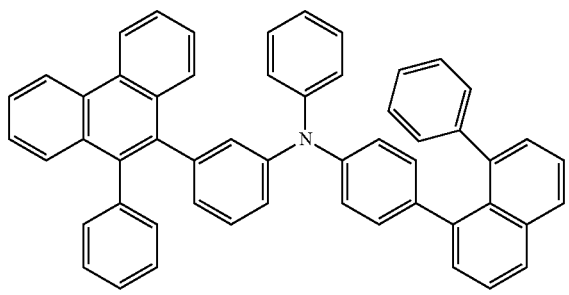
134
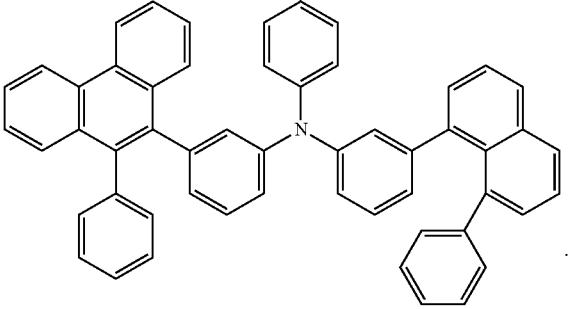
* * * * *